United States Patent
Hetz Flores et al.

(10) Patent No.: US 11,795,476 B2
(45) Date of Patent: Oct. 24, 2023

(54) AAV/UPR-PLUS VIRUS, UPR-PLUS FUSION PROTEIN, GENETIC TREATMENT METHOD AND ITS USE IN THE TREATMENT OF NEURODEGENERATIVE DISEASES, SUCH AS PARKINSON'S DISEASE AND HUNTINGTON'S DISEASE, AMONG OTHERS

(71) Applicant: Universidad de Chile, Santiago (CL)

(72) Inventors: Claudio Hetz Flores, Santiago (CL); Rene Vidal Gomez, Santiago (CL)

(73) Assignee: Universidad de Chile, Santiago (CL)

(*) Notice: Subject to any disclaimer, the term of this patent is extended or adjusted under 35 U.S.C. 154(b) by 500 days.

(21) Appl. No.: 17/109,018

(22) Filed: Dec. 1, 2020

(65) Prior Publication Data

US 2021/0079424 A1 Mar. 18, 2021

Related U.S. Application Data

(63) Continuation of application No. 15/773,723, filed as application No. PCT/CL2016/000070 on Nov. 4, 2016, now Pat. No. 10,889,831.

(30) Foreign Application Priority Data

Nov. 4, 2015 (CL) .................... 3242-2015

(51) Int. Cl.
*C12N 15/86* (2006.01)
*A61P 25/28* (2006.01)
*C07K 14/47* (2006.01)

(52) U.S. Cl.
CPC ............. *C12N 15/86* (2013.01); *A61P 25/28* (2018.01); *C07K 14/4702* (2013.01); *C07K 2319/00* (2013.01); *C07K 2319/42* (2013.01); *C12N 2750/14143* (2013.01)

(58) Field of Classification Search
None
See application file for complete search history.

(56) References Cited

U.S. PATENT DOCUMENTS 10,889,831 B2 * 1/2021 Hetz Flores ....... C07K 14/4702
2017/0059554 A1 3/2017 Dull

FOREIGN PATENT DOCUMENTS

| CL | 201403590 A1 | 7/2015 |
| WO | 2004111194 A2 | 12/2004 |
| WO | 2006028889 A2 | 3/2006 |
| WO | 2016106458 A1 | 7/2016 |
| WO | 2017059554 A1 | 4/2017 |

OTHER PUBLICATIONS

Vidal, et al. (2021) "Enforced dimerization between XBP1s and ATF6f enhances the protective effects of the UPR in models of neurodegeneration", Molecular Therapy, 29(5): 1862-82. (Year: 2021).*
Lobbestael, E., et al., Immunohistochemicl Detection of Transgene Expression in the Brain Using Small Epitope Tags, BMC Biotechnology, 2010, 10:16, 10 pgs.
Mercardo, et al., ER Proteostasis Disturbances in Parkinson's Disease: Novel Insights, Frontiers in Aging Neuroscience, Mar. 27, 2015, 7(39), 5 pgs.
Newman, J.R., et al., Comprehensive identification of human bZIP interactions with coiled-coil arrays. Science Jun. 2003, 300(5628), pp. 2097-2101, DOI: 10.1126/science.1084648.
Shoulders, M.D. et al. Stress-Independent Activation of XBP1s and/or ATF6 ReveaisThree Functionally Diverse 2 ER Proteostasis Environments. Cell Reports, Apr. 2013, 3(4), pp. 1279-1292, DOI:10.1016/j.celrep.2013.03.024.
Yamamoto, K. et al. Transcriptional Induction o Mammalian ER Quality Control Proteins Is Mediated by Single or Combined Action of ATF6 and XBPI, Developmental Cell, Sep. 2007, 13(3), pp. 365-376. DOI: 10.1016/j.devcel.2007.07.018.
I\Charya, A. et al. Experimental Identification of Homodimerizing B-ZIP Families in *Homo sapiens*, Journal of Structural Biology, Aug. 2006, 155(2), pp. 130-139, DOI:10.1016/j.sb.2006.02.018.
Byrd, A.E., et al., Intricately Regulated: A Cellular Toolbox for Fine-Tuning XBP1 Expression and Activity, Cells, 2012; 1(4), pp. 738-753, doi:10.3390/cells1040738. pp. 746 and 748.
International Search Report and Written Opinion for related PCT App No. PCT/CL2016/000070 dated Feb. 28, 2017, 17 pgs.
Sado, M., et al., Protective Effect Against Parkinson's Disease-Related Insults Through the Activation of XBP1, Brain Research, 2009, 257, pp. 16-24.
Zuleta, A., et al., AAV-Mediated Delivery of the Transcription Factor XBP1s into the Striatum Reduces Mutant Huntingtin Aggregation in a Mouse Model of Huntington's Disease, Biochemical and Biophysical Research Communications, 2012, 420, pp. 558-563.
Extended European Search Report for related EP App No. 16861172.1 dated Mar. 6, 2019, 8 pgs.

* cited by examiner

*Primary Examiner* — Robert M Kelly
(74) *Attorney, Agent, or Firm* — Procopio, Cory, Hargreaves & Savitch LLP

(57) ABSTRACT

The present invention presents a sequence of the AAV/UPR-plus virus, a genetic treatment method and its use in the treatment of neurodegenerative diseases, such as Parkinson's and Huntington's diseases, among others, as presented in the in vitro studies shown in FIG. 14/17.

12 Claims, 17 Drawing Sheets

Specification includes a Sequence Listing.

Restriction map of pAAV_XBP1s-LFC-ATF6f - 7701 nt
<Serial Cloner V2.5> -- <17-09-2015  14:29>

Restriction map of pAAV_Xbp1s-LF-ATF6f - 7809 nt
<Serial Cloner V2.5> -- <17-09-2015 14:28>

Restriction map of pAAV_Xbp1s-L4H4-Atf6f - 7719 nt
<Serial Cloner V2.5> -- <17-09-2015 14:24>

Restriction map of pAAV_ATF6 - LFG -XBP1s - 7701 nt
<Serial Cloner V2.5> -- <17-09-2015 13:13>

Restriction map of pAAV_ATF6 - LF -XBP1s - 7809 nt
<Serial Cloner V2.5> -- <17-09-2015 13:05>

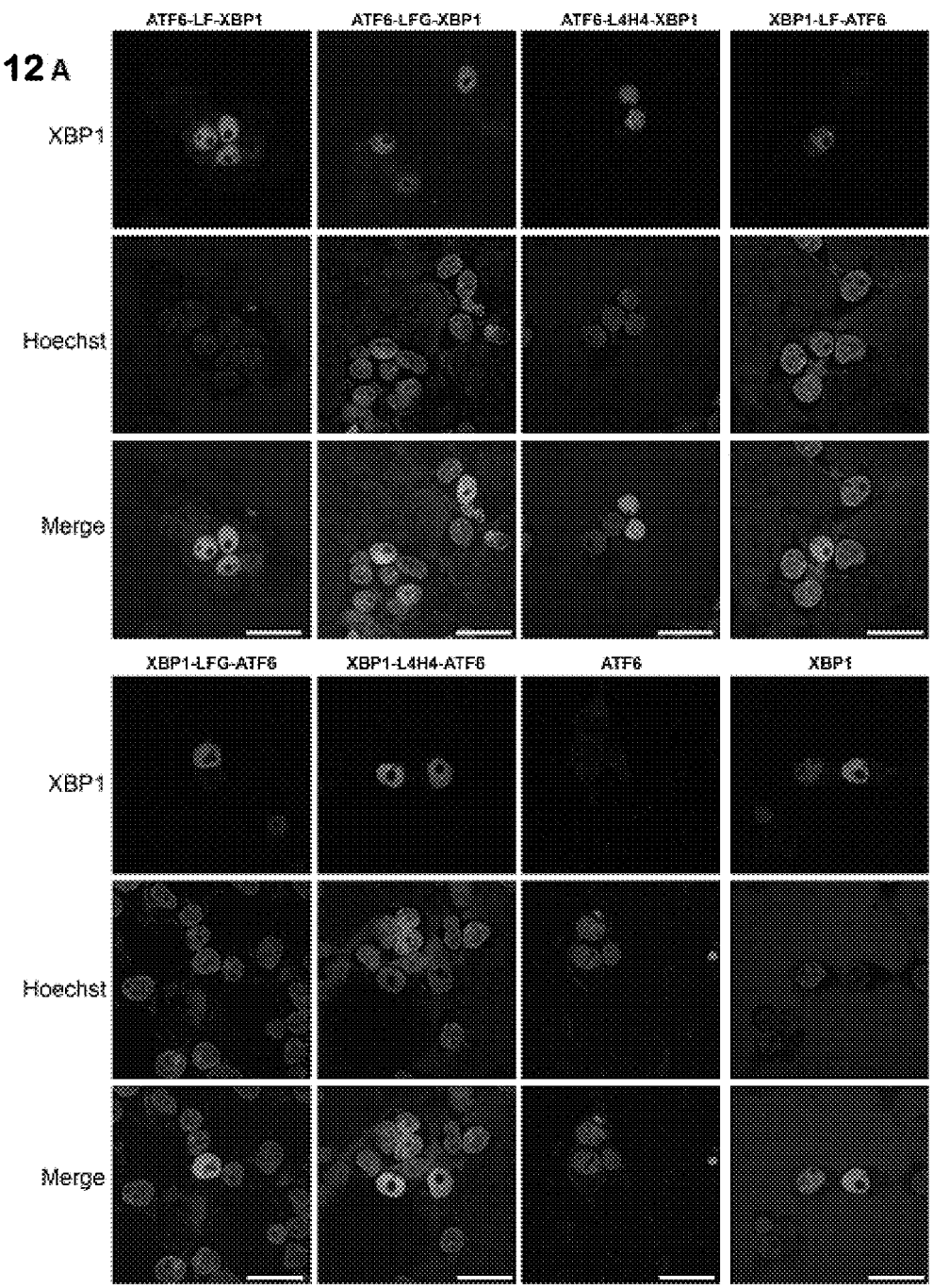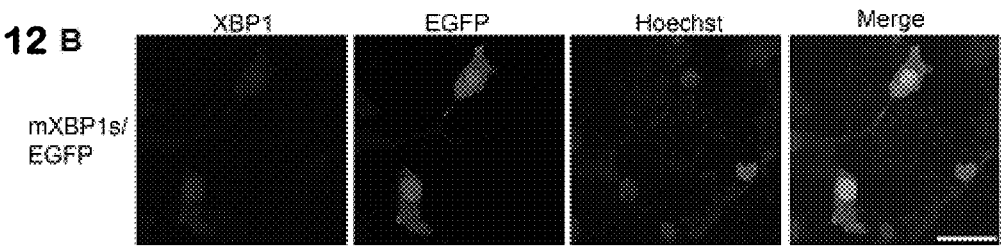

| Plasmid | Experiment 1 | Experiment 2 | Experiment 3 | average | SEM |
|---|---|---|---|---|---|
| pAAV_ATF6f-LFG-XBP1s-HA | 101,15170 | 99,62383 | 125,42410 | 108,73321 | 8,357091867 |
| pAAV_ATF6f-LF-XBP1s-HA | 88,52831 | 119,74700 | 191,87580 | 133,3837033 | 30,60308089 |
| pAAV_ATF6f-L4H4-XBP1s-HA | 79,35313 | 77,71852 | 71,44357 | 76,17174 | 2,410717813 |
| pAAV_XBP1s-LFG-ATF6f-HA | 17,61713 | 12,63527 | 21,43350 | 17,26196667 | 2,563652391 |
| pAAV_XBP1s-LF-ATF6f-HA | 15,62922 | 11,84960 | 23,46904 | 16,98928667 | 3,428142203 |
| pAAV_XBP1s-L4H4-ATF6f-HA | 9,22897 | 11,24907 | 10,32660 | 10,26821267 | 0,583883502 |
| pAAV_ATF6f-HA | 120,18800 | 122,15340 | 139,62090 | 127,3207667 | 6,17618165 |
| pAAV_XBP1s-HA | 47,81040 | 47,95798 | 46,66553 | 47,47797 | 0,408447887 |
| pAAV_ATF6f-HA + pAAV_XBP1s-HA | 100 | 100 | 100 | 100 | 0 |
| pCDNA3_mXBP1 | 77,29633 | 120,59790 | 116,02510 | 104,6397767 | 13,73530344 |
| pCDNA3 | 4,87410 | 6,95335 | 4,20880 | 5,345415667 | 0,826588582 |

SEQUENCE LISTING

```
<160> NUMBER OF SEQ ID NOS: 32

<210> SEQ ID NO 1
<211> LENGTH: 7809
<212> TYPE: DNA
<213> ORGANISM: Artificial Sequence
<220> FEATURE:
<223> OTHER INFORMATION: pAAV_ATF6f-LF-XBP1s-HA

<400> SEQUENCE: 1
ggcggatcca attgcctagg cccaagggcg aattgtcacg actccacccc tccaggaacc      60
cctagtgatg gagttggcca ctccctctct gcgcgctcgc tcgctcactg aggccgcccg     120
ggcaaagccc gggcgtcggg cgacctttgg tcgcccggcc tcagtgagcg agcgagcgcg     180
```

-continued

```
cagagaggga gtggcccaga tctgatatca tcgatgaatt caagcttcag ctgctcgagt      240
tctatagtgt cacctaaatc gtatgtgtat gatacataag gttatgtatt aattgtagcc      300
gcgttctaac gacaatatgt ccatatggtg cactctcagt acaatctgct ctgatgccgc      360
atagttaagc cagccccgac acccgccaac acccgctgac gcgccctgac gggcttgtct      420
gctcccggca tccgcttaca gacaagctgt gaccgtctcc gggagctgca tgtgtcagag      480
gttttcaccg tcatcaccga aacgcgcgag acgaaagggc tcgtgatac gcctattttt       540 ataggttaat gtcatgataa taatggtttc ttagacgtca ggtggcactt tcggggaaa       600 tgtgcgcgga acccctattt gtttattttt ctaaatacat tcaaatatgt atccgctcat      660
gagacaataa ccctgataaa tgcttcaata atattgaaaa aggaagagta tgagtattca      720
acatttccgt gtcgccctta ttcccttttt tgcggcattt tgccttcctg ttttgctca       780 cccagaaacg ctggtgaaag taaaagatgc tgaagatcag ttgggtgcac gagtgggtta      840
catcgaactg gatctcaaca gcggtaagat ccttgagagt tttcgccccg aagaacgttt      900
tccaatgatg agcacttta aagttctgct atgtggcgcg gtattatccc gtattgacgc       960
cgggcaagag caactcggtc gccgcataca ctattctcag aatgacttgg ttgagtactc     1020
accagtcaca gaaaagcatc ttacggatgg catgacagta agagaattat gcagtgctgc     1080
cataaccatg agtgataaca ctgcggccaa cttacttctg acaacgatcg gaggaccgaa     1140
ggagctaacc gcttttttgc acaacatggg ggatcatgta actcgccttg atcgttggga     1200
accggagctg aatgaagcca taccaaacga cgagcgtgac accacgatgc ctgtagcaat     1260
ggcaacaacg ttgcgcaaac tattaactgg cgaactactt actctagctt cccggcaaca     1320
attaatagac tggatggagg cggataaagt tgcaggacca cttctgcgct cggcccttcc     1380
ggctggctgg tttattgctg ataaatctgg agccggtgag cgtgggtctc gcggtatcat     1440
tgcagcactg gggccagatg gtaagccctc ccgtatcgta gttatctaca cgacggggag     1500
tcaggcaact atggatgaac gaaatagaca gatcgctgag ataggtgcct cactgattaa     1560
gcattggtaa ctgtcagacc aagtttactc atatatactt tagattgatt taaaacttca     1620
tttttaattt aaaaggatct aggtgaagat cctttttgat aatctcatga ccaaaatccc     1680
ttaacgtgag ttttcgttcc actgagcgtc agaccccgta gaaaagatca aggatcttc      1740 ttgagatcct ttttttctgc gcgtaatctg ctgcttgcaa acaaaaaaac caccgctacc     1800
agcggtggtt tgtttgccgg atcaagagct accaactctt tttccgaagg taactggctt     1860
cagcagagcg cagataccaa atactgtcct tctagtgtag ccgtagttag gccaccactt     1920
caagaactct gtagcaccgc ctacatacct cgctctgcta atcctgttac cagtggctgc     1980
tgccagtggc gataagtcgt gtcttaccgg gttggactca agacgatagt taccggataa     2040
ggcgcagcgg tcgggctgaa cggggggttc gtgcacacag cccagcttgg agcgaacgac     2100
ctacaccgaa ctgagatacc tacagcgtga gcattgagaa agcgccacgc ttcccgaagg     2160
gagaaaggcg gacaggtatc cggtaagcgg cagggtcgga acaggagagc gcacgaggga     2220
gcttccaggg ggaaacgcct ggtatcttta tagtcctgtc gggtttcgcc acctctgact     2280
tgagcgtcga tttttgtgat gctcgtcagg gggcggagc ctatggaaaa acgccagcaa      2340
cgcggccttt ttacggttcc tggccttttg ctggcctttt gctcacatgt tctttcctgc     2400
gttatcccct gattctgtgg ataaccgtat taccgccttt gagtgagctg ataccgctcg     2460
ccgcagccga acgaccgagc gcagcgagtc agtgagcgag gaagcggaag agcgcccaat     2520
acgcaaaccg cctctccccg cgcgttggcc gattcattaa tgcaggttaa cctggcttat     2580
```

```
cgaaattaat acgactcact atagggagac cggcagatct gtccctctct gcgcgctcgc    2640
tcgctcactg aggccgcccg ggcaaagccc gggcgtcggg cgacctttgg tcgcccggcc    2700
tcagtgagcg agcgagcgcg cagagaggga gtggccaact ccatcactag gggttccttg    2760
tagttaatga ttaacccgcc atgctactta tctacaattc gcccttcgga cgcgtggctt    2820
cgaactaggc aattgcatga agaatctgct tagggttagg cgttttgcgc tgcttcgcga    2880
tgtacgggcc agatatacgc gttgacattg attattgact agttattaat agtaatcaat    2940
tacggggtca ttagttcata gcccatatat ggagttccgc gttacataac ttacggtaaa    3000
tggcccgcct ggctgaccgc ccaacgaccc ccgcccattg acgtcaataa tgacgtatgt    3060
tcccatagta acgccaatag ggactttcca ttgacgtcaa tgggtggagt atttacggta    3120
aactgcccac ttggcagtac atcaagtgta tcatatgcca gtacgcccc ctattgacgt     3180 caatgacggt aaatggcccg cctggcatta tgcccagtac atgaccttat gggactttcc    3240
tacttggcag tacatctacg tattagtcat cgctattacc atggtgatgc ggttttggca    3300
gtacatcaat gggcgtggat agcggtttga ctcacgggga tttccaagtc tccaccccat    3360
tgacgtcaat gggagtttgt tttggcacca aaatcaacgg gactttccaa aatgtcgtaa    3420
caactccgcc ccattgacgc aaatgggcgg taggcgtgta cggtgggagg tctatataag    3480
cagagctctc tggctaacta gagaacccac tgcttactgg cttatcgaaa ttaatacgac    3540
tcactatagg gagacccaag ctggctagcg tttaaactta agcttcctgg ctatggggga    3600
gccggctggg gttgccggca ccatggagtc acctttagc ccgggactct tcacaggct     3660 ggatgaagat tgggattctg ctctctttgc tgaactcggt tatttcacag acactgatga    3720
gctgcaattg gaagcagcaa atgagacgta tgaaaacaat tttgataatc ttgattttga    3780
tttggatttg atgccttggg agtcagacat ttgggacatc aacaaccaaa tctgtacagt    3840
taaagatatt aaggcagaac ctcagccact ttctccagcc tcctcaagtt attcagtctc    3900
gtctcctcgg tcagtggact cttattcttc aactcagcat gttcctgagg agttggattt    3960
gtcttctagt tctcagatgt ctccccttc cttatatggt gaaaactcta atagtctctc     4020
ttcagcggag ccactgaagg aagataagcc tgtcactggg cctaggaaca agactgaaaa    4080
tggactgact ccaaagaaaa aaattcaggt gaattcaaaa ccttcaattc agcccaagcc    4140
tttattgctt ccagcagcac ccaagactca aacaaactcc agtgttccag caaaaaccat    4200
cattattcag acagtaccaa cgcttatgcc attggcaaag cagcaaccaa ttatcagttt    4260
acaacctgca cccactaaag gccagacggt tttgctgtct cagcctactg tggtacaact    4320
tcaagcacct ggagttctgc cctctgctca gccagtcctt gctgttgctg ggggagtcac    4380
acagctccct aatcacgtgg tgaatgtggt accagcccct tcagcgaata gcccagtgaa    4440
tggaaaactt tccgtgacta aacctgtcct acaaagtacc atgagaaatg tcggttcaga    4500
tattgctgtg ctaaggagac agcaacgtat gataaaaaat cgagaatccg cttgtcagtc    4560
tcgcaagaag aagaaagaat atatgctagg gttagaggcg agattaaagg ctgccctctc    4620
agaaaacgag caactgaaga aagaaaatgg aacactgaag cggcagctgg atgaagttgt    4680
gtcagagaac cagaggcttc tatttaataa agaacaacaa aatgcgtttt atgaaaatact    4740 acatctaccg aatctaaatg aagaacaacg taatggtttt atacaatcgc taaaagatga    4800
tccgtcgcaa tcgcgaatc tactagcgga agcgaaaaaa ctaaatgatg cgcaagcggc    4860
ggcgatggtg gtggtggcag ccgcgccgaa cccggccgac gggaccccta aagttctgct    4920
```

```
tctgtcgggg cagcccgcct ccgccgccgg agcccggcc  ggccaggccc tgccgctcat   4980
ggtgccagcc cagagagggg ccagcccgga ggcagcgagc ggggggctgc cccaggcgcg   5040
caagcgacag cgcctcacgc acctgagccc cgaggagaag gcgctgagga ggaaactgaa   5100
aaacagagta gcagctcaga ctgccagaga tcgaaagaag gctcgaatga gtgagctgga   5160
acagcaagtg gtagatttag aagaagagaa ccaaaaactt ttgctagaaa atcagctttt   5220
acgagagaaa actcatggcc ttgtagttga gaaccaggag ttaagacagc gcttggggat   5280
ggatgccctg gttgctgaag aggaggcgga agccaagggg aatgaagtga ggccagtggc   5340
cgggtctgct gagtccgcag caggtgcagg cccagttgtc acccctccag aacatctccc   5400
catggattct ggcggtattg actcttcaga ttcagagtct gatatcctgt tgggcattct   5460
ggacaacttg gacccagtca tgttcttcaa atgcccttcc ccagagcctg ccagcctgga   5520
ggagctccca gaggtctacc cagaaggacc cagttcctta ccagcctccc tttctctgtc   5580
agtggggacg tcatcagcca agctggaagc cattaatgaa ctaattcgtt ttgaccacat   5640
atataccaag cccctagtct tagagatacc ctctgagaca gagagccaag ctaatgtggt   5700
agtgaaaatc gaggaagcac ctctcagccc ctcagagaat gatcaccctg aattcattgt   5760
ctcagtgaag aagaacctg tagaagatga cctcgttccg gagctgggta tctcaaatct   5820
gctttcatcc agccactgcc caaagccatc ttcctgccta ctggatgctt acagtgactg   5880
tggatacggg ggttcccttt ccccattcag tgacatgtcc tctctgcttg gtgtaaacca   5940
ttcttgggag gacactttg ccaatgaact ctttccccag ctgattagtg tctacccata   6000
cgatgttcca gattacgcaa tgtaaagagc cacataacac tgggccccct tccctgacca   6060
tcacattgcc tagaggatag cataggcctg aagggcgaat tcagcacac tggcggccgt   6120
tactagaggg cccgtttaaa cccgctgatc acctcgactg tgccttctag ttgccagcca   6180
tctgttgttt gcccctcccc cgtgccttcc ttgaccctgg aaggtgccac tcccactgtc   6240
ctttcctaat aaaatgagga aattgcatcg cattgtctga gtaggtgtca ttctattctg   6300
gggggtgggg tggggcagga cagcaagggg gaggattggg aagacaatag caggcatgcc   6360
tgcagcggtc cggtcgactc tagaggatcc gaaaaaacct cccacacctc cccctgaacc   6420
tgaaacataa aatgaatgca attgttgttg ttaacttgtt tattgcagct tataatggtt   6480
acaaataaag caatagcatc acaaatttca caaataaagc atttttttca ctgcattcta   6540
gttgtggttt gtccaaactc atcaatgtat cttatcatgt ctggatcccc gcggtggcgg   6600
ccgcactagt cccgggttaa ttaagctagc agatcttgat cacctaggcg tacgatttgg   6660
ccgctttaca tggtggcgac cggggatcct ctagtaccaa gctaattcct cacgacacct   6720
gaaatggaag aaaaaaactt tgaaccactg tctgaggctt gagaatgaac caagatccaa   6780
actcaaaaag ggcaaattcc aaggagaatt acatcaagtg ccaagctggc ctaacttcag   6840
tctccaccca ctcagtgtgg ggaaactcca tcgcataaaa cccctccccc caacctaaag   6900
acgacgtact ccaaaagctc gagaactaat cgaggtgcct ggacgcgcc cggtactccg   6960
tggagtcaca tgaagcgacg gctgaggacg gaaaggccct tttcctttgt gtgggtgact   7020
cacccgcccg ctctcccgag cgccgcgtcc tccattttga gctccctgca gcagggccgg   7080
gaagcggcca tctttccgct cacgcaactg gtgccgaccg ggcagccctt gccgccagg   7140
gcggggcgat acacggcggc gcgaggccag gcaccgagagc aggccggcca gcttgagact   7200
accccgtcc gattctcggt ggccgcgctc gcaggccccg cctcgccgaa catgtgcgct   7260
gggacgcacg ggccccgtcg ccgcccgcgg ccccaaaaac cgaaatacca gtgtgcagat   7320
```

```
cttggcccgc atttacaaga ctatcttgcc agaaaaaaag cgtcgcagca ggtcatcaaa    7380
aattttaaat ggctagagac ttatcgaaag cagcgagaca ggcgcgaagg tgccaccaga    7440
ttcgcacgcg gcggcccag cgcccaggcc aggcctcaac tcaagcacga ggcgaagggg     7500
ctccttaagc gcaaggcctc gaactctccc acccacttcc aacccgaagc tcgggatcaa    7560
gaatcacgta ctgcagccag gtggaagtaa ttcaaggcac gcaagggcca taacccgtaa    7620
agaggccagg cccgcgggaa ccacacacgg cacttacctg tgttctggcg gcaaacccgt    7680
tgcgaaaaag aacgttcacg gcgactactg cacttatata cggttctccc ccaccctcgg    7740
gaaaaaggcg gagccagtac acgacatcac tttcccagtt taccccgcgc caccttctct    7800
aggcaccgg                                                            7809
```

<210> SEQ ID NO 2
<211> LENGTH: 7701
<212> TYPE: DNA
<213> ORGANISM: Artificial Sequence
<220> FEATURE:
<223> OTHER INFORMATION: pAAV_ATF6f-LFG-XBP1s-HA

<400> SEQUENCE: 2

```
ggcggatcca attgcctagg cccaagggcg aattgtcacg actccacccc tccaggaacc      60
cctagtgatg gagttggcca ctccctctct gcgcgctcgc tcgctcactg aggccgcccg     120
ggcaaagccc gggcgtcggg cgacctttgg tcgcccggcc tcagtgagcg agcgagcgcg     180
cagagaggga gtggcccaga tctgatatca tcgatgaatt caagcttcag ctgctcgagt     240
tctatagtgt cacctaaatc gtatgtgtat gatacataag gttatgtatt aattgtagcc     300
gcgttctaac gacaatatgt ccatatggtg cactctcagt acaatctgct ctgatgccgc     360
atagttaagc cagccccgac acccgccaac accgctgac gcgccctgac gggcttgtct     420
gctcccggca tccgcttaca gacaagctgt gaccgtctcc gggagctgca tgtgtcagag     480
gttttcaccg tcatcaccga aacgcgcgag acgaaagggc ctcgtgatac gcctattttt     540
ataggttaat gtcatgataa taatggtttc ttagacgtca ggtggcactt ttcggggaaa     600
tgtgcgcgga accctatt gtttattttt ctaaatacat tcaaatatgt atccgctcat      660
gagacaataa ccctgataaa tgcttcaata atattgaaaa aggaagagta tgagtattca    720
acatttccgt gtcgccctta ttcccttttt tgcggcattt tgccttcctg tttttgctca    780
cccagaaacg ctggtgaaag taaaagatgc tgaagatcag ttgggtgcac gagtgggtta    840
catcgaactg gatctcaaca gcggtaagat ccttgagagt tttcgccccg aagaacgttt    900
tccaatgatg agcactttta aagttctgct atgtggcgcg gtattatccc gtattgacgc    960
cgggcaagag caactcggtc gccgcataca ctattctcag aatgacttgg ttgagtactc   1020
accagtcaca gaaaagcatc ttacggatgg catgacagta agagaattat gcagtgctgc   1080
cataaccatg agtgataaca ctgcggccaa cttacttctg acaacgatcg gaggaccgaa   1140
ggagctaacc gcttttttgc acaacatggg ggatcatgta actcgccttg atcgttggga   1200
accggagctg aatgaagcca taccaaacga cgagcgtgac accacgatgc ctgtagcaat   1260
ggcaacaacg ttgcgcaaac tattaactgg cgaactactt actctagctt cccggcaaca   1320
attaatagac tggatggagg cggataaagt tgcaggacca cttctgcgct cggcccttcc   1380
ggctggctgg tttattgctg ataaatctgg agccggtgag cgtgggtctc gcggtatcat   1440
tgcagcactg gggccagatg gtaagccctc ccgtatcgta gttatctaca cgacggggag   1500
```

-continued

| | |
|---|---|
| tcaggcaact atggatgaac gaaatagaca gatcgctgag ataggtgcct cactgattaa | 1560 |
| gcattggtaa ctgtcagacc aagtttactc atatatactt tagattgatt taaaacttca | 1620 |
| tttttaattt aaaaggatct aggtgaagat ccttttttgat aatctcatga ccaaaatccc | 1680 |
| ttaacgtgag ttttcgttcc actgagcgtc agacccccgta gaaaagatca aaggatcttc | 1740 |
| ttgagatcct ttttttctgc gcgtaatctg ctgcttgcaa acaaaaaaac caccgctacc | 1800 |
| agcggtggtt tgtttgccgg atcaagagct accaactctt tttccgaagg taactggctt | 1860 |
| cagcagagcg cagataccaa atactgtcct tctagtgtag ccgtagttag gccaccactt | 1920 |
| caagaactct gtagcaccgc ctacatacct cgctctgcta atcctgttac cagtggctgc | 1980 |
| tgccagtggc gataagtcgt gtcttaccgg gttggactca agacgatagt taccggataa | 2040 |
| ggcgcagcgg tcgggctgaa cggggggttc gtgcacacag cccagcttgg agcgaacgac | 2100 |
| ctacaccgaa ctgagatacc tacagcgtga gcattgagaa agcgccacgc ttcccgaagg | 2160 |
| gagaaaggcg gacaggtatc cggtaagcgg cagggtcgga acaggagagc gcacgaggga | 2220 |
| gcttccaggg ggaaacgcct ggtatcttta tagtcctgtc gggtttcgcc acctctgact | 2280 |
| tgagcgtcga ttttttgtgat gctcgtcagg ggggcggagc ctatgaaaaa cgccagcaa | 2340 |
| cgcggccttt ttacgttcc tggccttttg ctggccttttt gctcacatgt tctttcctgc | 2400 |
| gttatcccct gattctgtgg ataaccgtat taccgccttt gagtgagctg ataccgctcg | 2460 |
| ccgcagccga acgaccgagc gcagcgagtc agtgagcgag gaagcggaag agcgcccaat | 2520 |
| acgcaaaccg cctctccccg cgcgttggcc gattcattaa tgcaggttaa cctggcttat | 2580 |
| cgaaattaat acgactcact atagggagac cggcagatct gtccctctct gcgcgctcgc | 2640 |
| tcgctcactg aggccgcccg ggcaaagccc gggcgtcggg cgacctttgg tcgcccggcc | 2700 |
| tcagtgagcg agcgagcgcg cagagaggga gtggccaact ccatcactag gggttccttg | 2760 |
| tagttaatga ttaacccgcc atgctactta tctacaattc gcccttcgga cgcgtggctt | 2820 |
| cgaactaggc aattgcatga agaatctgct tagggttagg cgttttgcgc tgcttcgcga | 2880 |
| tgtacgggcc agatatacgc gttgacattg attattgact agttattaat agtaatcaat | 2940 |
| tacgggtca ttagttcata gcccatatat ggagttccgc gttacataac ttacggtaaa | 3000 |
| tggcccgcct ggctgaccgc ccaacgaccc ccgcccattg acgtcaataa tgacgtatgt | 3060 |
| tcccatagta acgccaatag ggactttcca ttgacgtcaa tgggtggagt atttacggta | 3120 |
| aactgcccac ttggcagtac atcaagtgta tcatatgcca agtacgcccc ctattgacgt | 3180 |
| caatgacggt aaatggcccg cctggcatta tgcccagtac atgaccttat gggactttcc | 3240 |
| tacttggcag tacatctacg tattagtcat cgctattacc atggtgatgc ggttttggca | 3300 |
| gtacatcaat gggcgtggat agcggtttga ctcacgggga tttccaagtc tccaccccat | 3360 |
| tgacgtcaat gggagtttgt tttggcacca aaatcaacgg gactttccaa aatgtcgtaa | 3420 |
| caactccgcc ccattgacgc aaatgggcgg taggcgtgta cggtgggagg tctatataag | 3480 |
| cagagctctc tggctaacta gagaacccac tgcttactgg cttatcgaaa ttaatacgac | 3540 |
| tcactatagg gagacccaag ctggctagcg tttaaactta gcttcctgg ctatggggga | 3600 |
| gccggctggg gttgccggca ccatggagtc acctttttagc ccgggactct ttcacaggct | 3660 |
| ggatgaagat tgggattctg ctctctttgc tgaactcggt tatttcacag acactgatga | 3720 |
| gctgcaattg gaagcagcaa atgagacgta tgaaaacaat tttgataatc ttgattttga | 3780 |
| tttggatttg atgccttggg agtcagacat ttggacatc aacaaccaaa tctgtacagt | 3840 |
| taaagatatt aaggcagaac ctcagccact ttctccagcc tcctcaagtt attcagtctc | 3900 |

```
gtctcctcgg tcagtggact cttattcttc aactcagcat gttcctgagg agttggattt    3960
gtcttctagt tctcagatgt ctcccctttc cttatatggt gaaaactcta atagtctctc    4020
ttcagcggag ccactgaagg aagataagcc tgtcactggt cctaggaaca agactgaaaa    4080
tggactgact ccaaagaaaa aaattcaggt gaattcaaaa ccttcaattc agcccaagcc    4140
tttattgctt ccagcagcac ccaagactca acaaactcc agtgttccag caaaaccat     4200 cattattcag acagtaccaa cgcttatgcc attggcaaag cagcaaccaa ttatcagttt    4260
acaacctgca cccactaaag gccagacggt tttgctgtct cagcctactg tggtacaact    4320
tcaagcacct ggagttctgc cctctgctca gccagtcctt gctgttgctg ggggagtcac    4380
acagctccct aatcacgtgg tgaatgtggt accagcccct tcagcgaata gcccagtgaa    4440
tggaaaactt tccgtgacta aacctgtcct acaaagtacc atgagaaatg tcggttcaga    4500
tattgctgtg ctaaggagac agcaacgtat gataaaaaat cgagaatccg cttgtcagtc    4560
tcgcaagaag aagaaagaat atatgctagg gttagaggcg agattaaagg ctgccctctc    4620
agaaaacgag caactgaaga aagaaatgg aacactgaag cggcagctgg atgaagttgt    4680
gtcagagaac cagaggcttc taggtggtgg tggttcgggt ggtggtggtt cgggtggtgg    4740
tggttcggcg gcggcgatgg tggtggtggc agccgcgccg aacccggccg acgggacccc    4800
taaagttctg cttctgtcgg ggcagcccgc ctccgccgcc ggagcccgg ccggccaggc     4860 cctgccgctc atggtgccag cccagagagg ggccagcccg gaggcagcga gcgggggggct    4920 gccccaggcg cgcaagcgac agcgcctcac gcacctgagc cccgaggaga aggcgctgag    4980
gaggaaactg aaaacagag tagcagctca gactgccaga gatcgaaaga aggctcgaat    5040
gagtgagctg gaacagcaag tggtagattt agaagaagag aaccaaaaac ttttgctaga    5100
aaatcagctt ttacgagaga aaactcatgg ccttgtagtt gagaaccagg agttaagaca    5160
gcgcttgggg atggatgccc tggttgctga gaggaggcg gaagccaagg ggaatgaagt    5220
gaggccagtg gccgggtctg ctgagtccgc agcaggtgca ggcccagttg tcacccctcc    5280
agaacatctc cccatggatt ctggcggtat tgactcttca gattcagagt ctgatatcct    5340
gttgggcatt ctggacaact tggacccagt catgttcttc aaatgccctt ccccagagcc    5400
tgccagcctg gaggagctcc cagaggtcta cccagaagga cccagttcct taccagcctc    5460
cctttctctg tcagtgggga cgtcatcagc caagctggaa gccattaatg aactaattcg    5520
ttttgaccac atatatacca agccctagt cttagagata ccctctgaga cagagagcca    5580
agctaatgtg gtagtgaaaa tcgaggaagc acctctcagc ccctcagaga atgatcaccc    5640
tgaattcatt gtctcagtga aggaagaacc tgtagaagat gacctcgttc cggagctggg    5700
tatctcaaat ctgctttcat ccagccactg cccaaagcca tcttcctgcc tactggatgc    5760
ttacagtgac tgtggatacg ggggttccct ttccccattc agtgacatgt cctctctgct    5820
tggtgtaaac cattcttggg aggacacttt tgccaatgaa ctctttcccc agctgattag    5880
tgtctaccca tacgatgttc cagattacgc aatgtaaaga gccacataac actgggcccc    5940
tttccctgac catcacattg cctagaggat agcataggcc tgaagggcga attccagcac    6000
actggcggcc gttactagag ggcccgttta aacccgctga tcacctcgac tgtgccttct    6060
agttgccagc catctgttgt ttgcccctcc ccgtgcctt ccttgaccct ggaaggtgcc      6120
actcccactg tcctttccta ataaaatgag gaaattgcat cgcattgtct gagtaggtgt    6180
cattctattc tggggggtgg ggtggggcag gacagcaagg gggaggattg ggaagacaat    6240
```

| agcaggcatg | cctgcagcgg | tccggtcgac | tctagaggat | ccgaaaaaac | ctcccacacc | 6300 |
| tcccctgaa | cctgaaacat | aaatgaatg | caattgttgt | tgttaacttg | tttattgcag | 6360 |
| cttataatgg | ttacaaataa | agcaatagca | tcacaaattt | cacaaataaa | gcatttttt | 6420 |
| cactgcattc | tagttgtggt | ttgtccaaac | tcatcaatgt | atcttatcat | gtctggatcc | 6480 |
| ccgcggtggc | ggccgcacta | gtcccgggtt | aattaagcta | gcagatcttg | atcacctagg | 6540 |
| cgtacgattt | ggccgcttta | catggtggcg | accggggatc | tctagtacc | aagctaattc | 6600 |
| ctcacgacac | ctgaaatgga | agaaaaaaac | tttgaaccac | tgtctgaggc | ttgagaatga | 6660 |
| accaagatcc | aaactcaaaa | agggcaaatt | ccaaggagaa | ttacatcaag | tgccaagctg | 6720 |
| gcctaacttc | agtctccacc | cactcagtgt | ggggaaactc | catcgcataa | aaccccctcc | 6780 |
| cccaacctaa | agacgacgta | ctccaaaagc | tcgagaacta | atcgaggtgc | ctggacggcg | 6840 |
| cccggtactc | cgtggagtca | catgaagcga | cggctgagga | cggaaaggcc | cttttccttt | 6900 |
| gtgtgggtga | ctcacccgcc | cgctctcccg | agcgccgcgt | cctccatttt | gagctccctg | 6960 |
| cagcagggcc | gggaagcggc | catctttccg | ctcacgcaac | tggtgccgac | cgggccagcc | 7020 |
| ttgccgccca | gggcggggcg | atacacggcg | gcgcgaggcc | aggcaccaga | gcaggccggc | 7080 |
| cagcttgaga | ctacccccgt | ccgattctcg | gtggccgcgc | tcgcaggccc | cgcctcgccg | 7140 |
| aacatgtgcg | ctgggacgca | cgggccccgt | cgccgcccgc | ggcccaaaa | accgaaatac | 7200 |
| cagtgtgcag | atcttggccc | gcatttacaa | gactatcttg | ccagaaaaaa | agcgtcgcag | 7260 |
| caggtcatca | aaaattttaa | atggctagag | acttatcgaa | agcagcgaga | caggcgcgaa | 7320 |
| ggtgccacca | gattcgcacg | cggcggcccc | agcgcccagg | ccaggcctca | actcaagcac | 7380 |
| gaggcgaagg | ggctccttaa | gcgcaaggcc | tcgaactctc | ccacccactt | ccaacccgaa | 7440 |
| gctcgggatc | aagaatcacg | tactgcagcc | aggtggaagt | aattcaaggc | acgcaagggc | 7500 |
| cataacccgt | aaagaggcca | ggcccgcggg | aaccacacac | ggcacttacc | tgtgttctgg | 7560 |
| cggcaaaccc | gttgcgaaaa | agaacgttca | cggcgactac | tgcacttata | tacgttctc | 7620 |
| ccccacccctc | gggaaaaagg | cggagccagt | acacgacatc | actttcccag | tttaccccgc | 7680 |
| gccaccttct | ctaggcaccg | g | | | | 7701 |

<210> SEQ ID NO 3
<211> LENGTH: 7719
<212> TYPE: DNA
<213> ORGANISM: Artificial Sequence
<220> FEATURE:
<223> OTHER INFORMATION: pAAV_ATF6f-L4H4-XBP1s-HA

<400> SEQUENCE: 3

| ggcggatcca | attgcctagg | cccaagggcg | aattgtcacg | actccacccc | tccaggaacc | 60 |
| cctagtgatg | gagttggcca | ctccctctct | gcgcgctcgc | tcgctcactg | aggccgcccg | 120 |
| ggcaaagccc | gggcgtcggg | cgacctttgg | tcgcccggcc | tcagtgagcg | agcgagcgcg | 180 |
| cagagaggga | gtgccagaga | tctgatatca | tcgatgaatt | caagcttcag | ctgctcgagt | 240 |
| tctatagtgt | cacctaaatc | gtatgtgtat | gatacataag | gttatgtatt | aattgtagcc | 300 |
| gcgttctaac | gacaatatgt | ccatatggtg | cactctcagt | acaatctgct | ctgatgccgc | 360 |
| atagttaagc | cagccccgac | acccgccaac | acccgctgac | gcgccctgac | gggcttgtct | 420 |
| gctcccggca | tccgcttaca | gacaagctgt | gaccgtctcc | gggagctgca | tgtgtcagag | 480 |
| gttttcaccg | tcatcaccga | aacgcgcgag | acgaaagggc | ctcgtgatac | gcctattttt | 540 |
| ataggttaat | gtcatgataa | taatggtttc | ttagacgtca | ggtggcactt | ttcggggaaa | 600 |

```
tgtgcgcgga accectattt gtttatttt  ctaaatacat tcaaatatgt atccgctcat    660
gagacaataa ccctgataaa tgcttcaata atattgaaaa aggaagagta tgagtattca    720
acatttccgt gtcgcccttta ttcccttttt tgcggcattt tgccttcctg ttttgctca    780 cccagaaacg ctggtgaaag taaaagatgc tgaagatcag ttgggtgcac gagtgggtta    840
catcgaactg gatctcaaca gcggtaagat ccttgagagt tttcgccccg aagaacgttt    900
tccaatgatg agcacttta aagttctgct atgtggcgcg gtattatccc gtattgacgc    960
cgggcaagag caactcggtc gccgcataca ctattctcag aatgacttgg ttgagtactc    1020
accagtcaca gaaaagcatc ttacggatgg catgacagta agagaattat gcagtgctgc    1080
cataaccatg agtgataaca ctgcggccaa cttacttctg acaacgatcg gaggaccgaa    1140
ggagctaacc gcttttttgc acaacatggg ggatcatgta actcgccttg atcgttggga    1200
accggagctg aatgaagcca taccaaacga cgagcgtgac accacgatgc ctgtagcaat    1260
ggcaacaacg ttgcgcaaac tattaactgg cgaactactt actctagctt cccggcaaca    1320
attaatagac tggatggagg cggataaagt tgcaggacca cttctgcgct cggcccttcc    1380
ggctggctgg tttattgctg ataaatctgg agccggtgag cgtgggtctc gcggtatcat    1440
tgcagcactg gggccagatg gtaagccctc ccgtatcgta gttatctaca cgacggggag    1500
tcaggcaact atggatgaac gaaatagaca gatcgctgag ataggtgcct cactgattaa    1560
gcattggtaa ctgtcagacc aagtttactc atatatactt tagattgatt taaaacttca    1620
tttttaattt aaaaggatct aggtgaagat ccttttttgat aatctcatga ccaaaatccc    1680
ttaacgtgag ttttcgttcc actgagcgtc agaccccgta gaaaagatca aaggatcttc    1740
ttgagatcct ttttttctgc gcgtaatctg ctgcttgcaa acaaaaaaac caccgctacc    1800
agcggtggtt tgtttgccgg atcaagagct accaactctt tttccgaagg taactggctt    1860
cagcagagcg cagataccaa atactgtcct tctagtgtag ccgtagttag gccaccactt    1920
caagaactct gtagcaccgc ctacatacct cgctctgcta atcctgttac cagtggctgc    1980
tgccagtggc gataagtcgt gtcttaccgg gttggactca agacgatagt taccggataa    2040
ggcgcagcgg tcgggctgaa cggggggttc gtgcacacag cccagcttgg agcgaacgac    2100
ctacaccgaa ctgagatacc tacagcgtga gcattgagaa agcgccacgc ttcccgaagg    2160
gagaaaggcg gacaggtatc cggtaagcgg cagggtcgga acaggagagc gcacgaggga    2220
gcttccaggg ggaaacgcct ggtatcttta tagtcctgtc gggtttcgcc acctctgact    2280
tgagcgtcga tttttgtgat gctcgtcagg ggggcggagc ctatggaaaa acgccagcaa    2340
cgcggccttt ttacggttcc tggccttttg ctggccttt gctcacatgt tctttcctgc    2400
gttatcccct gattctgtgg ataaccgtat taccgccttt gagtgagctg ataccgctcg    2460
ccgcagccga acgaccgagc gcagcgagtc agtgagcgag gaagcggaag agcgcccaat    2520
acgcaaaccg cctctccccg cgcgttggcc gattcattaa tgcaggttaa cctggcttat    2580
cgaaattaat acgactcact atagggagac cggcagatct gtccctctct gcgcgctcgc    2640
tcgctcactg aggccgcccg ggcaaagccc gggcgtcggg cgacctttgg tcgcccggcc    2700
tcagtgagcg agcgagcgcg cagagaggga gtggccaact ccatcactag gggttccttg    2760
tagttaatga ttaacccgcc atgctactta tctacaattc gcccttcgga cgcgtggctt    2820
cgaactagga aattgcatga agaatctgct tagggttagg cgttttgcgc tgcttcgcga    2880
tgtacgggcc agatatacgc gttgacattg attattgact agttattaat agtaatcaat    2940
```

```
tacggggtca ttagttcata gcccatatat ggagttccgc gttacataac ttacggtaaa    3000
tggcccgcct ggctgaccgc ccaacgaccc ccgcccattg acgtcaataa tgacgtatgt    3060
tcccatagta acgccaatag ggactttcca ttgacgtcaa tgggtggagt atttacggta    3120
aactgcccac ttggcagtac atcaagtgta tcatatgcca agtacgcccc ctattgacgt    3180
caatgacggt aaatggcccg cctggcatta tgcccagtac atgaccttat gggactttcc    3240
tacttggcag tacatctacg tattagtcat cgctattacc atggtgatgc ggttttggca    3300
gtacatcaat gggcgtggat agcggtttga ctcacgggga tttccaagtc tccaccccat    3360
tgacgtcaat gggagtttgt tttggcacca aaatcaacgg gactttccaa aatgtcgtaa    3420
caactccgcc ccattgacgc aaatgggcgg taggcgtgta cggtgggagg tctatataag    3480
cagagctctc tggctaacta gagaacccac tgcttactgg cttatcgaaa ttaatacgac    3540
tcactatagg gagacccaag ctggctagcg tttaaactta agcttcctgg ctatggggga    3600
gccggctggg gttgccggca ccatggagtc acctttta gc ccgggactct tcacaggct    3660 ggatgaagat tgggattctg ctctctttgc tgaactcggt tatttcacag acactgatga    3720
gctgcaattg gaagcagcaa atgagacgta tgaaaacaat tttgataatc ttgattttga    3780
tttggatttg atgccttggg agtcagacat ttgggacatc aacaaccaaa tctgtacagt    3840
taaagatatt aaggcagaac ctcagccact ttctccagcc tcctcaagtt attcagtctc    3900
gtctcctcgg tcagtggact cttattcttc aactcagcat gttcctgagg agttggattt    3960
gtcttctagt tctcagatgt ctccccttc cttatatggt gaaaactcta atagtctctc    4020
ttcagcggag ccactgaagg aagataagcc tgtcactggt cctaggaaca agactgaaaa    4080
tggactgact ccaaagaaaa aaattcaggt gaattcaaaa ccttcaattc agcccaagcc    4140
tttattgctt ccagcagcac ccaagactca aacaaactcc agtgttccag caaaaaccat    4200
cattattcag acagtaccaa cgcttatgcc attggcaaag cagcaaccaa ttatcagttt    4260
acaacctgca cccactaaag gccagacggt tttgctgtct cagcctactg tggtacaact    4320
tcaagcacct ggagttctgc cctctgctca gccagtcctt gctgttgctg ggggagtcac    4380
acagctccca aatcacgtgg tgaatgtggt accagcccct tcagcgaata gcccagtgaa    4440
tggaaaactt ccgtgactaaa acctgtcct acaaagtacc atgagaaatg tcggttcaga    4500
tattgctgtg ctaaggagac agcaacgtat gataaaaaat cgagaatccg cttgtcagtc    4560
tcgcaagaag aagaaagaat atatgctagg gttagaggcg agattaaagg ctgccctctc    4620
agaaaacgag caactgaaga aagaaaatgg aacactgaag cggcagctgg atgaagttgt    4680
gtcagagaac cagaggcttc tagcggaagc ggcggcgaaa gaagcggcgg cgaaagaagc    4740
ggcggcgaaa gaagcggcgg cgaaagcggc ggcgatggtg gtggtggcag ccgcgccgaa    4800
cccggccgac gggaccccta agttctgct tctgtcgggg cagcccgcct ccgccgccgg    4860
agccccggcc ggccaggccc tgccgctcat ggtgccagcc cagagagggg ccagcccgga    4920
ggcagcgagc gggggctgc cccaggcgcg caagcgacag cgcctcacgc acctgagccc    4980
cgaggagaag gcgctgagga ggaaactgaa aaacagagta gcagctcaga ctgccagaga    5040
tcgaaagaag gctcgaatga gtgagctgga acagcaagtg gtagatttag aagaagagaa    5100
ccaaaaactt ttgctagaaa atcagctttt acgagagaaa actcatggcc ttgtagttga    5160
gaaccaggag ttaagacagc gctttgggat ggatgccctg gttgctgaag aggaggcgga    5220
agccaagggg aatgaagtga ggccagtggc cgggtctgct gagtccgcag caggtgcagg    5280
cccagttgtc acccctccag aacatctccc catggattct ggcggtattg actcttcaga    5340
```

```
ttcagagtct gatatcctgt tgggcattct ggacaacttg gacccagtca tgttcttcaa    5400
atgcccttcc ccagagcctg ccagcctgga ggagctccca gaggtctacc cagaaggacc    5460
cagttcctta ccagcctccc tttctctgtc agtggggacg tcatcagcca agctggaagc    5520
cattaatgaa ctaattcgtt ttgaccacat atataccaag cccctagtct tagagatacc    5580
ctctgagaca gagagccaag ctaatgtggt agtgaaaatc gaggaagcac ctctcagccc    5640
ctcagagaat gatcaccctg aattcattgt ctcagtgaag gaagaacctg tagaagatga    5700
cctcgttccg gagctgggta tctcaaatct gctttcatcc agccactgcc aaagccatc     5760
ttcctgccta ctggatgctt acagtgactg tggatacggg ggttccctt ccccattcag     5820
tgacatgtcc tctctgcttg gtgtaaacca ttcttgggag gacactttg ccaatgaact     5880
ctttccccag ctgattagtg tctacccata cgatgttcca gattacgcaa tgtaaagagc    5940
cacataacac tgggccccct tccctgacca tcacattgcc tagaggatag cataggcctg    6000
aagggcgaat tccagcacac tggcggccgt tactagaggg cccgtttaaa cccgctgatc    6060
acctcgactg tgccttctag ttgccagcca tctgttgttt gcccctcccc cgtgccttcc    6120
ttgaccctgg aaggtccac tcccactgtc ctttcctaat aaaatgagga aattgcatcg     6180
cattgtctga gtaggtgtca ttctattctg ggggtgggg tggggcagga cagcaagggg    6240
gaggattggg aagacaatag caggcatgcc tgcagcggtc cggtcgactc tagaggatcc    6300
gaaaaaacct cccacacctc ccctgaacc tgaaacataa aatgaatgca attgttgttg     6360
ttaacttgtt tattgcagct tataatggtt acaaataaag caatagcatc acaaatttca    6420
caaataaagc attttttca ctgcattcta gttgtggttt gtccaaactc atcaatgtat     6480
cttatcatgt ctggatcccc gcggtggcgg ccgcactagt cccgggttaa ttaagctagc    6540
agatcttgat cacctaggcg tacgatttgg ccgctttaca tggtggcgac cggggatcct    6600
ctagtaccaa gctaattcct cacgacacct gaaatggaag aaaaaaactt tgaaccactg    6660
tctgaggctt gagaatgaac caagatccaa actcaaaaag ggcaaattcc aaggagaatt    6720
acatcaagtg ccaagctggc ctaacttcag tctccaccca ctcagtgtgg ggaaactcca    6780
tcgcataaaa ccctcccccc caacctaaag acgacgtact ccaaaagctc gagaactaat    6840
cgaggtgcct ggacggcgcc cggtactccg tggagtcaca tgaagcgacg gctgaggacg    6900
gaaaggcccc tttcctttgt gtgggtgact cacccgcccg ctctcccgag cgccgcgtcc    6960
tccattttga gctccctgca gcagggccgg gaagcggcca tctttccgct cacgcaactg    7020
gtgccgaccg ggccagcctt gccgcccagg gcggggcgat acacggcggc gcgaggccag    7080
gcaccagagc aggccggcca gcttgagact accccgtcc gattctcggt ggccgcgctc     7140
gcaggccccg cctcgccgaa catgtgcgct gggacgcacg gccccgtcg ccgcccgcgg     7200
ccccaaaaac cgaaatacca gtgtgcagat cttggcccgc atttacaaga ctatcttgcc    7260
agaaaaaaag cgtcgcagca ggtcatcaaa aatttttaaat ggctagagac ttatcgaaag    7320
cagcgagaca ggcgcgaagg tgccaccaga ttcgcacgcg gcggcccag cgcccaggcc     7380
aggcctcaac tcaagcacga ggcgaagggg ctccttaagc gcaaggcctc gaactctccc    7440
acccacttcc aacccgaagc tcgggatcaa gaatcacgta ctgcagccag gtggaagtaa    7500
ttcaaggcac gcaagggcca taacccgtaa agaggccagg cccgcgggaa ccacacacgg    7560
cacttacctg tgttctggcg gcaaacccgt tgcgaaaaag aacgttcacg gcgactactg    7620
cacttatata cggttctccc ccaccctcgg gaaaaaggcg gagccagtac acgacatcac    7680
```

```
tttcccagtt taccccgcgc caccttctct aggcaccgg                    7719
```

<210> SEQ ID NO 4
<211> LENGTH: 7719
<212> TYPE: DNA
<213> ORGANISM: Artificial Sequence
<220> FEATURE:
<223> OTHER INFORMATION: pAAV_XBP1s-L4H4-ATF6f-HA

<400> SEQUENCE: 4

```
ggcggatcca attgcctagg cccaagggcg aattgtcacg actccacccc tccaggaacc      60
cctagtgatg gagttggcca ctccctctct gcgcgctcgc tcgctcactg aggccgcccg     120
ggcaaagccc gggcgtcggg cgacctttgg tcgcccggcc tcagtgagcg agcgagcgcg     180
cagagaggga gtggcccaga tctgatatca tcgatgaatt caagcttcag ctgctcgagt     240
tctatagtgt cacctaaatc gtatgtgtat gatacataag gttatgtatt aattgtagcc     300
gcgttctaac gacaatatgt ccatatggtg cactctcagt acaatctgct ctgatgccgc     360
atagttaagc cagccccgac acccgccaac cccgctgacg cgccctgac gggcttgtct     420
gctcccggca tccgcttaca caagctgt gaccgtctcc gggagctgca tgtgtcagag     480
gttttcaccg tcatcaccga aacgcgcgag acgaaagggc ctcgtgatac gcctattttt     540
ataggttaat gtcatgataa taatggtttc ttagacgtca ggtggcactt ttcggggaaa     600
tgtgcgcgga acccctattt gtttattttt ctaaatacat tcaaatatgt atccgctcat     660
gagacaataa ccctgataaa tgcttcaata atattgaaaa aggaagagta tgagtattca     720
acatttccgt gtcgccctta ttcccttttt tgcggcattt tgccttcctg tttttgctca     780
cccagaaacg ctggtgaaag taaaagatgc tgaagatcag ttgggtgcac gagtgggtta     840
catcgaactg gatctcaaca gcggtaagat ccttgagagt tttcgccccg aagaacgttt     900
tccaatgatg agcactttta agttctgct atgtggcgcg gtattatccc gtattgacgc     960
cgggcaagag caactcggtc gccgcataca ctattctcag aatgacttgg ttgagtactc    1020
accagtcaca gaaaagcatc ttacggatgg catgacagta agagaattat gcagtgctgc    1080
cataaccatg agtgataaca ctgcggccaa cttacttctg acaacgatcg gaggaccgaa    1140
ggagctaacc gcttttttgc acaacatggg ggatcatgta actcgccttg atcgttggga    1200
accggagctg aatgaagcca taccaaacga cgagcgtgac accacgatgc ctgtagcaat    1260
ggcaacaacg ttgcgcaaac tattaactgg cgaactactt actctagctt cccggcaaca    1320
attaatagac tggatggagg cggataaagt tgcaggacca cttctgcgct cggcccttcc    1380
ggctggctgg tttattgctg ataaatctgg agccggtgag cgtgggtctc gcggtatcat    1440
tgcagcactg gggccagatg gtaagccctc ccgtatcgta gttatctaca cgacggggag    1500
tcaggcaact atggatgaac gaaatagaca gatcgctgag ataggtgcct cactgattaa    1560
gcattggtaa ctgtcagacc aagtttactc atatatactt tagattgatt taaaacttca    1620
tttttaattt aaaaggatct aggtgaagat cctttttgat aatctcatga ccaaaatccc    1680
ttaacgtgag ttttcgttcc actgagcgtc agaccccgta gaaaagatca aggatcttc    1740
ttgagatcct ttttttctgc gcgtaatctg ctgcttgcaa acaaaaaaac caccgctacc    1800
agcggtggtt tgtttgccgg atcaagagct accaactctt tttccgaagg taactggctt    1860
cagcagagcg cagataccaa atactgtcct tctagtgtag ccgtagttag gccaccactt    1920
caagaactct gtagcaccgc ctacatacct cgctctgcta atcctgttac cagtggctgc    1980
tgccagtggc gataagtcgt gtcttaccgg gttggactca agacgatagt taccggataa    2040
```

```
ggcgcagcgg tcgggctgaa cgggggttc gtgcacacag cccagcttgg agcgaacgac    2100
ctacaccgaa ctgagatacc tacagcgtga gcattgagaa agcgccacgc ttcccgaagg    2160
gagaaaggcg gacaggtatc cggtaagcgg cagggtcgga acaggagagc gcacgaggga    2220
gcttccaggg ggaaacgcct ggtatcttta tagtcctgtc gggtttcgcc acctctgact    2280
tgagcgtcga ttttgtgat gctcgtcagg ggggcggagc ctatggaaaa acgccagcaa     2340
cgcggccttt ttacggttcc tggccttttg ctggccttt gctcacatgt tctttcctgc    2400
gttatcccct gattctgtgg ataaccgtat taccgccttt gagtgagctg ataccgctcg    2460
ccgcagccga acgaccgagc gcagcgagtc agtgagcgag gaagcggaag agcgcccaat    2520
acgcaaaccg cctctccccg cgcgttggcc gattcattaa tgcaggttaa cctggcttat    2580
cgaaattaat acgactcact ataggggagac cggcagatct gtccctctct gcgcgctcgc    2640
tcgctcactg aggccgcccg ggcaaagccc gggcgtcggg cgacctttgg tcgcccggcc    2700
tcagtgagcg agcgagcgcg cagagaggga gtggccaact ccatcactag ggttccttg    2760 tagttaatga ttaacccgcc atgctactta tctacaattc gcccttcgga cgcgtggctt    2820
cgaactaggc aattgcatga agaatctgct tagggttagg cgttttgcgc tgcttcgcga    2880
tgtacgggcc agatatacgc gttgacattg attattgact agttattaat agtaatcaat    2940 tacgggtca ttagttcata gcccatatat ggagttccgc gttacataac ttacggtaaa     3000
tggcccgcct ggctgaccgc ccaacgaccc ccgcccattg acgtcaataa tgacgtatgt    3060
tcccatagta acgccaatag ggactttcca ttgacgtcaa tgggtggagt atttacggta    3120
aactgcccac ttggcagtac atcaagtgta tcatatgcca agtacgcccc ctattgacgt    3180
caatgacggt aaatggcccg cctggcatta tgcccagtac atgaccttat gggactttcc    3240
tacttggcag tacatctacg tattagtcat cgctattacc atggtgatgc ggttttggca    3300
gtacatcaat gggcgtggat agcggtttga ctcacgggga tttccaagtc tccaccccat    3360
tgacgtcaat gggagtttgt tttggcacca aaatcaacgg gactttccaa aatgtcgtaa    3420
caactccgcc ccattgacgc aaatgggcgg taggcgtgta cggtgggagg tctatataag    3480
cagagctctc tggctaacta gagaacccac tgcttactgg cttatcgaaa ttaatacgac    3540
tcactatagg gagacccaag ctggctagcg tttaaactta agcttcctgg ctatggtggt    3600
ggtggcagcc gcgccgaacc cggccgacgg gaccoctaaa gttctgcttc tgtcggggca    3660
gcccgcctcc gccgccggag ccccggccgg ccaggccctg ccgctcatgg tgccagccca    3720
gagaggggcc agcccggagg cagcgagcgg ggggctgccc caggcgcgca agcgacagcg    3780
cctcacgcac ctgagccccg aggagaaggc gctgaggagg aaactgaaaa acagagtagc    3840
agctcagact gccagagatc gaaagaaggc tcgaatgagt gagctggaac agcaagtggt    3900
agatttagaa gaagagaacc aaaaactttt gctagaaaat cagcttttac gagagaaaac    3960
tcatggcctt gtagttgaga accaggagtt aagacagcgc ttggggatgg atgccctggt    4020
tgctgaagag gaggcggaag ccaagggaa tgaagtgagg ccagtggccg ggtctgctga    4080
gtccgcagca ggtgcaggcc cagttgtcac ccctccagaa catctcccca tggattctgg    4140
cggtattgac tcttcagatt cagagtctga tatcctgttg ggcattctgg acaacttgga    4200
cccagtcatg ttcttcaaat gcccttcccc agagcctgcc agcctggagg agctcccaga    4260
ggtctaccca gaaggaccca gttccttacc agcctccctt tctctgtcag tggggacgtc    4320
atcagccaag ctggaagcca ttaatgaact aattcgtttt gaccacatat ataccaagcc    4380
```

```
cctagtctta gagatacect ctgagacaga gagccaagct aatgtggtag tgaaaatcga    4440
ggaagcacct ctcagcccct cagagaatga tcaccctgaa ttcattgtct cagtgaagga    4500
agaacctgta gaagatgacc tcgttccgga gctgggtatc tcaaatctgc tttcatccag    4560
ccactgccca aagccatctt cctgcctact ggatgcttac agtgactgtg gatacggggg    4620
ttccctttcc ccattcagtg acatgtcctc tctgcttggt gtaaaccatt cttgggagga    4680
cacttttgcc aatgaactct ttccccagct gattagtgtc ctagcggaag cggcggcgaa    4740
agaagcggcg gcgaaagaag cggcggcgaa agaagcggcg gcgaaagcgg cggcgatggg    4800
ggagccggct ggggttgccg gcaccatgga gtcacctttt agcccgggac tctttcacag    4860
gctggatgaa gattgggatt ctgctctctt tgctgaactc ggttatttca cagacactga    4920
tgagctgcaa ttggaagcag caaatgagac gtatgaaaac aattttgata atcttgattt    4980
tgatttggat ttgatgcctt gggagtcaga catttgggac atcaacaacc aaatctgtac    5040
agttaaagat attaaggcag aacctcagcc actttctcca gcctcctcaa gttattcagt    5100
ctcgtctcct cggtcagtgg actcttattc ttcaactcag catgttcctg aggagttgga    5160
tttgtcttct agttctcaga tgtctcccct ttccttatat ggtgaaaact ctaatagtct    5220
ctcttcagcg gagccactga aggaagataa gcctgtcact ggtcctagga acaagactga    5280
aaatggactg actccaaaga aaaaaattca ggtgaattca aaaccttcaa ttcagcccaa    5340
gcctttattg cttccagcag cacccaagac tcaaacaaac tccagtgttc cagcaaaaac    5400
catcattatt cagacagtac caacgcttat gccattggca aagcagcaac caattatcag    5460
tttacaacct gcacccacta aaggccagac ggttttgctg tctcagccta ctgtggtaca    5520
acttcaagca cctggagttc tgccctctgc tcagccagtc cttgctgttg ctggggagt     5580
cacacagctc cctaatcacg tggtaatgt ggtaccagcc ccttcagcga atagcccagt     5640
gaatggaaaa ctttccgtga ctaaacctgt cctacaaagt accatgagaa atgtcggttc    5700
agatattgct gtgctaagga gacagcaacg tatgataaaa aatcgagaat ccgcttgtca    5760
gtctcgcaag aagaagaaag aatatatgct agggttagag gcgagattaa aggctgccct    5820
ctcagaaaac gagcaactga agaaagaaaa tggaacactg aagcggcagc tggatgaagt    5880
tgtgtcagag aaccagaggc tttacccata cgatgttcca gattacgcaa tgtaaagagc    5940
cacataaacac tgggcccctt tccctgacca tcacattgcc tagaggatag cataggcctg    6000
aagggcgaat tccagcacac tggcggccgt tactagaggg cccgtttaaa cccgctgatc    6060
acctcgactg tgccttctag ttgccagcca tctgttgttt gccctcccc cgtgccttcc     6120
ttgaccctgg aaggtgccac tcccactgtc ctttcctaat aaaatgagga aattgcatcg    6180
cattgtctga gtaggtgtca ttctattctg ggggtgggg tggggcagga cagcaagggg     6240
gaggattggg aagacaatag caggcatgcc tgcagcggtc cggtcgactc tagaggatcc    6300
gaaaaacct cccacacctc ccctgaacc tgaaacataa aatgaatgca attgttgttg      6360
ttaacttgtt tattgcagct tataatggtt acaaataaag caatagcatc acaaatttca    6420
caaataaagc attttttca ctgcattcta gttgtggttt gtccaaactc atcaatgtat     6480
cttatcatgt ctggatcccc gcggtggcgg ccgcactagt cccgggttaa ttaagctagc    6540
agatcttgat caactaggcg tacgatttgg ccgctttaca tggtggcgac cggggatcct    6600
ctagtaccaa gctaattcct cacgacacct gaaatggaag aaaaaaactt gaaccactg     6660
tctgaggctt gagaatgaac caagatccaa actcaaaaag gcaaattcc aaggagaatt     6720
acatcaagtg ccaagctggc ctaacttcag tctccaccca ctcagtgtgg ggaaactcca    6780
```

| | |
|---|---|
| tcgcataaaa cccctcccc caacctaaag acgacgtact ccaaaagctc gagaactaat | 6840 |
| cgaggtgcct ggacggcgcc cggtactccg tggagtcaca tgaagcgacg gctgaggacg | 6900 |
| gaaaggccct tttcctttgt gtgggtgact cacccgcccg ctctcccgag cgccgcgtcc | 6960 |
| tccattttga gctccctgca gcagggccgg gaagcggcca tctttccgct cacgcaactg | 7020 |
| gtgccgaccg ggccagcctt gccgcccagg gcggggcgat acacggcggc gcgaggccag | 7080 |
| gcaccagagc aggccggcca gcttgagact accccgtcc gattctcggt ggccgcgctc | 7140 |
| gcaggccccg cctcgccgaa catgtgcgct gggacgcacg ggccccgtcg ccgcccgcgg | 7200 |
| ccccaaaaac cgaaatacca gtgtgcagat cttggcccgc atttacaaga ctatcttgcc | 7260 |
| agaaaaaaag cgtcgcagca ggtcatcaaa aattttaaat ggctagagac ttatcgaaag | 7320 |
| cagcgagaca ggcgcgaagg tgccaccaga ttcgacgcg gcggcccag cgcccaggcc | 7380 |
| aggcctcaac tcaagcacga ggcgaagggg ctccttaagc gcaaggcctc gaactctccc | 7440 |
| acccacttcc aacccgaagc tcgggatcaa gaatcacgta ctgcagccag gtggaagtaa | 7500 |
| ttcaaggcac gcaagggcca taacccgtaa agaggccagg cccgcgggaa ccacacacgg | 7560 |
| cacttacctg tgttctggcg gcaaacccgt tgcgaaaaag aacgttcacg gcgactactg | 7620 |
| cacttatata cggttctccc ccacccctcgg gaaaaaggcg gagccagtac acgacatcac | 7680 |
| tttcccagtt taccccgcgc caccttctct aggcaccgg | 7719 |

<210> SEQ ID NO 5
<211> LENGTH: 7809
<212> TYPE: DNA
<213> ORGANISM: Artificial Sequence
<220> FEATURE:
<223> OTHER INFORMATION: pAAV_XBP1s-LF-ATF6f-HA

<400> SEQUENCE: 5

| | |
|---|---|
| ggcggatcca attgcctagg cccaagggcg aattgtcacg actccacccc tccaggaacc | 60 |
| cctagtgatg gagttggcca ctccctctct gcgcgctcgc tcgctcactg aggccgcccg | 120 |
| ggcaaagccc gggcgtcggg cgaccttttgg tcgcccggcc tcagtgagcg agcgagcgcg | 180 |
| cagagaggga gtggcccaga tctgatatca tcgatgaatt caagcttcag ctgctcgagt | 240 |
| tctatagtgt cacctaaatc gtatgtgtat gatacataag gttatgtatt aattgtagcc | 300 |
| gcgttctaac gacaatatgt ccatatggtg cactctcagt acaatctgct ctgatgccgc | 360 |
| atagttaagc cagccccgac acccgccaac acccgctgac gcgccctgac gggcttgtct | 420 |
| gctcccggca tccgcttaca gacaagctgt gaccgtctcc gggagctgca tgtgtcagag | 480 |
| gttttcaccg tcatcaccga aacgcgcgag acgaaagggc ctcgtgatac gcctattttt | 540 |
| ataggttaat gtcatgataa taatggtttc ttagacgtca ggtggcactt ttcggggaaa | 600 |
| tgtgcgcgga accctatttg tttattttc taaatacat tcaaatatgt atccgctcat | 660 |
| gagacaataa ccctgataaa tgcttcaata atattgaaaa aggaagagta tgagtattca | 720 |
| acatttccgt gtcgccctta ttccctttt tgcggcattt tgccttcctg ttttgctca | 780 |
| cccagaaacg ctggtgaaag taaaagatgc tgaagatcag ttgggtgcac gagtgggtta | 840 |
| catcgaactg gatctcaaca gcggtaagat ccttgagagt tttcgccccg aagaacgttt | 900 |
| tccaatgatg agcacttta aagttctgct atgtggcgcg gtattatccc gtattgacgc | 960 |
| cgggcaagag caactcggtc gccgcataca ctattctcag aatgacttgg ttgagtactc | 1020 |
| accagtcaca gaaaagcatc ttacggatgg catgacagta agagaattat gcagtgctgc | 1080 |

```
cataaccatg agtgataaca ctgcggccaa cttacttctg acaacgatcg gaggaccgaa    1140
ggagctaacc gctttttgc acaacatggg ggatcatgta actcgccttg atcgttggga     1200
accggagctg aatgaagcca taccaaacga cgagcgtgac accacgatgc ctgtagcaat    1260
ggcaacaacg ttgcgcaaac tattaactgg cgaactactt actctagctt cccggcaaca    1320
attaatagac tggatggagg cggataaagt tgcaggacca cttctgcgct cggcccttcc    1380
ggctggctgg tttattgctg ataaatctgg agccggtgag cgtgggtctc gcggtatcat    1440
tgcagcactg gggccagatg gtaagccctc ccgtatcgta gttatctaca cgacggggag    1500
tcaggcaact atggatgaac gaaatagaca gatcgctgag ataggtgcct cactgattaa    1560
gcattggtaa ctgtcagacc aagtttactc atatatactt tagattgatt taaaacttca    1620
tttttaattt aaaaggatct aggtgaagat cctttttgat aatctcatga ccaaaatccc    1680
ttaacgtgag ttttcgttcc actgagcgtc agaccccgta gaaaagatca aaggatcttc    1740
ttgagatcct ttttttctgc gcgtaatctg ctgcttgcaa acaaaaaaac caccgctacc    1800
agcggtggtt tgtttgccgg atcaagagct accaactctt tttccgaagg taactggctt    1860
cagcagagcg cagataccaa atactgtcct tctagtgtag ccgtagttag gccaccactt    1920
caagaactct gtagcaccgc ctacatacct cgctctgcta atcctgttac cagtggctgc    1980
tgccagtggc gataagtcgt gtcttaccgg gttggactca agacgatagt taccggataa    2040
ggcgcagcgg tcgggctgaa cggggggttc gtgcacacag cccagcttgg agcgaacgac    2100
ctacaccgaa ctgagatacc tacagcgtga gcattgagaa agcgccacgc ttcccgaagg    2160
gagaaaggcg gacaggtatc cggtaagcgg cagggtcgga acaggagagc gcacgaggga    2220
gcttccaggg ggaaacgcct ggtatcttta gtcctgtc gggtttcgcc acctctgact    2280
tgagcgtcga ttttttgtgat gctcgtcagg ggggcggagc ctatggaaaa acgccagcaa    2340
cgcggccttt ttacggttcc tggccttttg ctggccttt gctcacatgt tctttcctgc    2400
gttatcccct gattctgtgg ataaccgtat taccgccttt gagtgagctg ataccgctcg    2460
ccgcagccga acgaccgagc gcagcgagtc agtgagcgag gaagcggaag agcgcccaat    2520
acgcaaaccg cctctccccg cgcgttggcc gattcattaa tgcaggttaa cctggcttat    2580
cgaaattaat acgactcact atagggagac cggcagatct gtccctctct gcgcgctcgc    2640
tcgctcactg aggccgcccg ggcaaagccc gggcgtcggg cgacctttgg tcgcccggcc    2700
tcagtgagcg agcgagcgcg cagagaggga gtggccaact ccatcactag gggttccttg    2760
tagttaatga ttaacccgcc atgctactta tctacaattc gcccttcgga cgcgtggctt    2820
cgaactaggc aattgcatga agaatctgct tagggttagg cgttttgcgc tgcttcgcga    2880
tgtacgggcc agatatacgc gttgacattg attattgact agttattaat agtaatcaat    2940 tacgggtca ttagttcata gcccatatat ggagttccgc gttacataac ttacggtaaa    3000
tggcccgcct ggctgaccgc ccaacgaccc ccgcccattg acgtcaataa tgacgtatgt    3060
tcccatagta acgccaatag ggactttcca ttgacgtcaa tgggtggagt atttacggta    3120
aactgcccac ttggcagtac atcaagtgta tcatatgcca agtacgcccc ctattgacgt    3180
caatgacggt aaatggcccg cctggcatta tgcccagtac atgaccttat gggactttcc    3240
tacttggcag tacatctacg tattagtcat cgctattacc atggtgatgc ggttttggca    3300
gtacatcaat gggcgtggat agcggtttga ctcacgggga tttccaagtc tccaccccat    3360
tgacgtcaat gggagtttgt tttggcacca aaatcaacgg gactttccaa aatgtcgtaa    3420
caactccgcc ccattgacgc aaatgggcgg taggcgtgta cggtgggagg tctatataag    3480
```

```
cagagctctc tggctaacta gagaacccac tgcttactgg cttatcgaaa ttaatacgac    3540
tcactatagg gagacccaag ctggctagcg tttaaactta agcttcctgg ctatggtggt    3600
ggtggcagcc gcgccgaacc cggccgacgg gaccctaaa gttctgcttc tgtcggggca     3660
gcccgcctcc gccgccggag ccccggccgg ccaggccctg ccgctcatgg tgccagccca    3720
gagaggggcc agcccggagg cagcgagcgg ggggctgccc caggcgcgca agcgacagcg    3780
cctcacgcac ctgagccccg aggagaaggc gctgaggagg aaactgaaaa acagagtagc    3840
agctcagact gccagagatc gaaagaaggc tcgaatgagt gagctggaac agcaagtggt    3900
agatttagaa gaagagaacc aaaaactttt gctagaaaat cagcttttac gagagaaaac    3960
tcatggcctt gtagttgaga accaggagtt aagacagcgc ttggggatgg atgccctggt    4020
tgctgaagag gaggcggaag ccaagggaa tgaagtgagg ccagtggccg ggtctgctga     4080
gtccgcagca ggtgcaggcc cagttgtcac ccctccagaa catctcccca tggattctgg    4140
cggtattgac tcttcagatt cagagtctga tatcctgttg ggcattctgg acaacttgga    4200
cccagtcatg ttcttcaaat gcccttcccc agagcctgcc agcctggagg agctcccaga    4260
ggtctaccca gaaggaccca gttccttacc agcctccctt tctctgtcag tggggacgtc    4320
atcagccaag ctggaagcca ttaatgaact aattcgtttt gaccacatat ataccaagcc    4380
cctagtctta gagataccct ctgagacaga gagccaagct aatgtggtag tgaaaatcga    4440
ggaagcacct ctcagcccct cagagaatga tcaccctgaa ttcattgtct cagtgaagga    4500
agaacctgta gaagatgacc tcgttccgga gctgggtatc tcaaatctgc tttcatccag    4560
ccactgccca aagccatctt cctgcctact ggatgcttac agtgactgtg gatacggggg    4620
ttccctttcc ccattcagtg acatgtcctc tctgcttggt gtaaaccatt cttgggagga    4680
cacttttgcc aatgaactct ttccccagct gattagtgtc ctatttaata agaacaaca    4740 aaatgcgttt tatgaaatac tacatctacc gaatctaaat gaagaacaac gtaatggttt    4800
tatacaatcg ctaaaagatg atccgtcgca atcggcgaat ctactagcgg aagcgaaaaa    4860
actaaatgat gcgcaagcgg cggcgatggg ggagccggct ggggttgccg gcaccatgga    4920
gtcacctttt agcccgggac tctttcacag gctggatgaa gattgggatt ctgctctctt    4980
tgctgaactc ggttatttca cagacactga tgagctgcaa ttggaagcag caaatgagac    5040
gtatgaaaac aattttgata atcttgattt tgatttggat ttgatgcctt gggagtcaga    5100
catttgggac atcaacaacc aaatctgtac agttaaagat attaaggcag aacctcagcc    5160
actttctcca gcctcctcaa gttattcagt ctcgtctcct cggtcagtgg actcttattc    5220
ttcaactcag catgttcctg aggagttgga tttgtcttct agttctcaga tgtctcccct    5280
ttccttatat ggtgaaaact ctaatagtct ctcttcagcg gagccactga aggaagataa    5340
gcctgtcact ggtcctagga caagactga aaatggactg actccaaaga aaaaaattca    5400
ggtgaattca aaaccttcaa ttcagcccaa gcctttattg cttccagcag cacccaagac    5460
tcaaacaaac tccagtgttc cagcaaaaac catcattatt cagacagtac caacgcttat    5520
gccattggca aagcagcaac caattatcag tttacaacct gcacccacta aaggccagac    5580
ggttttgctg tctcagccta ctgtggtaca acttcaagca cctggagttc tgccctctgc    5640
tcagccagtc cttgctgttg ctgggggagt cacacagctc cctaatcacg tggtgaatgt    5700
ggtaccagcc ccttcagcga atagcccagt gaatggaaaa ctttccgtga ctaaacctgt    5760
cctacaaagt accatgagaa atgtcggttc agatattgct gtgctaagga gacagcaacg    5820
```

```
tatgataaaa aatcgagaat ccgcttgtca gtctcgcaag aagaagaaag aatatatgct    5880
agggttagag gcgagattaa aggctgccct ctcagaaaac gagcaactga agaaagaaaa    5940
tggaacactg aagcggcagc tggatgaagt tgtgtcagag aaccagaggc tttacccata    6000
cgatgttcca gattacgcaa tgtaaagagc cacataacac tgggcccctt tccctgacca    6060
tcacattgcc tagaggatag cataggcctg aagggcgaat tccagcacac tggcggccgt    6120
tactagaggg cccgtttaaa cccgctgatc acctcgactg tgccttctag ttgccagcca    6180
tctgttgttt gccccteccc cgtgccttcc ttgaccctgg aaggtgccac tcccactgtc    6240
ctttcctaat aaaatgagga aattgcatcg cattgtctga gtaggtgtca ttctattctg    6300 ggggtgggg tggggcagga cagcaagggg gaggattggg aagacaatag caggcatgcc    6360
tgcagcggtc cggtcgactc tagaggatcc gaaaaaacct cccacacctc ccctgaacc    6420 tgaaacataa aatgaatgca attgttgttg ttaacttgtt tattgcagct tataatggtt    6480
acaaataaag caatagcatc acaaatttca caaataaagc attttttca ctgcattcta    6540 gttgtggttt gtccaaactc atcaatgtat cttatcatgt ctggatcccc gcggtggcgg    6600
ccgcactagt cccgggttaa ttaagctagc agatcttgat cacctaggcg tacgatttgg    6660
ccgctttaca tggtggcgac cggggatcct ctagtaccaa gctaattcct cacgacacct    6720
gaaatggaag aaaaaaactt tgaaccactg tctgaggctt gagaatgaac caagatccaa    6780
actcaaaaag ggcaaattcc aaggagaatt acatcaagtg ccaagctggc ctaacttcag    6840
tctccaccca ctcagtgtgg ggaaactcca tcgcataaaa ccctccccc caacctaaag    6900 acgacgtact ccaaaagctc gagaactaat cgaggtgcct ggacggcgcc cggtactccg    6960
tggagtcaca tgaagcgacg gctgaggacg gaaaggccct tttcctttgt gtgggtgact    7020 cacccgccc ctctcccgag cgccgcgtcc tccattttga gctccctgca gcagggccgg    7080
gaagcggcca tctttccgct cacgcaactg gtgccgaccg ggccagcctt ccgcccagg    7140 gcggggcgat acacggcggc gcgaggccag gcaccagagc aggccggcca gcttgagact    7200
acccccgtcc gattctcggt ggccgcgctc gcaggccccg cctcgccgaa catgtgcgct    7260
gggacgcacg ggccccgtcg ccgcccgcgg ccccaaaaac cgaaatacca gtgtgcagat    7320
cttggcccgc atttacaaga ctatcttgcc agaaaaaaag cgtcgcagca ggtcatcaaa    7380
aattttaaat ggctagagac ttatcgaaag cagcgagaca ggcgcgaagg tgccaccaga    7440
ttcgcacgcg gcggccccag cgcccaggcc aggcctcaac tcaagcacga ggcgaagggg    7500
ctccttaagc gcaaggcctc gaactctccc acccacttcc aacccgaagc tcgggatcaa    7560
gaatcacgta ctgcagccag gtggaagtaa ttcaaggcac gcaagggcca taacccgtaa    7620
agaggccagg cccgcgggaa ccacacacgg cacttacctg tgttctggcg gcaaacccgt    7680
tgcgaaaaag aacgttcacg gcgactactg cacttatata cggttctccc ccaccctcgg    7740
gaaaaaggcg gagccagtac acgacatcac tttcccagtt taccccgcgc caccttctct    7800
aggcaccgg                                                           7809

<210> SEQ ID NO 6
<211> LENGTH: 7701
<212> TYPE: DNA
<213> ORGANISM: Artificial Sequence
<220> FEATURE:
<223> OTHER INFORMATION: pAAV_XBP1s-LFG-ATF6f-HA

<400> SEQUENCE: 6
ggcggatcca attgcctagg cccaagggcg aattgtcacg actccacccc tccaggaacc        60
```

```
cctagtgatg gagttggcca ctccctctct gcgcgctcgc tcgctcactg aggccgcccg    120
ggcaaagccc gggcgtcggg cgacctttgg tcgcccggcc tcagtgagcg agcgagcgcg    180
cagagaggga gtggcccaga tctgatatca tcgatgaatt caagcttcag ctgctcgagt    240
tctatagtgt cacctaaatc gtatgtgtat gatacataag gttatgtatt aattgtagcc    300
gcgttctaac gacaatatgt ccatatggtg cactctcagt acaatctgct ctgatgccgc    360
atagttaagc cagccccgac acccgccaac acccgctgac gcgccctgac gggcttgtct    420
gctcccggca tccgcttaca gacaagctgt gaccgtctcc gggagctgca tgtgtcagag    480
gttttcaccg tcatcaccga aacgcgcgag acgaaagggc ctcgtgatac gcctattttt    540
ataggttaat gtcatgataa taatggtttc ttagacgtca ggtggcactt ttcggggaaa    600
tgtgcgcgga acccctattt gtttattttt ctaaatacat tcaaatatgt atccgctcat    660
gagacaataa ccctgataaa tgcttcaata atattgaaaa aggaagagta tgagtattca    720
acatttccgt gtcgccctta ttcccttttt tgcggcattt tgccttcctg ttttgctca    780 cccagaaacg ctggtgaaag taaaagatgc tgaagatcag ttgggtgcac gagtgggtta    840
catcgaactg gatctcaaca gcggtaagat ccttgagagt tttcgccccg aagaacgttt    900
tccaatgatg agcactttta aagttctgct atgtggcgcg gtattatccc gtattgacgc    960
cgggcaagag caactcggtc gccgcataca ctattctcag aatgacttgg ttgagtactc   1020
accagtcaca gaaaagcatc ttacggatgg catgacagta agagaattat gcagtgctgc   1080
cataaccatg agtgataaca ctgcggccaa cttacttctg acaacgatcg gaggaccgaa   1140
ggagctaacc gcttttttgc acaacatggg ggatcatgta actcgccttg atcgttggga   1200
accggagctg aatgaagcca taccaaacga cgagcgtgac accacgatgc ctgtagcaat   1260
ggcaacaacg ttgcgcaaac tattaactgg cgaactactt actctagctt cccggcaaca   1320
attaatagac tggatggagg cggataaagt tgcaggacca cttctgcgct cggcccttcc   1380
ggctggctgg tttattgctg ataaatctgg agccggtgag cgtgggtctc gcggtatcat   1440
tgcagcactg gggccagatg gtaagccctc ccgtatcgta gttatctaca cgacggggag   1500
tcaggcaact atggatgaac gaaatagaca gatcgctgag ataggtgcct cactgattaa   1560
gcattggtaa ctgtcagacc aagtttactc atatatactt tagattgatt taaaacttca   1620
tttttaattt aaaaggatct aggtgaagat cctttttgat aatctcatga ccaaaatccc   1680
ttaacgtgag ttttcgttcc actgagcgtc agaccccgta gaaaagatca aaggatcttc   1740
ttgagatcct ttttttctgc gcgtaatctg ctgcttgcaa acaaaaaaac caccgctacc   1800
agcggtggtt tgtttgccgg atcaagagct accaactctt tttccgaagg taactggctt   1860
cagcagagcg cagataccaa atactgtcct tctagtgtag ccgtagttag gccaccactt   1920
caagaactct gtagcaccgc ctacatacct cgctctgcta atcctgttac cagtggctgc   1980
tgccagtggc gataagtcgt gtcttaccgg gttggactca agacgatagt taccggataa   2040
ggcgcagcgg tcgggctgaa cggggggttc gtgcacacag cccagcttgg agcgaacgac   2100
ctacaccgaa ctgagatacc tacagcgtga gcattgagaa agcgccacgc ttcccgaagg   2160
gagaaaggcg gacaggtatc cggtaagcgg cagggtcgga acaggagagc gcacgaggga   2220
gcttccaggg ggaaacgcct ggtatcttta tagtcctgtc gggtttcgcc acctctgact   2280
tgagcgtcga tttttgtgat gctcgtcagg gggcggagc ctatggaaaa acgccagcaa   2340
cgcggccttt ttacggttcc tggccttttg ctggccttt gctcacatgt tctttcctgc   2400
```

-continued

```
gttatcccct gattctgtgg ataaccgtat taccgccttt gagtgagctg ataccgctcg    2460
ccgcagccga acgaccgagc gcagcgagtc agtgagcgag gaagcggaag agcgcccaat    2520
acgcaaaccg cctctccccg cgcgttggcc gattcattaa tgcaggttaa cctggcttat    2580
cgaaattaat acgactcact atagggagac cggcagatct gtccctctct gcgcgctcgc    2640
tcgctcactg aggccgcccg ggcaaagccc gggcgtcggg cgacctttgg tcgcccggcc    2700
tcagtgagcg agcgagcgcg cagagaggga gtggccaact ccatcactag ggttccttg    2760 tagttaatga ttaacccgcc atgctactta tctacaattc gcccttcgga cgcgtggctt    2820
cgaactaggc aattgcatga agaatctgct tagggttagg cgttttgcgc tgcttcgcga    2880
tgtacgggcc agatatacgc gttgacattg attattgact agttattaat agtaatcaat    2940
tacggggtca ttagttcata gcccatatat ggagttccgc gttacataac ttacggtaaa    3000
tggcccgcct ggctgaccgc ccaacgaccc ccgcccattg acgtcaataa tgacgtatgt    3060
tcccatagta acgccaatag ggactttcca ttgacgtcaa tgggtggagt atttacggta    3120
aactgcccac ttggcagtac atcaagtgta tcatatgcca agtacgcccc ctattgacgt    3180
caatgacggt aaatggcccg cctggcatta tgcccagtac atgaccttat gggactttcc    3240
tacttggcag tacatctacg tattagtcat cgctattacc atggtgatgc ggttttggca    3300
gtacatcaat gggcgtggat agcggtttga ctcacgggga tttccaagtc tccaccccat    3360
tgacgtcaat gggagtttgt tttggcacca aaatcaacgg gactttccaa aatgtcgtaa    3420
caactccgcc ccattgacgc aaatgggcgg taggcgtgta cggtgggagg tctatataag    3480
cagagctctc tggctaacta gagaacccac tgcttactgg cttatcgaaa ttaatacgac    3540
tcactatagg gagacccaag ctggctagcg tttaaactta agcttcctgg ctatggtggt    3600
ggtggcagcc gcgccgaacc cggccgacgg gaccctaaa gttctgcttc tgtcggggca    3660
gcccgcctcc gccgcggag ccccggccgg ccaggccctg ccgctcatgg tgccagccca    3720
gagagggggc agcccggagg cagcgagcgg ggggctgccc caggcgcgca agcgacagcg    3780
cctcacgcac ctgagccccg aggagaaggc gctgaggagg aaactgaaaa acagagtagc    3840
agctcagact gccagagatc gaaagaaggc tcgaatgagt gagctggaac agcaagtggt    3900
agatttagaa gaagagaacc aaaaactttt gctagaaaat cagcttttac gagagaaaac    3960
tcatggcctt gtagttgaga accaggagtt aagacagcgc ttggggatgg atgccctggt    4020
tgctgaagag gaggcggaag ccaaggggaa tgaagtgagg ccagtggccg ggtctgctga    4080
gtccgcagca ggtgcaggcc cagttgtcac ccctccagaa catctcccca tggattctgg    4140
cggtattgac tcttcagatt cagagtctga tatcctgttg ggcattctgg acaacttgga    4200
cccagtcatg ttcttcaaat gcccttcccc agagcctgcc agcctggagg agctcccaga    4260
ggtctaccca gaaggaccca gttccttacc agcctccctt tctctgtcag tggggacgtc    4320
atcagccaag ctggaagcca ttaatgaact aattcgtttt gaccacatat ataccaagcc    4380
cctagtctta gagataccct ctgagacaga gagccaagct aatgtggtag tgaaaatcga    4440
ggaagcacct ctcagcccct cagagaatga tcaccctgaa ttcattgtct cagtgaagga    4500
agaacctgta gaagatgacc tcgttccgga gctgggtatc tcaaatctgc tttcatccag    4560
ccactgccca aagccatctt cctgcctact ggatgcttac agtgactgtg atacgggggg    4620
ttccctttcc ccattcagtg acatgtcctc tctgcttggt gtaaaccatt cttgggagga    4680
cacttttgcc aatgaactct ttccccagct gattagtgtc ctaggtggtg gtggttcggg    4740
tggtggtggt tcgggtggtg gtggttcggc ggcggcgatg ggggagccgg ctggggttgc    4800
```

```
cggcaccatg gagtcacctt ttagcccggg actctttcac aggctggatg aagattggga    4860
ttctgctctc tttgctgaac tcggttattt cacagacact gatgagctgc aattggaagc    4920
agcaaatgag acgtatgaaa acaattttga taatcttgat tttgatttgg atttgatgcc    4980
ttgggagtca gacatttggg acatcaacaa ccaaatctgt acagttaaag atattaaggc    5040
agaacctcag ccactttctc cagcctcctc aagttattca gtctcgtctc ctcggtcagt    5100
ggactcttat tcttcaactc agcatgttcc tgaggagttg gatttgtctt ctagttctca    5160
gatgtctccc ctttccttat atggtgaaaa ctctaatagt ctctcttcag cggagccact    5220
gaaggaagat aagcctgtca ctggtcctag gaacaagact gaaaatggac tgactccaaa    5280
gaaaaaaatt caggtgaatt caaaaccttc aattcagccc aagcctttat tgcttccagc    5340
agcacccaag actcaaacaa actccagtgt tccagcaaaa accatcatta ttcagacagt    5400
accaacgctt atgccattgg caaagcagca accaattatc agtttacaac ctgcacccac    5460
taaaggccag acgttttgc tgtctcagcc tactgtggta caacttcaag cacctggagt    5520
tctgccctct gctcagccag tccttgctgt tgctggggga gtcacacagc tccctaatca    5580
cgtggtgaat gtggtaccag ccccttcagc gaatagccca gtgaatggaa aactttccgt    5640
gactaaacct gtcctacaaa gtaccatgag aaatgtcggt tcagatattg ctgtgctaag    5700
gagacagcaa cgtatgataa aaaatcgaga atccgcttgt cagtctcgca agaagaagaa    5760
agaatatatg ctagggttag aggcgagatt aaaggctgcc ctctcagaaa acgagcaact    5820
gaagaaagaa aatggaacac tgaagcggca gctggatgaa gttgtgtcag agaaccagag    5880
gctttaccca tacgatgttc cagattacgc aatgtaaaga gccacataac actgggcccc    5940
tttccctgac catcacattg cctagaggat agcataggcc tgaagggcga attccagcac    6000
actggcggcc gttactagag ggcccgttta aacccgctga tcacctcgac tgtgccttct    6060
agttgccagc catctgttgt ttgcccctcc cccgtgcctt ccttgaccct ggaaggtgcc    6120
actcccactg tcctttccta ataaaatgag gaaattgcat cgcattgtct gagtaggtgt    6180
cattctattc tggggggtgg ggtggggcag gacagcaagg gggaggattg ggaagacaat    6240
agcaggcatg cctgcagcgg tccggtcgac tctagaggat ccgaaaaaac ctcccacacc    6300
tccccctgaa cctgaaacat aaaatgaatg caattgttgt tgttaacttg tttattgcag    6360
cttataatgg ttacaaataa agcaatagca tcacaaattt cacaaataaa gcatttttt    6420 cactgcattc tagttgtggt ttgtccaaac tcatcaatgt atcttatcat gtctggatcc    6480
ccgcggtggc ggccgcacta gtcccgggtt aattaagcta gcagatcttg atcacctagg    6540
cgtacgattt ggccgcttta catggtggcg accggggatc ctctagtacc aagctaattc    6600
ctcacgacac ctgaaatgga agaaaaaaac tttgaaccac tgtctgaggc ttgagaatga    6660
accaagatcc aaactcaaaa agggcaaatt ccaaggagaa ttacatcaag tgccaagctg    6720
gcctaacttc agtctccacc cactcagtgt ggggaaactc catcgcataa acccctcccc    6780
cccaacctaa agacgacgta ctccaaaagc tcgagaacta atcgaggtgc ctggacggcg    6840
cccggtactc cgtggagtca catgaagcga cggctgagga cggaaaggcc cttttccttt    6900
gtgtgggtga ctcacccgcc cgctctcccg agcgccgcgt cctccatttt gagctccctg    6960
cagcagggcc gggaagcggc catctttccg ctcacgcaac tggtgccgac cgggccagcc    7020
ttgccgccca gggcggggcg atacacggcg gcgcgaggcc aggcaccaga gcaggccggc    7080
cagcttgaga ctaccccgt ccgattctcg gtggccgcgc tcgcaggccc cgcctcgccg    7140
```

```
aacatgtgcg ctgggacgca cgggccccgt cgccgcccgc ggccccaaaa accgaaatac    7200
cagtgtgcag atcttggccc gcatttacaa gactatcttg ccagaaaaaa agcgtcgcag    7260
caggtcatca aaaattttaa atggctagag acttatcgaa agcagcgaga caggcgcgaa    7320
ggtgccacca gattcgcacg cggcggcccc agcgccaggg ccaggcctca actcaagcac    7380
gaggcgaagg ggctccttaa gcgcaaggcc tcgaactctc ccacccactt ccaacccgaa    7440
gctcgggatc aagaatcacg tactgcagcc aggtggaagt aattcaaggc acgcaagggc    7500
cataacccgt aaagaggcca ggcccgcggg aaccacacac ggcacttacc tgtgttctgg    7560
cggcaaaccc gttgcgaaaa agaacgttca cggcgactac tgcacttata tacggttctc    7620 ccccacccctc gggaaaaagg cggagccagt acacgacatc actttccag tttaccccgc    7680 gccaccttct ctaggcaccg g                                              7701

<210> SEQ ID NO 7
<211> LENGTH: 1108
<212> TYPE: DNA
<213> ORGANISM: Homo sapiens
<220> FEATURE:
<221> NAME/KEY: mRNA
<222> LOCATION: (1)..(1108)
<223> OTHER INFORMATION: Homo sapiens activating transcription factor 6
      (ATF6f)

<400> SEQUENCE: 7
atgggggagc cggctggggt tgccggcacc atggagtcac cttttagccc gggactcttt      60
cacaggctgg atgaagattg ggattctgct ctctttgctg aactcggtta tttcacagac     120
actgatgagc tgcaattgga agcagcaaat gagacgtatg aaaacaattt tgataatctt     180
gattttgatt tggatttgat gccttgggag tcagacattt gggacatcaa caaccaaatc     240
tgtacagtta aagatattaa ggcagaacct cagccacttt ctccagcctc ctcaagttat     300
tcagtctcgt ctcctcggtc agtggactct tattcttcaa ctcagcatgt tcctgaggag     360
ttggatttgt cttctagttc tcagatgtct ccccttctcct tatatggtga aaactctaat     420
agtctctctt cagcggagcc actgaaggaa gataagcctg tcactggtcc taggaacaag     480
actgaaaatg gactgactcc aaagaaaaaa attcaggtga attcaaaacc ttcaattcag     540
cccaagcctt tattgcttcc agcagcaccc aagactcaaa caaactccag tgttccagca     600
aaaaccatca ttattcagac agtaccaacg cttatgccat ggcaaagca gcaaccaatt     660 atcagtttac aacctgcacc cactaaaggc cagacggttt tgctgtctca gcctactgtg     720
gtacaacttc aagcacctgg agttctgccc tctgctcagc cagtccttgc tgttgctggg     780
ggagtcacac agctccctaa tcacgtggtg aatgtggtac cagccccttc agcgaatagc     840
ccagtgaatg gaaaactttc cgtgactaaa cctgtcctac aaagtaccat gagaaatgtc     900
ggttcagata ttgctgtgct aaggagacag caacgtatga taaaaaatcg agaatccgct     960
tgtcagtctc gcaagaagaa gaaagaatat atgctagggt tagaggcgag attaaaggct    1020
gccctctcag aaaacgagca actgaagaaa gaaaatggaa cactgaagcg gcagctggat    1080
gaagttgtgt cagagaacca gaggctta                                       1108

<210> SEQ ID NO 8
<211> LENGTH: 1128
<212> TYPE: DNA
<213> ORGANISM: Homo sapiens
<220> FEATURE:
<221> NAME/KEY: mRNA
<222> LOCATION: (1)..(1128)
```

<223> OTHER INFORMATION: Homo sapiens X-box binding protein 1 (XBP1s),
      transcript variant 2

<400> SEQUENCE: 8

```
atggtggtgg tggcagccgc gccgaacccg gccgacggga cccctaaagt tctgcttctg    60
tcggggcagc ccgcctccgc cgccggagcc ccggccggcc aggccctgcc gctcatggtg   120
ccagcccaga gaggggccag cccggaggca gcgagcgggg ggctgcccca ggcgcgcaag   180
cgacagcgcc tcacgcacct gagccccgag gagaaggcgc tgaggaggaa actgaaaaac   240
agagtagcag ctcagactgc cagagatcga agaaggctc gaatgagtga gctggaacag   300
caagtggtag atttagaaga agagaaccaa aaacttttgc tagaaaatca gcttttacga   360
gagaaaactc atggccttgt agttgagaac caggagttaa gacagcgctt ggggatggat   420
gccctggttg ctgaagagga ggcggaagcc aaggggaatg aagtgaggcc agtggccggg   480
tctgctgagt ccgcagcagg tgcaggccca gttgtcaccc tccagaaaca tctccccatg   540
gattctggcg gtattgactc ttcagattca gagtctgata tcctgttggg cattctggac   600
aacttggacc cagtcatgtt cttcaaatgc ccttccccag agcctgccag cctggaggag   660
ctcccagagg tctacccaga aggacccagt tccttaccag cctcccttc tctgtcagtg   720 gggacgtcat cagccaagct ggaagccatt aatgaactaa ttcgttttga ccacatatat   780
accaagcccc tagtcttaga ataccctct gagacagaga gccaagctaa tgtggtagtg   840
aaaatcgagg aagcacctct cagcccctca gagaatgatc accctgaatt cattgtctca   900
gtgaaggaag aacctgtaga agatgacctc gttccggagc tgggtatctc aaatctgctt   960
tcatccagcc actgcccaaa gccatcttcc tgcctactgg atgcttacag tgactgtgga  1020
tacgggggtt cccttttcccc attcagtgac atgtcctctc tgcttggtgt aaaccattct  1080
tgggaggaca cttttgccaa tgaactcttt ccccagctga ttagtgtc                1128
```

<210> SEQ ID NO 9
<211> LENGTH: 57
<212> TYPE: DNA
<213> ORGANISM: Artificial Sequence
<220> FEATURE:
<223> OTHER INFORMATION: Linker LFG

<400> SEQUENCE: 9

```
ctaggtggtg gtggttcggg tggtggtggt tcgggtggtg gtggttcggc ggcggcg     57
```

<210> SEQ ID NO 10
<211> LENGTH: 75
<212> TYPE: DNA
<213> ORGANISM: Artificial Sequence
<220> FEATURE:
<223> OTHER INFORMATION: Linker L4H4

<400> SEQUENCE: 10

```
ctagcggaag cggcggcgaa agaagcggcg gcgaaagaag cggcggcgaa agaagcggcg    60
gcgaaagcgg cggcg                                                    75
```

<210> SEQ ID NO 11
<211> LENGTH: 165
<212> TYPE: DNA
<213> ORGANISM: Artificial Sequence
<220> FEATURE:
<223> OTHER INFORMATION: Linker LF

<400> SEQUENCE: 11

-continued

| | |
|---|---|
| ctatttaata aagaacaaca aaatgcgttt tatgaaatac tacatctacc gaatctaaat | 60 |
| gaagaacaac gtaatggttt tatacaatcg ctaaaagatg atccgtcgca atcggcgaat | 120 |
| ctactagcgg aagcgaaaaa actaaatgat gcgcaagcgg cggcg | 165 |

<210> SEQ ID NO 12
<211> LENGTH: 4679
<212> TYPE: DNA
<213> ORGANISM: adeno-associated virus 2
<300> PUBLICATION INFORMATION:
<308> DATABASE ACCESSION NUMBER: AF043303.1
<309> DATABASE ENTRY DATE: 2010-05-20
<313> RELEVANT RESIDUES IN SEQ ID NO: (1)..(4679)

<400> SEQUENCE: 12

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgtatt agaggtcacg tgagtgtttt cgacattttt gcgacaccat | 240 |
| gtggtcacgc tgggtattta agcccgagtg agcacgcagg gtctccattt tgaagcggga | 300 |
| ggtttgaacg cgcagccgcc atgccggggt tttacgagat tgtgattaag gtccccagcg | 360 |
| accttgacga gcatctgccc ggcatttctg acagctttgt gaactgggtg gccgagaagg | 420 |
| aatgggagtt gccgccagat tctgacatgg atctgaatct gattgagcag gcaccctga | 480 |
| ccgtggccga gaagctgcag cgcgactttc tgacggaatg cgccgtgtg agtaaggccc | 540 |
| cggaggcect tttctttgtg caatttgaga agggagagag ctacttccac atgcacgtgc | 600 |
| tcgtggaaac caccggggtg aaatccatgg ttttgggacg tttcctgagt cagattcgcg | 660 |
| aaaaactgat tcagagaatt taccgcggga tcgagccgac tttgccaaac tggttcgcgg | 720 |
| tcacaaagac cagaaatggc gccggaggcg ggaacaaggt ggtggatgag tgctacatcc | 780 |
| ccaattactt gctcccccaaa acccagcctg agctccagtg ggcgtggact aatatggaac | 840 |
| agtatttaag cgcctgtttg aatctcacgg agcgtaaacg gttggtggcg cagcatctga | 900 |
| cgcacgtgtc gcagacgcag gagcagaaca aagagaatca gaatcccaat tctgatgcgc | 960 |
| cggtgatcag atcaaaaact tcagccaggt acatggagct ggtcgggtgg ctcgtggaca | 1020 |
| agggattac ctcggagaag cagtggatcc aggaggacca ggcctcatac atctccttca | 1080 |
| atgcggcctc caactcgcgg tcccaaatca aggctgcctt ggacaatgcg ggaaagatta | 1140 |
| tgagcctgac taaaaccgcc cccgactacc tggtgggcca gcagcccgtg gaggacattt | 1200 |
| ccagcaatcg gatttataaa attttggaac taaacgggta cgatccccaa tatgcggctt | 1260 |
| ccgtctttct gggatgggcc acgaaaaagt tcggcaagag gaacaccatc tggctgtttg | 1320 |
| ggcctgcaac taccgggaag accaacatcg cggaggccat agcccacact gtgcccttct | 1380 |
| acgggtgcgt aaactggacc aatgagaact ttccccttca cgactgtgtc gacaagatgg | 1440 |
| tgatctggtg ggaggagggg aagatgaccg ccaaggtcgt ggagtcggcc aaagccattc | 1500 |
| tcggaggaag caaggtgcgc gtggaccaga aatgcaagtc ctcggcccag atagacccga | 1560 |
| ctcccgtgat cgtcacctcc aacaccaaca tgtgcgccgt gattgacggg aactcaacga | 1620 |
| ccttcgaaca ccagcagccg ttgcaagacc ggatgttcaa atttgaactc accgccgtc | 1680 |
| tggatcatga ctttgggaag gtcaccaagc aggaagtcaa agactttttc cggtgggcaa | 1740 |
| aggatcacgt ggttgaggtg gagcatgaat tctacgtcaa aaagggtgga gccaagaaaa | 1800 |
| gacccgcccc cagtgacgca gatataagtg agcccaaacg ggtgcgcgag tcagttgcgc | 1860 |

-continued

```
agccatcgac gtcagacgcg gaagcttcga tcaactacgc agacaggtac caaaacaaat    1920
gttctcgtca cgtgggcatg aatctgatgc tgtttccctg cagacaatgc gagagaatga    1980
atcagaattc aaatatctgc ttcactcacg gacagaaaga ctgtttagag tgctttcccg    2040
tgtcagaatc tcaacccgtt tctgtcgtca aaaggcgta tcagaaactg tgctacattc     2100
atcatatcat gggaaaggtg ccagacgctt gcactgcctg cgatctggtc aatgtggatt    2160
tggatgactg catctttgaa caataaatga tttaaatcag gtatggctgc cgatggttat    2220
cttccagatt ggctcgagga cactctctct gaaggaataa gacagtggtg gaagctcaaa    2280
cctggcccac caccaccaaa gcccgcagag cggcataagg acgacagcag gggtcttgtg    2340
cttcctgggt acaagtacct cggacccttc aacggactcg acaagggaga gccggtcaac    2400
gaggcagacg ccgcggccct cgagcacgac aaagcctacg accggcagct cgacagcgga    2460
gacaacccgt acctcaagta caaccacgcc gacgcggagt tcaggagcg ccttaaagaa     2520 gatacgtctt ttgggggcaa cctcggacga gcagtcttcc aggcgaaaaa gagggttctt    2580
gaacctctgg gcctggttga ggaacctgtt aagacggctc cgggaaaaaa gaggccggta    2640
gagcactctc ctgtggagcc agactcctcc tcgggaaccg gaaaggcggg ccagcagcct    2700
gcaagaaaaa gattgaattt tggtcagact ggagacgcag actcagtacc tgaccccag     2760 cctctcggac agccaccagc agccccctct ggtctgggaa ctaatacgat ggctacaggc    2820
agtggcgcac caatggcaga caataacgag ggcgccgacg gagtgggtaa ttcctcggga    2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca atcactactt tggctacagc accccttggg ggtattttga cttcaacaga    3060
ttccactgcc acttttcacc acgtgactgg caaagactca tcaacaacaa ctggggattc    3120
cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcatttta ctgcctggag tactttcctt ctcagatgct gcgtaccgga    3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg gaccctgtta ccgccagcag    3660
cgagtatcaa agacatctgc ggataacaac aacagtgaat actcgtggac tggagctacc    3720
aagtaccacc tcaatggcag agactctctg gtgaatccgg gcccggccat ggcaagccac    3780
aaggacgatg aagaaaagtt ttttcctcag agcgggggttc tcatctttgg gaagcaaggc    3840
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catgggtgga ttcggactta acaccctcc tccacagatt     4140 ctcatcaaga acacccccggt acctgcgaat ccttcgacca ccttcagtgc ggcaaagttt    4200
```

| | |
|---|---|
| gcttccttca tcacacagta ctccacggga caggtcagcg tggagatcga gtgggagctg | 4260 |
| cagaaggaaa acagcaaacg ctggaatccc gaaattcagt acacttccaa ctacaacaag | 4320 |
| tctgttaatg tggactttac tgtggacact aatggcgtgt attcagagcc tcgcccatt | 4380 |
| ggcaccagat acctgactcg taatctgtaa ttgcttgtta atcaataaac cgtttaattc | 4440 |
| gtttcagttg aactttggtc tctgcgtatt tctttcttat ctagtttcca tggctacgta | 4500 |
| gataagtagc atggcgggtt aatcattaac tacaaggaac ccctagtgat ggagttggcc | 4560 |
| actccctctc tgcgcgctcg ctcgctcact gaggccgggc gaccaaaggt cgcccgacgc | 4620 |
| ccgggctttg cccgggcggc ctcagtgagc gagcgagcgc gcagagaggg agtggccaa | 4679 |

<210> SEQ ID NO 13
<211> LENGTH: 6516
<212> TYPE: DNA
<213> ORGANISM: Artificial Sequence
<220> FEATURE:
<223> OTHER INFORMATION: pAAV_ATF6f-HA

<400> SEQUENCE: 13

| | |
|---|---|
| ggcggatcca attgcctagg cccaagggcg aattgtcacg actccacccc tccaggaacc | 60 |
| cctagtgatg gagttggcca ctccctctct gcgcgctcgc tcgctcactg aggccgcccg | 120 |
| ggcaaagccc gggcgtcggg cgacctttgg tcgcccggcc tcagtgagcg agcgagcgcg | 180 |
| cagagaggga gtgcccagat ctgatatca tcgatgaatt caagcttcag ctgctcgagt | 240 |
| tctatagtgt cacctaaatc gtatgtgtat gatacataag gttatgtatt aattgtagcc | 300 |
| gcgttctaac gacaatatgt ccatatggtg cactctcagt acaatctgct ctgatgccgc | 360 |
| atagttaagc cagccccgac acccgccaac accccgctgac gcgccctgac gggcttgtct | 420 |
| gctcccggca tccgcttaca gacaagctgt gaccgtctcc gggagctgca tgtgtcagag | 480 |
| gttttcaccg tcatcaccga aacgcgcgag acgaaagggc ctcgtgatac gcctattttt | 540 |
| ataggttaat gtcatgataa taatggtttc ttagacgtca ggtggcactt ttcggggaaa | 600 |
| tgtgcgcgga accctatttt gtttattttt ctaaatacat tcaaatatgt atccgctcat | 660 |
| gagacaataa ccctgataaa tgcttcaata atattgaaaa aggaagagta tgagtattca | 720 |
| acatttccgt gtcgccctta ttcccttttt tgcggcattt tgccttcctg ttttttgctca | 780 |
| cccagaaacg ctggtgaaag taaaagatgc tgaagatcag ttgggtgcac gagtgggtta | 840 |
| catcgaactg gatctcaaca gcggtaagat ccttgagagt tttcgccccg aagaacgttt | 900 |
| tccaatgatg agcactttta aagttctgct atgtggcgcg gtattatccc gtattgacgc | 960 |
| cgggcaagag caactcggtc gccgcataca ctattctcag aatgacttgg ttgagtactc | 1020 |
| accagtcaca gaaaagcatc ttacggatgg catgacagta agagaattat gcagtgctgc | 1080 |
| cataaccatg agtgataaca ctgcggccaa cttacttctg acaacgatcg gaggaccgaa | 1140 |
| ggagctaacc gcttttttgc acaacatggg ggatcatgta actcgccttg atcgttggga | 1200 |
| accggagctg aatgaagcca taccaaacga cgagcgtgac accacgatgc ctgtagcaat | 1260 |
| ggcaacaacg ttgcgcaaac tattaactgg cgaactactt actctagctt cccggcaaca | 1320 |
| attaatagac tggatggagg cggataaagt tgcaggacca cttctgcgct cggcccttcc | 1380 |
| ggctggctgg tttattgctg ataaatctgg agccggtgag cgtgggtctc gcggtatcat | 1440 |
| tgcagcactg gggccagatg gtaagccctc ccgtatcgta gttatctaca cgacggggag | 1500 |
| tcaggcaact atggatgaac gaaatagaca gatcgctgag ataggtgcct cactgattaa | 1560 |
| gcattggtaa ctgtcagacc aagtttactc atatatactt tagattgatt taaaacttca | 1620 |

```
tttttaattt aaaaggatct aggtgaagat ccttttttgat aatctcatga ccaaaatccc   1680
ttaacgtgag ttttcgttcc actgagcgtc agacccccgta gaaaagatca aaggatcttc   1740
ttgagatcct ttttttctgc gcgtaatctg ctgcttgcaa acaaaaaaac caccgctacc   1800
agcggtggtt tgtttgccgg atcaagagct accaactctt tttccgaagg taactggctt   1860
cagcagagcg cagataccaa atactgtcct tctagtgtag ccgtagttag gccaccactt   1920
caagaactct gtagcaccgc ctacatacct cgctctgcta atcctgttac cagtggctgc   1980
tgccagtggc gataagtcgt gtcttaccgg gttggactca agacgatagt taccggataa   2040
ggcgcagcgg tcgggctgaa cggggggttc gtgcacacag cccagcttgg agcgaacgac   2100
ctacaccgaa ctgagatacc tacagcgtga gcattgagaa agcgccacgc ttcccgaagg   2160
gagaaaggcg gacaggtatc cggtaagcgg cagggtcgga acaggagagc gcacgaggga   2220
gcttccaggg ggaaacgcct ggtatcttta tagtcctgtc gggtttcgcc acctctgact   2280
tgagcgtcga ttttttgtgat gctcgtcagg ggggcgagc ctatggaaaa acgccagcaa   2340
cgcggccttt ttacggttcc tggccttttg ctggcctttt gctcacatgt tctttcctgc   2400
gttatcccct gattctgtgg ataaccgtat taccgccttt gagtgagctg ataccgctcg   2460
ccgcagccga acgaccgagc gcagcgagtc agtgagcgag gaagcggaag agcgcccaat   2520
acgcaaaccg cctctccccg cgcgttggcc gattcattaa tgcaggttaa cctggcttat   2580
cgaaattaat acgactcact ataggagac cggcagatct gtccctctct gcgcgctcgc   2640
tcgctcactg aggccgcccg ggcaaagccc gggcgtcggg cgacctttgg tcgcccggcc   2700
tcagtgagcg agcgagcgcg cagagaggga gtggccaact ccatcactag gggttccttg   2760
tagttaatga ttaacccgcc atgctactta tctacaattc gcccttcgga cgcgtggctt   2820
cgaactaggc aattgcatga agaatctgct tagggttagg cgttttgcgc tgcttcgcga   2880
tgtacgggcc agatatacgc gttgacattg attattgact agttattaat agtaatcaat   2940
tacgggtca ttagttcata gcccatatat ggagttccgc gttacataac ttacggtaaa   3000
tggcccgcct ggctgaccgc ccaacgaccc ccgcccattg acgtcaataa tgacgtatgt   3060
tcccatagta acgccaatag ggactttcca ttgacgtcaa tgggtggagt atttacggta   3120
aactgcccac ttggcagtac atcaagtgta tcatatgcca agtacgcccc ctattgacgt   3180
caatgacggt aaatggcccg cctggcatta tgcccagtac atgaccttat gggactttcc   3240
tacttggcag tacatctacg tattagtcat cgctattacc atggtgatgc ggttttggca   3300
gtacatcaat gggcgtggat agcggtttga ctcacgggga tttccaagtc tccaccccat   3360
tgacgtcaat gggagtttgt tttggcacca aaatcaacgg gactttccaa aatgtcgtaa   3420
caactccgcc ccattgacgc aaatgggcgg taggcgtgta cggtgggagg tctatataag   3480
cagagctctc tggctaacta gagaacccac tgcttactgg cttatcgaaa ttaatacgac   3540
tcactatagg gagacccaag ctggctagcg tttaaactta gcttcctgg ctatggggga   3600
gccggctggg gttgccggca ccatggagtc accttttagc ccgggactct ttcacaggct   3660
ggatgaagat tgggattctg ctctctttgc tgaactcggt tatttcacag acactgatga   3720
gctgcaattg gaagcagcaa atgagacgta tgaaaacaat tttgataatc ttgattttga   3780
tttggatttg atgccttggg agtcagacat ttgggacatc aacaaccaaa tctgtacagt   3840
taaagatatt aaggcagaac ctcagccact ttctccagcc tcctcaagtt attcagtctc   3900
gtctcctcgg tcagtggact cttattcttc aactcagcat gttcctgagg agttggattt   3960
```

```
gtcttctagt tctcagatgt ctcccctttc cttatatggt gaaaactcta atagtctctc    4020
ttcagcggag ccactgaagg aagataagcc tgtcactggt cctaggaaca agactgaaaa    4080
tggactgact ccaaagaaaa aaattcaggt gaattcaaaa ccttcaattc agcccaagcc    4140
tttattgctt ccagcagcac ccaagactca aacaaactcc agtgttccag caaaaaccat    4200
cattattcag acagtaccaa cgcttatgcc attggcaaag cagcaaccaa ttatcagttt    4260
acaacctgca cccactaaag gccagacggt tttgctgtct cagcctactg tggtacaact    4320
tcaagcacct ggagttctgc cctctgctca gccagtcctt gctgttgctg ggggagtcac    4380
acagctccct aatcacgtgg tgaatgtggt accagcccct tcagcgaata gcccagtgaa    4440
tggaaaactt tccgtgacta aacctgtcct acaaagtacc atgagaaatg tcggttcaga    4500
tattgctgtg ctaaggagac agcaacgtat gataaaaaat cgagaatccg cttgtcagtc    4560
tcgcaagaag aagaaagaat atatgctagg gttagaggcg agattaaagg ctgccctctc    4620
agaaaacgag caactgaaga agaaaatgg aacactgaag cggcagctgg atgaagttgt    4680
gtcagagaac cagaggcttt acccatacga tgttccagat tacgcaatgt aaagagccac    4740
ataacactgg gccccttttcc ctgaccatca cattgcctag aggatagcat aggcctgaag    4800
ggcgaattcc agcacactgg cggccgttac tagagggccc gtttaaaccc gctgatcacc    4860
tcgactgtgc cttctagttg ccagccatct gttgtttgcc cctcccccgt gccttccttg    4920
accctggaag gtgccactcc cactgtcctt tcctaataaa atgaggaaat tgcatcgcat    4980
tgtctgagta ggtgtcattc tattctgggg ggtggggtgg ggcaggacag caaggggggag    5040 gattgggaag acaatagcag gcatgcctgc agcggtccgg tcgactctag aggatccgaa    5100
aaaacctccc acacctcccc ctgaacctga acataaaat gaatgcaatt gttgttgtta    5160
acttgtttat tgcagcttat aatggttaca aataaagcaa tagcatcaca aatttcacaa    5220
ataaagcatt ttttcactg cattctagtt gtggtttgtc caaactcatc aatgtatctt    5280
atcatgtctg gatccccgcg gtggcggccg cactagtccc gggttaatta agctagcaga    5340
tcttgatcac ctaggcgtac gatttggccg ctttacatgg tggcgaccgg ggatcctcta    5400
gtaccaagct aattcctcac gacacctgaa atggaagaaa aaaactttga accactgtct    5460
gaggcttgag aatgaaccaa gatccaaact caaaagggc aaattccaag gagaattaca    5520
tcaagtgcca agctggccta acttcagtct ccacccactc agtgtgggga aactccatcg    5580
cataaaaccc ctcccccaa cctaaagacg acgtactcca aaagctcgag aactaatcga    5640
ggtgcctgga cggcgcccgg tactccgtgg agtcacatga agcgacggct gaggacggaa    5700 aggcccttt cctttgtgtg ggtgactcac ccgcccgctc tcccgagcgc cgcgtcctcc    5760
attttgagct ccctgcagca gggccgggaa gcggccatct ttccgctcac gcaactggtg    5820
ccgaccgggc cagccttgcc gcccagggcg gggcgataca cggcggcgcg aggccaggca    5880
ccagagcagg ccggccagct tgagactacc cccgtccgat tctcggtggc cgcgctcgca    5940
ggccccgcct cgccgaacat gtgcgctggg acgcacgggc ccgtcgccg cccgcggccc    6000 caaaaaccga atacccagtg tgcagatctt ggcccgcatt tacaagacta tcttgccaga    6060
aaaaaagcgt cgcagcaggt catcaaaaat tttaaatggc tagagactta tcgaaagcag    6120
cgagacaggc gcgaaggtgc caccagattc gcacgcggcg gccccagcgc ccaggccagg    6180
cctcaactca gcacgaggc gaaggggctc cttaagcgca aggcctcgaa ctctcccacc    6240
cacttccaac ccgaagctcg ggatcaagaa tcacgtactg cagccaggtg gaagtaattc    6300
aaggcacgca agggccataa cccgtaaaga ggccaggccc gcgggaacca cacacggcac    6360
```

```
ttacctgtgt tctggcggca aacccgttgc gaaaaagaac gttcacggcg actactgcac    6420
ttatatacgg ttctccccca ccctcgggaa aaggcggag ccagtacacg acatcacttt    6480
cccagtttac cccgcgccac cttctctagg caccgg                              6516

<210> SEQ ID NO 14
<211> LENGTH: 6537
<212> TYPE: DNA
<213> ORGANISM: Artificial Sequence
<220> FEATURE:
<223> OTHER INFORMATION: pAAV_XBP1s-HA

<400> SEQUENCE: 14
ggcggatcca attgcctagg cccaagggcg aattgtcacg actccacccc tccaggaacc      60
cctagtgatg gagttggcca ctccctctct gcgcgctcgc tcgctcactg aggccgcccg     120
ggcaaagccc gggcgtcggg cgacctttgg tcgcccggcc tcagtgagcg agcgagcgcg     180
cagagaggga gtggcccaga tctgatatca tcgatgaatt caagcttcag ctgctcgagt     240
tctatagtgt cacctaaatc gtatgtgtat gatacataag gttatgtatt aattgtagcc     300
gcgttctaac gacaatatgt ccatatggtg cactctcagt acaatctgct ctgatgccgc     360
atagttaagc cagccccgac acccgccaac acccgctgac gcgccctgac gggcttgtct     420
gctcccggca tccgcttaca gacaagctgt gaccgtctcc gggagctgca tgtgtcagag     480
gttttcaccg tcatcaccga aacgcgcgag acgaaagggc ctcgtgatac gcctattttt     540
ataggttaat gtcatgataa taatggtttc ttagacgtca ggtggcactt ttcggggaaa     600
tgtgcgcgga acccctattt gtttattttt ctaaatacat tcaaatatgt atccgctcat     660
gagacaataa ccctgataaa tgcttcaata atattgaaaa aggaagagta tgagtattca     720
acatttccgt gtcgccctta ttccctttt tgcggcattt gccttcctg ttttgctca      780 cccagaaacg ctggtgaaag taaaagatgc tgaagatcag ttgggtgcac gagtgggtta     840
catcgaactg gatctcaaca gcggtaagat ccttgagagt tttcgccccg aagaacgttt     900
tccaatgatg agcactttta aagttctgct atgtggcgcg gtattatccc gtattgacgc     960
cgggcaagag caactcggtc gccgcataca ctattctcag aatgacttgg ttgagtactc    1020
accagtcaca gaaaagcatc ttacggatgg catgacagta agagaattat gcagtgctgc    1080
cataaccatg agtgataaca ctgcggccaa cttacttctg acaacgatcg gaggaccgaa    1140
ggagctaacc gcttttttgc acaacatggg ggatcatgta actcgccttg atcgttggga    1200
accggagctg aatgaagcca taccaaacga cgagcgtgac accacgatgc ctgtagcaat    1260
ggcaacaacg ttgcgcaaac tattaactgg cgaactactt actctagctt cccggcaaca    1320
attaatagac tggatggagg cggataaagt tgcaggacca cttctgcgct cggcccttcc    1380
ggctggctgg tttattgctg ataaatctgg agccggtgag cgtgggtctc gcggtatcat    1440
tgcagcactg gggccagatg gtaagccctc ccgtatcgta gttatctaca cgacggggag    1500
tcaggcaact atggatgaac gaaatagaca gatcgctgag ataggtgcct cactgattaa    1560
gcattggtaa ctgtcagacc aagtttactc atatatactt tagattgatt taaaacttca    1620
tttttaattt aaaaggatct aggtgaagat cctttttgat aatctcatga ccaaaatccc    1680
ttaacgtgag ttttcgttcc actgagcgtc agaccccgta gaaaagatca aggatcttc    1740 ttgagatcct ttttttctgc gcgtaatctg ctgcttgcaa acaaaaaaac caccgctacc    1800
agcggtggtt tgtttgccgg atcaagagct accaactctt tttccgaagg taactggctt    1860
```

| | |
|---|---|
| cagcagagcg cagataccaa atactgtcct tctagtgtag ccgtagttag gccaccactt | 1920 |
| caagaactct gtagcaccgc ctacatacct cgctctgcta atcctgttac cagtggctgc | 1980 |
| tgccagtggc gataagtcgt gtcttaccgg gttggactca agacgatagt taccggataa | 2040 |
| ggcgcagcgt tcgggctgaa cggggggttc gtgcacacag cccagcttgg agcgaacgac | 2100 |
| ctacaccgaa ctgagatacc tacagcgtga gcattgagaa agcgccacgc ttcccgaagg | 2160 |
| gagaaaggcg gacaggtatc cggtaagcgg cagggtcgga acaggagagc gcacgaggga | 2220 |
| gcttccaggg ggaaacgcct ggtatcttta tagtcctgtc gggtttcgcc acctctgact | 2280 |
| tgagcgtcga ttttgtgat gctcgtcagg ggggcggagc ctatggaaaa acgccagcaa | 2340 |
| cgcggccttt ttacggttcc tggcctttg ctggcctttt gctcacatgt tctttcctgc | 2400 |
| gttatcccct gattctgtgg ataaccgtat taccgccttt gagtgagctg ataccgctcg | 2460 |
| ccgcagccga acgaccgagc gcagcgagtc agtgagcgag gaagcggaag agcgcccaat | 2520 |
| acgcaaaccg cctctccccg cgcgttggcc gattcattaa tgcaggttaa cctggcttat | 2580 |
| cgaaattaat acgactcact ataggagac cggcagatct gtccctctct gcgcgctcgc | 2640 |
| tcgctcactg aggccgcccg ggcaaagccc gggcgtcggg cgacctttgg tcgcccggcc | 2700 |
| tcagtgagcg agcgagcgcg cagagaggga gtggccaact ccatcactag ggttccttg | 2760 |
| tagttaatga ttaacccgcc atgctactta tctacaattc gcccttcgga cgcgtggctt | 2820 |
| cgaactaggc aattgcatga agaatctgct tagggttagg cgttttgcgc tgcttcgcga | 2880 |
| tgtacgggcc agatatacgc gttgacattg attattgact agttattaat agtaatcaat | 2940 |
| tacgggtca ttagttcata gcccatatat ggagttccgc gttacataac ttacggtaaa | 3000 |
| tggcccgcct ggctgaccgc ccaacgaccc ccgcccattg acgtcaataa tgacgtatgt | 3060 |
| tcccatagta acgccaatag ggactttcca ttgacgtcaa tgggtggagt atttacggta | 3120 |
| aactgcccac ttggcagtac atcaagtgta tcatatgcca agtacgcccc ctattgacgt | 3180 |
| caatgacggt aaatggcccg cctggcatta tgcccagtac atgaccttat gggactttcc | 3240 |
| tacttggcag tacatctacg tattagtcat cgctattacc atggtgatgc ggttttggca | 3300 |
| gtacatcaat gggcgtggat agcggtttga ctcacgggga tttccaagtc tccaccccat | 3360 |
| tgacgtcaat gggagtttgt tttggcacca aaatcaacgg gactttccaa aatgtcgtaa | 3420 |
| caactccgcc ccattgacgc aaatgggcgg taggcgtgta cggtgggagg tctatataag | 3480 |
| cagagctctc tggctaacta gagaacccac tgcttactgg cttatcgaaa ttaatacgac | 3540 |
| tcactatagg gagacccaag ctggctagcg tttaaactta agcttcctgg ctatggtggt | 3600 |
| ggtggcagcc gcgccgaacc cggccgacgg gaccctaaa gttctgcttc tgtcggggca | 3660 |
| gcccgcctcc gccgccggag ccccggccgg ccaggccctg ccgctcatgg tgccagccca | 3720 |
| gagagggcc agcccggagg cagcgagcgg ggggctgccc caggcgcgca agcgacagcg | 3780 |
| cctcacgcac ctgagccccg aggagaaggc gctgaggagg aaactgaaaa acagagtagc | 3840 |
| agctcagact gccagagatc gaaagaaggc tcgaatgagt gagctggaac agcaagtggt | 3900 |
| agatttagaa gaagagaacc aaaaactttt gctagaaaat cagcttttac gagagaaaac | 3960 |
| tcatggcctt gtagttgaga accaggagtt aagcagcgc ttggggatgg atgccctggt | 4020 |
| tgctgaagag gaggcggaag ccaaggggaa tgaagtgagg ccagtggccg ggtctgctga | 4080 |
| gtccgcagca ggtgcaggcc cagttgtcac ccctccagaa catctcccca tggattctgg | 4140 |
| cggtattgac tcttcagatt cagagtctga tatcctgttg ggcattctgg acaacttgga | 4200 |
| cccagtcatg ttcttcaaat gcccttcccc agagcctgcc agcctggagg agctcccaga | 4260 |

```
ggtctaccca gaaggaccca gttccttacc agcctcsccctt tctctgtcag tggggacgtc    4320
atcagccaag ctggaagcca ttaatgaact aattcgtttt gacccacatat ataccaagcc    4380
cctagtctta gagataccct ctgagacaga gagccaagct aatgtggtag tgaaaatcga    4440
ggaagcacct ctcagcccct cagagaatga tcaccctgaa ttcattgtct cagtgaagga    4500
agaacctgta gaagatgacc tcgttccgga gctgggtatc tcaaatctgc tttcatccag    4560
ccactgccca aagccatctt cctgcctact ggatgcttac agtgactgtg gatacgggg    4620
ttccctttcc ccattcagtg acatgtcctc tctgcttggt gtaaaccatt cttgggagga    4680
cactttttgcc aatgaactct ttccccagct gattagtgtc tacccatacg atgttccaga    4740
ttacgcaatg taaagagcca cataacactg ggcccctttc cctgaccatc acattgccta    4800
gaggatagca taggcctgaa gggcgaattc cagcacactg gcggccgtta ctagagggcc    4860
cgtttaaacc cgctgatcac ctcgactgtg ccttctagtt gccagccatc tgttgtttgc    4920
ccctcccccg tgccttcctt gaccctggaa ggtgccactc ccactgtcct ttcctaataa    4980
aatgaggaaa ttgcatcgca ttgtctgagt aggtgtcatt ctattctggg gggtggggtg    5040
gggcaggaca gcaaggggga ggattgggaa gacaatagca ggcatgcctg cagcggtccg    5100
gtcgactcta gaggatccga aaaaacctcc cacacctccc cctgaacctg aaacataaaa    5160
tgaatgcaat tgttgttgtt aacttgttta ttgcagctta taatggttac aaataaagca    5220
atagcatcac aaatttcaca aataaagcat ttttttcact gcattctagt tgtggtttgt    5280
ccaaactcat caatgtatct tatcatgtct ggatccccgc ggtggcggcc gcactagtcc    5340
cgggttaatt aagctagcag atcttgatca cctaggcgta cgatttggcc gctttacatg    5400
gtggcgaccg gggatcctct agtaccaagc taattcctca cgacacctga atggaagaa    5460
aaaaactttg aaccactgtc tgaggcttga gaatgaacca agatccaaac tcaaaaaggg    5520
caaattccaa ggagaattac atcaagtgcc aagctggcct aacttcagtc tccacccact    5580
cagtgtgggg aaactccatc gcataaaacc cctccccccca acctaaagac gacgtactcc    5640
aaaagctcga gaactaatcg aggtgcctgg acggcgcccg gtactccgtg gagtcacatg    5700
aagcgacggc tgaggacgga aaggcccttt tcctttgtgt gggtgactca cccgcccgct    5760
ctcccgagcg ccgcgtcctc cattttgagc tccctgcagc agggccggga agcggccatc    5820
tttccgctca cgcaactggt gccgaccggg ccagccttgc cgcccagggc ggggcgatac    5880
acggcggcgc gaggccaggc accagagcag gccggccagc ttgagactac ccccgtccga    5940
ttctcggtgg ccgcgctcgc aggccccgcc tcgccgaaca tgtgcgctgg gacgcacggg    6000
ccccgtcgcc gcccgcggcc ccaaaaaccg aaataccagt gtgcagatct tggcccgcat    6060
ttacaagact atcttgccag aaaaaaagcg tcgcagcagg tcatcaaaaa ttttaaatgg    6120
ctagagactt atcgaaagca gcgagacagg cgcgaaggtg ccaccagatt cgcacgcggc    6180
ggccccagcg cccaggccag gcctcaactc aagcacgagg cgaagggct ccttaagcgc    6240
aaggcctcga actctcccac ccacttccaa cccgaagctc gggatcaaga atcacgtact    6300
gcagccaggt ggaagtaatt caaggcacgc aagggccata acccgtaaag aggccaggcc    6360
cgcgggaacc acacacggca cttacctgtg ttctggcggc aaacccgttg cgaaaaagaa    6420
cgttcacggc gactactgca cttatatacg gttctccccc accctcggga aaaaggcgga    6480
gccagtacac gacatcactt tcccagttta ccccgcgcca ccttctctag gcaccgg     6537
```

<210> SEQ ID NO 15

```
<211> LENGTH: 20
<212> TYPE: DNA
<213> ORGANISM: Artificial Sequence
<220> FEATURE:
<223> OTHER INFORMATION: Primer Erdj4 forward

<400> SEQUENCE: 15
ggaaggagga gcgctaggtc                                                      20

<210> SEQ ID NO 16
<211> LENGTH: 20
<212> TYPE: DNA
<213> ORGANISM: Artificial Sequence
<220> FEATURE:
<223> OTHER INFORMATION: Primer Erdj4 reverse

<400> SEQUENCE: 16
atcctgcacc ctccgactac                                                      20

<210> SEQ ID NO 17
<211> LENGTH: 21
<212> TYPE: DNA
<213> ORGANISM: Artificial Sequence
<220> FEATURE:
<223> OTHER INFORMATION: Primer HspA5 (BiP) forward

<400> SEQUENCE: 17
gcctgtattt ctagacctgc c                                                    21

<210> SEQ ID NO 18
<211> LENGTH: 20
<212> TYPE: DNA
<213> ORGANISM: Artificial Sequence
<220> FEATURE:
<223> OTHER INFORMATION: Primer HspA5 (BiP) reverse

<400> SEQUENCE: 18
ttcatcttgc cagccagttg                                                      20

<210> SEQ ID NO 19
<211> LENGTH: 20
<212> TYPE: DNA
<213> ORGANISM: Artificial Sequence
<220> FEATURE:
<223> OTHER INFORMATION: Primer HerpUD forward

<400> SEQUENCE: 19
aacggcatgt tttgcatctg                                                      20

<210> SEQ ID NO 20
<211> LENGTH: 20
<212> TYPE: DNA
<213> ORGANISM: Artificial Sequence
<220> FEATURE:
<223> OTHER INFORMATION: Primer HerpUD reverse

<400> SEQUENCE: 20
ggggaagaaa ggttccgaag                                                      20

<210> SEQ ID NO 21
<211> LENGTH: 20
<212> TYPE: DNA
<213> ORGANISM: Artificial Sequence
<220> FEATURE:
<223> OTHER INFORMATION: Primer Hyou 1 forward

<400> SEQUENCE: 21
```

```
gcagacctgt tggcactgag                                                 20

<210> SEQ ID NO 22
<211> LENGTH: 20
<212> TYPE: DNA
<213> ORGANISM: Artificial Sequence
<220> FEATURE:
<223> OTHER INFORMATION: Primer Hyou 1 reverse

<400> SEQUENCE: 22
tcacgatcac cggtgttttc                                                 20

<210> SEQ ID NO 23
<211> LENGTH: 20
<212> TYPE: DNA
<213> ORGANISM: Artificial Sequence
<220> FEATURE:
<223> OTHER INFORMATION: Primer Pdia4 forward

<400> SEQUENCE: 23
agtggggagg atgtcaatgc                                                 20

<210> SEQ ID NO 24
<211> LENGTH: 20
<212> TYPE: DNA
<213> ORGANISM: Artificial Sequence
<220> FEATURE:
<223> OTHER INFORMATION: Primer Pdia4 reverse

<400> SEQUENCE: 24
tggctgggat ttgatgactg                                                 20

<210> SEQ ID NO 25
<211> LENGTH: 20
<212> TYPE: DNA
<213> ORGANISM: Artificial Sequence
<220> FEATURE:
<223> OTHER INFORMATION: Primer Sec24D forward

<400> SEQUENCE: 25
agcagactgt cctgggaagc                                                 20

<210> SEQ ID NO 26
<211> LENGTH: 20
<212> TYPE: DNA
<213> ORGANISM: Artificial Sequence
<220> FEATURE:
<223> OTHER INFORMATION: Primer Sec24D reverse

<400> SEQUENCE: 26
tttgtttggg gctggaaaag                                                 20

<210> SEQ ID NO 27
<211> LENGTH: 20
<212> TYPE: DNA
<213> ORGANISM: Artificial Sequence
<220> FEATURE:
<223> OTHER INFORMATION: Primer Sel1L forward

<400> SEQUENCE: 27
atctccaaaa ggcagcaagc                                                 20

<210> SEQ ID NO 28
<211> LENGTH: 20
<212> TYPE: DNA
```

```
<213> ORGANISM: Artificial Sequence
<220> FEATURE:
<223> OTHER INFORMATION: Primer Sel1L reverse

<400> SEQUENCE: 28
tgggagagcc ttcctcagtc                                              20

<210> SEQ ID NO 29
<211> LENGTH: 20
<212> TYPE: DNA
<213> ORGANISM: Artificial Sequence
<220> FEATURE:
<223> OTHER INFORMATION: Primer Stt3a forward

<400> SEQUENCE: 29
ttcaacctgg gtgaccagtg                                              20

<210> SEQ ID NO 30
<211> LENGTH: 20
<212> TYPE: DNA
<213> ORGANISM: Artificial Sequence
<220> FEATURE:
<223> OTHER INFORMATION: Primer Stt3a reverse

<400> SEQUENCE: 30
catgaccttc gcatcctctg                                              20

<210> SEQ ID NO 31
<211> LENGTH: 20
<212> TYPE: DNA
<213> ORGANISM: Artificial Sequence
<220> FEATURE:
<223> OTHER INFORMATION: Primer Sulf1 forward

<400> SEQUENCE: 31
attcaaggag gctgctcagg                                              20

<210> SEQ ID NO 32
<211> LENGTH: 20
<212> TYPE: DNA
<213> ORGANISM: Artificial Sequence
<220> FEATURE:
<223> OTHER INFORMATION: Primer Sulf1 reverse

<400> SEQUENCE: 32
tgtcatgcgt gaagcaagtg                                              20
```

AAV/UPR-PLUS VIRUS, UPR-PLUS FUSION PROTEIN, GENETIC TREATMENT METHOD AND ITS USE IN THE TREATMENT OF NEURODEGENERATIVE DISEASES, SUCH AS PARKINSON'S DISEASE AND HUNTINGTON'S DISEASE, AMONG OTHERS

CROSS-REFERENCE TO RELATED APPLICATIONS

This application is a Continuation Application of U.S. application Ser. No. 15/773,723 filed May 4, 2018, which is a U.S. National Stage entry of PCT Application No: PCT/CL2016/000070 filed Nov. 4, 2016, which claims priority to Chilean Patent Application No. 3242-2015 filed Nov. 4, 2015, the contents of which are incorporated herein by reference.

TECHNICAL FIELD OF THE PRESENT INVENTION

The present invention applies to the field of medicine, specifically in the treatment of neurodegenerative diseases, through the use of adeno-associated viruses (AAVs) that overexpress the fusion protein between XBP1s, a linker peptide and ATF6f in neurons of the central nervous system (CNS), recovering and improving neurodegenerative problems, preferably Parkinson's and Huntington's diseases.

PRIOR ART BACKGROUND AND DESCRIPTION

Scientific research on CNS diseases has been of great interest in recent years, especially diseases related to cognitive and motor disorders. The treatment of diseases related to neurodegenerative problems does not currently have genetic therapeutic approaches to reduce symptoms.

In the search for the treatment of these motor and cognitive diseases, two transcription factors called XBP1 and ATF6 have been identified. They are involved in the biological and molecular mechanisms for improving protein folding and aggregation processes. Mainly the new fusion protein aims to activate the transcription of gene clusters involved in improving protein folding. Then, reduce their aggregation by reprogramming the transcription of the specific genes involved in protein folding, such as chaperones. The phenomenon of protein aggregation is a common feature in neurodegenerative diseases and a cause for selective neuronal death.

Today's existing pharmacological therapies are only palliative, since they are focused on reducing the symptoms of patients suffering from these diseases and fail to stop the selective death of neurons. They generally consist of pharmacological therapies that regulate the levels of altered neurotransmitters because of the death of fundamental neuronal groups, which ensure the correct functioning of the brain. An example of this type of therapy is the administration of L-dopa and its pharmacological derivatives to Parkinson's patients. This compound is capable of restoring dopamine levels in patients, but does not stop the selective death of dopaminergic neurons causing this disease. The present proposal focuses on curbing neuronal death by means of gene therapy and producing an effective and definitive treatment for this type of pathology.

There are other pathologies related to neuro-motor diseases such as Huntington's disease, where their treatments are limited or non-existent. This disease is a dominant hereditary neurodegenerative pathology caused by a mutation of the IT15 gene, coding the Huntingtin protein. The mutation results in the expansion of a poly-glutamine segment at the N-terminal end of the protein, which generates protein aggregates in the mid-spinal neurons (MSNs) of the striatum region. This triggers neural degeneration and symptoms characteristic of the disease, such as progressive loss of voluntary muscle movement control (chorea), psychiatric symptoms and dementia (Atwal, 2007).

To date, the proposal for the use of a synthetic fusion protein has not been generally addressed. There are publications such as WO2004/111194 and WO2006/028889, which point to the formation of recombinant proteins that encode for XBP1, elF2α, S51A and ATF (Post-deletion forms by splicing), separated, not as a fusion protein, which does not seek to optimize the improvement in the control of neurodegenerative diseases in a single construct. On the other hand, there are individual documents that point to the endogenous decrease of XBP1, as presented in patent US2013197023, which correlates with an increased folding capacity of the endoplasmic reticulum (ER) which is required to maintain cellular homeostasis. This individual negative regulation of XBP1 expression has been implicated in the generation of neuroprotection in Huntington's disease and amyotrophic lateral sclerosis (ALS), as filed in patent application WO2010/008860.

Another relevant patent regarding the measurement of ER stress, where the transcription factor XBP1 is involved, is the Japanese patent JP2007129970.

In general, this development refers to the synthesis and viability of a new peptide conformed by XBP1 s, a linker peptide and ATF6f for the treatment of neurodegenerative diseases such as Parkinson's Disease and Huntington's Disease, without being restricted to these alone.

One of the patents nearing this approach is the Chilean patent application 3590-2014, which presents a genetic treatment method to improve memory with a recombinant virus AAV/XBP1S-HA. This treatment brings the XBP1 s-HA peptide closer to improving a cognitive function, but not for treating a disease. On the other hand, there is no talk of a functional fusion protein that involves XBP1s within its components.

INVENTION SUMMARY

Recent studies indicate that the chronic alteration of protein homeostasis in the ER (Endoplasmic Reticulum) is a transversal pathological event observed in practically all neurodegenerative diseases associated with protein folding disorders, such as Alzheimer's disease, Parkinson's disease, Huntington's disease, Amyotrophic Lateral Sclerosis, among others.

Different conditions interfere with the protein synthesis and folding process in the ER's lumen, resulting in an abnormal accumulation of misfolded proteins. This condition, called ER stress, can be promoted by the expression of certain mutant proteins, as well as by the alteration in the process of protein synthesis and maturation. In response to this phenomenon, an integrated intracellular signaling cascade called UPR is activated. Activation of UPR results in different changes in gene expression that have global effects on protein homeostasis, decreasing, for example, the levels of abnormal aggregation and protein misfolding resulting from:

(i) an increased expression of chaperones and foldases;
(ii) improved protein quality control; and
(iii) mass removal of defective proteins.

The UPR's initial objective is to recover the protein balance, maintaining cell viability. However, chronic ER stress leads to cell death by apoptosis, a phenomenon observed in several neurodegenerative pathologies.

The initial UPR phase is mediated by three ER "stress sensors":

1) PERK (double-stranded RNA activated protein kinase [PKR] such as endoplasmic reticulum kinase);
2) ATF6 (activating transcription factor 6); and
3) IRE1 (inositol requiring kinase 1)

Each of these sensors relays information on the folding state in the ER lumen to the nucleus by controlling specific transcription factors, where XBP1 stands out (X-Box binding protein-1). XBP1 regulates a series of genes involved in protein quality control, folding, among other processes. These three adaptive pathways act in unison, maintaining protein homeostasis and cell survival. Unlike the ATF6 and XBP1-dependent responses, signaling mediated by the PERK sensor has also been associated with pro-apoptotic effects. These previous definitions have collaborated in developing this project to define the impact of UPR in the treatment of neurodegenerative diseases, in addition to designing new animal models to measure these responses.

Previous evidence has described that a gain in XBP1 function slows the neurodegenerative process in animal models of three neurodegenerative diseases: Huntington's disease, Parkinson's disease and amyotrophic lateral sclerosis. On the other hand, it has also been determined that ATF6 transcription factor deficiency causes a loss of resistance to neuronal death in preclinical models of Parkinson's disease. These antecedents indicate the importance of these transcription factors in neurodegenerative processes due to the formation of toxic protein aggregates. Therefore, UPR-plus® is based on the fusion of two active components of UPR, such as XBP1, ATF6 and a linker peptide.

Currently UPRplus has been developed and presents specific transcriptional activity of a group (cluster) of genes related to UPR. UPRplus is a fusion protein and is potentially able to participate in the process of relieving the burden of toxic protein aggregates in neurons.

A first aspect of the present invention is related to a method for the treatment of neurodegenerative diseases in cognitive and motor processes in mammals, preferably in humans, using a virus that induces a neuronal overexpression of UPRplus in the central nervous system.

A second aspect of the present invention provides a method to treat neurodegenerative diseases in cognitive and motor processes. The method involves intravenous and/or intraperitoneal and/or intracranial and/or intramedullary and/or intranasal and/or intraneural and/or any pathway that introduces the virus into the brain past the blood-brain barrier of a patient or subject. The virus induces neuronal overexpression of UPRplus in a dose range of $1 \times 10^6$ to $1 \times 10^{30}$ viral units per individual.

A third aspect of the present invention is a form of intravenous and/or intraperitoneal and/or intracranial and/or intramedullary and/or intranasal and/or intranasal and/or intraneural pharmaceutical composition and/or any form that conducts the virus inducing the neuronal overexpression of UPRplus to the brain, passing the blood-brain barrier, with dose ranges as those previously described and a pharmaceutically acceptable vehicle for its use in the treatment of a neurodegenerative disease.

A fourth aspect of the present invention is the use of a virus that induces the neuronal overexpression of UPRplus and its protein-derived compounds, because it can be used to prepare a useful drug for the treatment of a neurodegenerative disease cognitive and motor skills.

A fifth aspect of the present invention is an adeno-associated virus (AAV) with a sequence of the virus and an insert with a nucleotide sequence described in Table I or any of its variants, contained in the bacterium *Escherichia coli*, and transformed with the plasmid deposited in the International Biological Deposits Organization, Institute de Investigaciones Agropecuarias de Chile (Chilean Agricultural Research Institute—INIA), under deposit number RGM 2235, where the XBP1s-LFG-ATF6f (UPR-Plus 5) neural transcription factor is overexpressed, preferably in the central nervous system or any variant of the fragment, which encodes or overexpresses this alternative to the neural transcription factor of UPRplus in mammals, preferably in humans.

A sixth aspect of the present invention is an adeno-associated virus (AAV) with a sequence of the virus and an insert with a nucleotide sequence described in Table II or any of its variants, contained in the bacterium *Escherichia coli* and transformed with the plasmid deposited in the International Biological Deposits Organization, Institute de Investigaciones Agropecuarias de Chile (INIA), under deposit number RGM 2234, where the XBP1s-LF-ATF6f (UPR-Plus 4) neural transcription factor is overexpressed, preferably in the central nervous system or any variant of the fragment, which encodes or overexpresses this alternative to the neural transcription factor of UPRplus in mammals, preferably in humans.

A seventh aspect of the present invention is an adeno-associated virus (AAV) with a sequence of the virus and an insert with a nucleotide sequence described in Table III or any of its variants, contained in the bacterium *Escherichia coli* and transformed with the plasmid deposited in the International Biological Deposits Organization, Institute de Investigaciones Agropecuarias de Chile (INIA), under deposit number RGM 2236, where the XBP1s-L4H4-ATF6f (UPR-Plus 6) neural transcription factor is overexpressed, preferably in the central nervous system or any variant of the fragment, which encodes or overexpresses this alternative to the neural transcription factor of UPRplus in mammals, preferably in humans.

An eighth aspect of the present invention is an adeno-associated virus (AAV) with a sequence of the virus and an insert with a nucleotide sequence described in Table IV or any of its variants, contained in the bacterium *Escherichia coli* and transformed with the plasmid deposited in the International Biological Deposits Organization, Instituto de Investigaciones Agropecuarias de Chile (INIA), under deposit number RGM 2232, where the ATF6f-LFG-XBP1s (UPR-Plus 2) neural transcription factor is overexpressed, preferably in the central nervous system or any variant of the fragment, which encodes or overexpresses this alternative to the neural transcription factor of UPRplus in mammals, preferably in humans.

A ninth aspect of the present invention is an adeno-associated virus (AAV) with a sequence of the virus and an insert with a nucleotide sequence described in Table V or any of its variants, contained in the bacterium *Escherichia coli* and transformed with the plasmid deposited in the International Biological Deposits Organization, Instituto de Investigaciones Agropecuarias de Chile (INIA), under deposit number RGM 2233, where the ATF6f-L4H4-XBP1s (UPR-Plus 3) neural transcription factor is overexpressed, preferably in the central nervous system or any variant of the fragment, which encodes or overexpresses this alternative to the neural transcription factor of UPRplus in mammals, preferably in humans.

A tenth aspect of the present invention is an adeno-associated virus (AAV) with a sequence of the virus and an insert with a nucleotide sequence described in Table VI or any of its variants, contained in the bacterium *Escherichia coli* and transformed with the plasmid deposited in the International Biological Deposits Organization, Instituto de Investigaciones Agropecuarias de Chile (INIA), under deposit number RGM 2231, where the ATF6f-LF-XBP1s (UPR-Plus 1) neural transcription factor is overexpressed, preferably in the central nervous system or any variant of the fragment, which encodes or overexpresses this alternative to the neural transcription factor of UPRplus in mammals, preferably in humans.

Microorganism Deposit

Plasmid pAAV_ATF6f-LFG-XBP1s-HA was deposited on Oct. 7, 2015 at the International Biological Deposits Organization, Instituto de Investigaciones Agropecuarias de Chile (INIA), under deposit number RGM 2232.

Plasmid pAAV_ATF6f-LF-XBP1s-HA was deposited on Oct. 7, 2015 at the International Biological Deposits Organization, Institute de Investigaciones Agropecuarias de Chile (INIA), under deposit number RGM 2231.

Plasmid pAAV_ATF6f-L4H4-XBP1s-HA was deposited on Oct. 7, 2015 at the International Biological Deposits Organization, Institute de Investigaciones Agropecuarias de Chile (INIA), under deposit number RGM 2233.

Plasmid pAAV_XBP1s-LFG-ATF6f-HA was deposited on Oct. 7, 2015 at the International Biological Deposits Organization, Institute de Investigaciones Agropecuarias de Chile (INIA), under deposit number RGM 2235.

Plasmid pAAV_XBP1s-LF-ATF6f-HA was deposited on Oct. 7, 2015 at the International Biological Deposits Organization, Institute de Investigaciones Agropecuarias de Chile (INIA), under deposit number RGM 2234.

Plasmid pAAV_XBP1s-L4H4-ATF6f-HA was deposited on Oct. 7, 2015 at the International Biological Deposits Organization, Institute de Investigaciones Agropecuarias de Chile (INIA), under deposit number RGM 2236.

DETAILED DESCRIPTION OF THE INVENTION

It should be noted that the present invention is not limited to the particular methodology, composites, materials, manufacturing techniques, uses and applications described herein, as these may vary. It should also be understood that the terminology used herein is used for the sole purpose of describing a particular representation and is not intended to limit the invention's perspective and potential.

It should be noted that the use and method of the singular, as expressed in the set of claims and throughout the text, does not exclude the plural, unless within a context that clearly implies it. So, for example, the reference to a "use or method" is a reference to one or more uses or methods and includes equivalents known to those who are knowledgeable of the subject matter (art). Similarly, as another example, the reference to "one step", "one stage" or "one mode" is a reference to one or more steps, stages or modes and may include sub-steps, stages or modes, implicit and/or consequential.

All conjunctions are to be understood in their least restrictive and most inclusive sense possible. Thus, for example, the conjunction 'or' must be understood in its orthodox logical sense, and not as 'or excluding', unless the context or text expressly requires or indicates this. The structures, materials and/or elements described herein are also to be understood as references to functional equivalents to avoid endless, exhaustive enumerations.

Expressions used to indicate approximations or conceptualizations should be understood as stated herein, unless the context requires a different interpretation.

All the names and technical and/or scientific terms used herein have the common meaning as given to them by a common person, qualified in these matters, unless expressly indicated otherwise.

Methods, techniques, elements, compounds and compositions are described, although methods, techniques, compounds and compositions similar and/or equivalent to those described may be used or preferred in practice and/or in tests for the present invention.

All patents and other publications are cross-referenced for the purpose of describing and/or informing; for example, the methodologies described in such publications, which may be useful in connection with the present invention.

These publications are included only for their pre-patent information, prior to the date of registration of this patent application.

In this regard nothing shall be construed as an admission or acceptance, rejection or exclusion that the authors and/or inventors are not entitled to be so, or that such publications are dated in advance by virtue of previous ones, or for any other reason.

The present invention describes vectors based on serotypes AAV2, AAV6, AAV7, AAV8, AAV9, AAV10, AAV10, AAV11 and pseudo-typed AAVs and from adeno-associated viruses capable of efficiently mediating gene transfer to the central nervous system.

The systemic administration of these vectors also leads to an efficient gene supply to both the brain and spinal cord. The present invention claims that the AAV2 vector with proximal regions of the UPRplus transcription factor promoter allows the generation of a nonspecific response in a cluster of factors in the brain and spine. In particular, the local administration of the AAV2 vector, which comprises a series of expression cassettes in which the heterologous genes XBP1s and ATF6f are under the control of the CMV promoter, improving motor and cognitive abilities in individuals suffering from neurodegenerative mediated diseases. (FIGS. 16 and 17).

I. Definition of General Terms and Expressions

The terms "adeno-associated virus", "AAV virus", "AAV virion", "AAV viral particle", and "AAV particle" as used in this document are interchangeable. They refer to a viral particle composed of at least one AAV capsid protein (preferably all capsid proteins of a particular AAV serotype) and one encapsulated AAV genome polynucleotide. If the particle comprises a heterologous polynucleotide (i.e., a polynucleotide other than a native-type AAV genome such as a transgene to be delivered to a mammalian cell) flanked by inverted terminal repeats of the AAV, which is typically referred to as an 'AAV particle vector' or 'AAV vector'. AAV refers to viruses belonging to the Dependovirus genus of the Parvoviridae family. The AAV genome is approximately 4.7 kilobases long and is composed of single-chain deoxyribonucleic acid (ssDNA) that can be counted as positive or negative. The genome comprises inverted terminal repeats (ITRs) at both ends of the DNA chain, and two open reading frames (ORFs): REP and CAP (Replicase and Capside). The REP framework consists of four overlapping genes that encode REP proteins (REP 78, REP 68, REP 52 and REP 40) required for the AAV's life cycle. The CAP frame contains overlapping nucleotides of 20 capsid protein sequences: VP1, VP2 and VP3, which interact with each other to form an icosahedral symmetry capsid.

The term "adeno-associated IRT virus" or "AAV IRT", as used herein, refers to the repeating inverted terminal present at both ends of the DNA chain of an adeno-associated virus genome. IRT sequences are required for efficient multiplication of the AAV genome. Another property of these sequences is their ability to form a fork. This feature contributes to its self-copy which allows for independent primary synthesis of the second DNA strand. IRTs also proved to be necessary for both the integration of native AAV DNA into the host cell genome and the rescue of the host cell, as well as for the effective encapsulation of AAV DNA combined with the generation of its complete assembly.

The term 'AAV2', as used in the present invention, refers to serotype 2 of the adeno-associated virus with a genome sequence as defined in GenBank access number AF043303.1, found on the following website: http://www.ncbi.nim.nih.gov/nuccore/AF043303.1.

Currently, about 11 human AAV serotypes and about 100 primate AAV serotypes that can be used as vectors have been reported. Each serotype represents advantages and disadvantages with respect to stability, productivity, immunogenicity, bioavailability, tropism, etc. However, many laboratories have developed pseudo-typical vectors, i.e. modified AAVs containing cover proteins of different serotypes, in order to obtain the advantages of different serotypes or to avoid the disadvantages of some cover proteins of some serotypes. By way of example, an AAV2/6 virus, in which the characteristics of the two viral serotypes are mixed, are sometimes used in the present invention.

The term 'AAV vector', as used in the present invention, also refers to a vector comprising one or more polynucleotides of interest (or transgenes) that are flanked by AAV terminal repetition sequences (ITRs). Such AAV vectors can be replicated and packaged into infectious viral particles when they are present in a host cell that has been transfected with a vector that encodes and expresses the REP and CAP genes (i.e., the REP and CAP AAV proteins), and where the host cell has been transfected with a vector that encodes and expresses a protein from the E4orf6 adenovirus reading frame. When an AAV vector is incorporated into a larger polynucleotide (for example, a chromosome or other vector such as a plasmid used for cloning or transfection), then the AAV vector is typically referred to as a "pro-vector". The pro-vector can be "rescued" by replication and encapsulation in the presence of the AAV packaging functions and the necessary auxiliary functions provided by E4orf6.

The serotype of the AAV vector provides the specificity of the cell type where it will express the transgene given each serotype's tropism.

The term 'specific binding site for the UPRplus transcription regulatory region' as used in the present invention, refers to a nucleic acid sequence that works as a promoter (i.e. regulates the expression of a selected nucleic acid sequence, operationally bound to the promoter), and that affects the expression of a selected nucleic acid sequence in specific tissue cells, such as neurons. The specific binding site for the regulatory element of neural tissue transcription may be constituent or inducible.

The term 'CAP gene' or 'AAV CAP gene', as used in the present invention, refers to a gene that encodes for a CAP protein. The term 'CAP protein', as used herein, refers to a polypeptide that has activity of at least one functional activity of the CAP protein of a native AAV (VP1, VP2, VP3). Examples of functional activities of the VP1, VP2, and VP3 proteins include the ability to induce capsid formation, facilitate simple strand DNA accumulation, facilitate the packaging of AAV DNA into the capsid (i.e., encapsulation), bind to cell receptors, and facilitate the entry of the virus into a host.

The term 'capsid', as used in the present invention, refers to the structure in which the viral genome is packaged. A capsid consists of an oligomeric structure with structural subunits of CAP proteins. For example, AAV has an icosahedral capsid formed by the interaction of three capsid proteins: VP1, VP2 and VP3.

The term 'cell composition', as used in this document, refers to a composite type material comprising the cells of the invention and at least one other component. The composition may be formulated as a single formulation or may be presented as separate formulations of each of the components, which may be combined for joint use as a combined preparation. The composition can be a parts kit, where each of the components is individually formulated and packaged.

The term 'constituent promoter', as used in the present invention, refers to a promoter whose activity is maintained at a relatively constant level throughout an organism, or during most experimental stages, with little or no consideration for the cell's environmental and external conditions.

The term 'expression cassette', as used here, refers to a construction of nucleic acids, generated synthetically or by recombination, with a series of elements specific to nucleic acids, which allow the transcription of a particular nucleic acid into a target cell.

The term 'genes that provide support functions', as used herein, refers to genes that encode polypeptides, performing functions on the AAV that are dependent for replication (i.e. "support functions"). Auxiliary functions include functions that are necessary for AAV replication, including these fragments involved in the activation of AAV gene transcription, the specific stages of AAV mRNA splicing, AAV DNA replication, synthesis of CAP products, and AAV capsid assembly. Accessory viral functions can be derived from any of the known auxiliary viruses such as adenoviruses, herpes viruses, lentivirus and the vaccinia virus. Auxiliary functions include, but are not limited to, the WHV lentivirus.

The term 'operationally linked', as described in this document, refers to the functional relationship and location of a promoter sequence with respect to a polynucleotide of interest (e.g., a promoter or enhancer is operationally linked to a coding sequence which affects the transcription of that sequence). Generally, an operationally linked developer is adjacent to the sequence of interest.

However, an enhancer does not have to be adjacent to the sequence of interest to control its expression.

The term 'locally administered', as used herein, means that the polynucleotides, vectors, polypeptides, and/or pharmaceutical compositions of the invention are administered to the subject at or near a specific site.

The terms 'pharmaceutically acceptable carriers', 'pharmaceutically acceptable diluents', 'pharmaceutically acceptable excipient' or 'pharmaceutically acceptable vehicle' are interchangeable in this document, referring to a non-toxic solid, semi-solid, or filling liquid, diluent or encapsulation material or an auxiliary formulation for any conventional type. A pharmaceutically acceptable carrier is essentially non-toxic to the containers used in the dosages and concentrations and is compatible with other ingredients in the formulation. The number and nature of pharmaceutically acceptable vehicles depends on the desired administration method. Pharmaceutically acceptable vehicles are known and can be prepared by well-known technical methods.

The term 'promoter', as used herein, refers to a nucleic acid that controls the transcription of one or more polynucleotides, located upstream of the sequence of the polynucleotide(s), and which is structurally identified by the presence of a RNA polymerase dependent DNA binding site, the transcription initiation sites, and any other DNA sequence, including, but not limited to, transcription factor binding sites, repressor, and activator protein binding sites, and any other nucleotide sequences known to the technique to act directly or indirectly to regulate the amount of transcription from the promoter. A 'tissue-specific' promoter is activated only in certain types of differentiated cells or tissues.

The term 'polynucleotide', as used herein, refers to a nucleic acid molecule, either DNA or RNA, containing deoxyribonucleotides or ribonucleotides, respectively. Nucleic acid may be a double strand, single strand, or contain parts of either a double strand or single strand sequence. The term 'polynucleotide' includes, but is not limited to, nucleic acid sequences with the ability to encode a polypeptide and nucleic acid sequences which are partially or wholly complementary to an endogenous polynucleotide of the cell or subject treated with it in a manner that, after transcription, generates an RNA molecule (e.g. microRNA, shRNA, siRNA) capable of hybridizing and inhibiting the endogenous polynucleotide expression.

The term 'bridge or linker', as used herein, refers to a continuous or discontinuous polynucleotide sequence, either DNA or RNA, which allows for the physical separation of objective sequences, positioning them in a suitable manner so that they can be translated and transcribed.

The term 'string' in this document refers to a sequence of continuous nucleotides (including or not modified natural or non-natural nucleotides). The two or more strands may be, or each may be a part of, separate molecules, or they may be covalently interconnected, for example, by means of a coupling (for example, a linker such as polyethylene glycol), to form a molecule. At least one of the strands may include a region that is sufficiently complementary to a target RNA.

A second chain of the dsRNA agent, comprising a complementary region to the antisense chain, is called the "sense strand". However, a siRNA agent can also be formed from a single RNA molecule that is at least partially self-complementary, forming, for example, a hairpin or buttonhole structure, which includes a duplex region. The latter are hereinafter referred to as short hairpin RNAs or shRNAs. In such a case, the term 'strand' refers to one of the RNA molecule's region that is complementary to another region of the same RNA molecule.

The term 'recombinant viral genome', as used herein, refers to an AAV genome in which at least one non-expressive polynucleotide cassette is inserted into the native AAV genome.

The term 'rep gene' or 'AAV rep gene', as used herein, refers to a gene that encodes a Rep protein. The term "Rep protein", as used herein, refers to a polypeptide that has at least one functional activity of a native AAV rep protein (e.g., Rep 40, 52, 68, 78). A "functional activity" of a Rep protein (e.g. Rep 40, 52, 68, 78) is any activity associated with the physiological function of the protein, including the facilitation of DNA replication through the recognition, binding and cutting off of the origin of AAV DNA replication, as well as the helical activity of DNA Additional functions include modulation of AAV transcription (or other heterologous) promoters and site-specific integration of AAV DNA into a host chromosome.

The term 'subject', as used herein, refers to an individual, plant, mammal or animal, such as a human, a non-human primate (e.g., chimpanzee or other ape and other monkey species), an animal (e.g., birds, fish, livestock, sheep, pigs, goats and horses), a mammal (e.g., dogs and cats), or a laboratory animal (e.g., rodents, such as mice, rats, mice with silenced genes (knockout mice), mice that overexpress a gene (transgenic mice, and guinea pigs). The term does not indicate a particular age or sex. The term 'subject' includes an embryo and a fetus.

The term 'systemically administered' and 'systemically administered', as used herein, means that the present invention's polynucleotides, vectors, polypeptides, or pharmaceutical compositions are administered to a subject in a non-localized form. The systemic administration of the polynucleotides, vectors, polypeptides, or pharmaceutical compositions of the invention may reach several organs or tissues in the subject's entire body, or may reach new specific organs or tissues. For example, the intravenous administration of a pharmaceutical composition of the invention may result in transduction in more than one tissue or organ in a subject.

The term 'transcriptional regulatory element', as used herein, refers to a nucleic acid fragment capable of regulating the expression of one or more genes. The polynucleotide regulatory elements of the invention include a promoter and, optionally, an enhancer.

The term 'transduction', as used herein, refers to the process by which a sequence of foreign nucleotides is introduced into a cell into a viral vector.

The term 'transfection', as used in this document, refers to the introduction of DNA into the target eukaryotic cells.

The term 'vector', as used herein, refers to a construct capable of delivering, and optionally expressing, one or more polynucleotides of interest in a host cell. Examples of vectors include, but are not limited to, viral vectors, DNA or bare RNA expression vectors, plasmid, cosmic or phage vectors, RNA or DNA expression vectors associated with cationic condensing agents, liposomal encapsulated DNA or RNA expression vectors, and certain eukaryotic cells, such as producing cells. Vectors can be stable and can be self-replicating. There are no limitations as to the type of vector that can be used. The vector may be a cloning vector, suitable for propagation and for obtaining polynucleotides, gene constructs or expression vectors incorporated into several heterologous organisms. Suitable vectors include prokaryotic expression vectors, phage and shuttle vectors and eukaryotic expression vectors based on viral vectors (e.g. adenovirus, adeno-associated viruses as well as retrovirus and lentivirus), as well as non-viral vectors such as pSilencer 4, 1-CMV.

The term 'UPRplus', as used in this document, refers to sequences consisting of XBP1s, ATF6f, a promoter, a connection or bridge sequence and an epitope for identification.

The invention's methods and compositions (for example the methods and compositions of the AAV virus with the aforementioned inserts) may be used with any dosage and/or formulation described in the present invention, as well as with any route of administration described in the present invention.

For the term 'cognitive and motor treatment or therapy skills', we refer to cognitive and motor tests performed on different species and/or subjects with a pathology as defined in the present invention.

The term 'cDNA' or 'complementary DNA' refers to a DNA sequence that perfectly complements a RNA sequence, used to form an RT-PCR synthesis.

The phrase 'silencing of a target gene' refers to the process whereby a cell that contains and/or expresses a particular product of the target gene when not in contact with the agent, will contain and/or express at least 10%, 20%, 30%, 40%, 50%, 60%, 70%, 80%, 90% or less of such gene's product when in contact with the agent, compared to a similar cell that has not been contacted with the agent. This target gene product may, for example, be a messenger RNA (mRNA), a protein, or a regulatory element.

The term 'complementary' as used in this document indicates a sufficient degree of complementarity such that a stable and specific binding takes place between a compound and a target RNA molecule. Specific binding requires a sufficient degree of complementarity to avoid non-specific binding of the oligomeric compound to non-target sequences, under conditions where specific binding is desired, i.e. under physiological conditions in the case of in vivo tests or therapeutic treatment, or in the case of in vitro tests, under conditions where tests have been performed.

The term 'restriction sites' as used in this document refers to the nucleotide sequence to which a specific restriction enzyme for said sequence is attached and cuts or splits off.

Ligands

The properties of a virus, including its pharmacological properties, can be influenced and tailored, for example, by the introduction of ligands. In addition, the pharmacological properties of a viral agent can be improved by the incorporation of a ligand into an agent formulation and a virus.

Ligands can be attached to a wide variety of entities, such as ligands that bind to a viral agent, or can be used as a conjugate or formulation additive; for example, with the vehicle of a monomeric subunit attached to the ligand. The examples are described below in the context of a monomeric subunit attached to a ligand, but that is only the preferred one, and entities can be coupled elsewhere with a virus.

A ligand alters the distribution, direction, or lifetime of the viral agent into which it is embedded. In the preferred modalities, a ligand provides a better affinity for a selected target; for example, a molecule, cell, or cell type, a compartment (such as a cell or organ compartment, a tissue, or region of the body), as compared to a species in which said ligand is absent.

In the present invention, ligands may improve the transport, hybridization, and specificity properties of the target molecule in the virus.

Ligands in general may include therapeutic modifiers, for example to improve absorption of the molecule in the individual; diagnostic compounds or reporter groups, for example, to monitor distribution; crosslinking agents; fractions that confer resistance to immune reactions; and natural or unusual nucleobases.

General examples include lipophilic molecules, lipids, lectins, (e.g. hecigenin, diosgenin), terpenes (e.g. triterpenes, sarsasapogenin, friedelin, lithocholic acid derived from epifriedelanol), vitamins, carbohydrates (e.g. a dextran, pululan, chitin, chitosan), synthetic (e.g., 15-mer oligolactate) and natural (e.g., low and medium molecular weight) polymers, inulin, cyclodextrin, or hyaluronic acid), proteins, protein binding agents, integrin binding molecules, polycations, peptides, polyamines, and peptide mimetics. Other examples include epithelial cell or folic acid receptor ligands, such as transferrin.

The ligand can be a naturally occurring or recombinant or synthetic molecule, such as a synthetic polymer (for example, a synthetic poly-amino acid). Examples of polyamino acids include polylysine (PLL), poly-aspartic acid L-aspartic, poly-acid L-glutamic, styrene-anhydride copolymer of maleic acid, poly-(lactic-co-glycolic) copolymer of divinyl ether-maleic anhydride, copolymer of N-(2-hydroxy propyl)-methacrylamide (HMPA), polyethylene glycol (PEG), polyvinyl vinyl alcohol (PVA), polyurethane, poly (2-ethylacrylic acid), N-isopropyl-acrylamide polymers, or polyphosphazene. Examples of polyamines include: polyethyleneimine, polylysine (PLL), spermine, spermidine, polyamine, pseudo-peptide polyamine, peptidomimetic polyamine, dendrimer polyamine, arginine, amidine, protamine, cationic fractions, e.g. cationic lipid, cationic porphyrin, quaternary salt of a polyamine, or an alpha-helical peptide.

Ligands may also include steering groups, for example a steering agent to a cell or tissue, such as a thyrotropin, melanotropin, surfactant protein A, mucin carbohydrate, a glycosylated polyaminoacid, bisphosphonate, polyglutamate, polyaspartate, an Arg-Gly-Asp peptide (RGD), or a mimetic of RGD peptide.

Ligands can be proteins, for example glycoproteins or lipoproteins such as low-density lipoprotein (LDL), or albumin, such as serum albumin, or peptides, such as molecules that have a specific affinity for a co-ligand, or antibodies, such as an antibody that binds to a specific cell type. Ligands may also include hormones and hormone receptors. They may also include non-peptide species, such as cofactors, multivalent lactose, multivalent galactose, N-acetyl-galactosamine, N-acetyl-glucosamine, multivalent mannose, or multivalent fucose.

The ligand can be a substance, such as a drug, that can increase the absorption of the viral agent within the cell; for example, by altering the cell's cytoskeleton, or its microtubules, microfilaments, and/or intermediate filaments.

In one respect, a ligand is a lipid, or a lipid-based molecule. This lipid or lipid-based molecule is preferably bound to a whey protein, such as albumin serum.

Alternatively, viruses may be packaged.

The preparation of injectable virus solutions is performed by diluting the necessary virus concentration in PBS (saline phosphate buffer), which is formulated as follows.

1. Dissolve the viral dose (previously diluted in PBS 1×) in 800 ml of distilled water with:

8 g of NaCl 0.2 g of KCl 1.44 g of $Na2HPQ^4$ 0.24 g of $KH2PO^4$

2. Adjust pH to 7.4 with HCl.

3. Set the volume to 1 L with additional distilled water H2O.

4. Sterilize and autoclave.

Design and Selection

Generation of UPRplus Molecule Variants.

One of the objectives of this patent is to generate the six variants of a recombinant DNA, composed of the human sequences of the active form of XBP1, called XBP1s and the active form of ATF6, called ATF6f. The UPRplus variants include two variables in their design: the order of the XBP1s and ATF6f molecules (XBP1s-ATF6f and ATF6f-XBP1 s) and the binding peptide (also known as linker) between the two sequences. The linkers used are as follows:

19-AA Glycine Flexible Linker ("GFL");

25-AA Alpha Helix Linker ("AHL4"); and

50-AA Flexible Linker ("FL").

It has been shown that these three types of joints or bridges provide the flexibility and adequate distance between the proteins joined at their ends, in order to achieve an interaction between them. The generation and evaluation of these three linkers between the XBP1s and ATF6f molecules allowed to extend the possibilities of generating an active functional transcription factor, which adopts an adequate three-dimensional geometry to join the specific gene elements.

In addition, to better detect the expression of these chimeric proteins, the hemagglutinin peptide (HA) protein sequence (among others, not limited to this epitope) was added to the terminal carboxylic endpoint of all proteins.

The utilized cloning strategy generated the DNA sequences of XBP1s, ATF6f and the three different linkers by de nova synthesis, including restriction sites for subsequent linking to the pAAV expression vector. This expression vector was used to generate viral particles prior to the selection of the UPRplus variant with the highest in vitro neuroprotective activity.

By means of de nova synthesis two sets of gene sequences were obtained. These included the HA sequence at the 3rd end, and depending on the linker, the various restriction sites shown below:

Set 1 XBP1s-Linker-ATF6f
SnaBl_XBP1 s-LFG-ATF6f_Fsel
BspEl_XBPS1 s-LF-ATF6f_Kpnl
BspEl_XBPs-L4H4-Atf6f_Kpnl
Set 2 ATF6-Linker-XBP1s
SnaBl_ATF6-LFG-XBP1s_Fsel
Kpnl_ATF6-L4H4-XBP1s_Sfil
Kpnl_ATF6-LF-XBP1s_Sfil The mRNA sequences used for this purpose are described in tables VII and VIII, ATF6f and XBP1s, respectively.

The mRNA sequences of the linkers or jumpers are described in Table IX, which shows the LGF, L4H4 and LF linkers.

Along with the generation of these 6 UPRplus variants, the individual versions of XBP1s and ATF6f associated with AAV (tables XI and XII, respectively) were produced, cloned in the pAAV expression vector to correctly compare UPRplus's activity with respect to the individual expression of these transcription factors.

The expression of these sequences uses the same promoter of the UPRplus variants and presents the HA peptide, unlike previous studies performed with the transcription factor XBP1 s and ATF6f, which did not contain these elements.

Once these sequences were obtained by de nova synthesis, they were then linked to the pAAV expression vector through the aforementioned restriction sites. The 8 versions of the generated recombinant DNA were sequenced, confirming that the sequences were correct and consistent with the expected results.

The de novo synthesis of the aforementioned sequences and the linking of these sequences to the pAAV vector were performed by the GENEWIZ company in the United States.

The sequences obtained in the plasmids can be seen as maps in FIGS. 1-6.

To confirm these plasmids, a restriction analysis of the obtained sequences was performed by means of plasmid DNA digestion using the EcoR1 restriction enzyme.

The fragment sizes obtained in the restriction enzyme assays were as expected, as shown in FIG. 7.

An analysis of the biomedical scope for its therapeutic use provided an effective and innovative method to treat neurodegenerative diseases, in which the use of this technology produced surprising results in its application.

To explore the involvement of UPRplus, the six recombinant DNA variants described in the previous paragraphs were generated. They encode human sequences of the active form of XBP1, called XBP1s, and the active form of ATF6, called ATF6f, linked by different linkers and linked to an epitope for hemagglutinin (HA), among other possible epitopes.

With respect to the development of the adeno-associated virus (AAV), it comprises the viral recombinant genome that includes an expression cassette with a transcriptional regulatory element operationally linked to the polynucleotide of interest. The AAV serotype type provides part of the tissue selectivity in which the polynucleotide of interest will be expressed, without being exclusive.

According to the present invention, the adeno-associated virus (AAV) includes any known serotype of the 42 types and is derived from parvoviruses. In general, the various AAV serotypes are significantly homologous genomic sequences in terms of amino acids and nucleic acids, which provide identical genetic functions, provide vibrio bacteria that are essentially identical in functional and physical terms, and their replication and assembly use virtually the same mechanisms.

In the present invention in particular, AAV serotype 2 was used (such as those mentioned in GenBank access number ((AAV2) NC_001401.2, (AAV6) AF028704.1, NC006260 (AAV7), NC006261 (AAV8), AX753250.1 (AAV9), (AAV10), (AAV11) and pseudotyped AAVs, as presented for AAV2, in Table X.

For AAV10 and AAV11 viruses, a complete sequence is not available as they differ in capsid proteins.

According to the present invention, the AAV genome normally comprises an actuator in cis 5 and an inverted 3 terminal repeating sequence and an expression cassette. ITR or LTR sequences have a length of 141 base pairs. Preferably, the complete sequence of the LTRs is used in the molecule and only slight modifications of the sequences are allowed. In a preferred form of the present invention, the recombinant genome of the AAV comprises the 5th and 3rd AAV LTRs. In another preferred form of the present invention the 5th and 3rd AAV LTRs are derived from AAV serotype 2. In another more preferable form of the present invention, the recombinant genome of AAVs lacks the Rep and Cap open reading frame.

On the other hand, ITRs can come from other AAV serotypes.

The present invention's AAV comprises a capsid from any serotype. In particular, for the present invention, capsids derived from serotypes 2, 6, 7, 8, 9 and 10 are preferred. However, the AAV capsid of serotype 2 is preferred.

In some implementations, an AAV cap for use in the method of invention may be generated by mutagenesis (i.e., insertions, deletions or substitutions) of one of the AAV caps or their coding nucleic acids. In some productions, the AAV cap is at least 70%, 75%, 80%, 85%, 90%, 95%, 98%, or 99% or more similar to one or more of the aforementioned AAV caps.

In some implementations, the AAV cap is chimeric, comprising the domains of two, three, four, or more of the aforementioned AAV caps. In some designs, the AAV cap is a mosaic of the monomers VP1, VP2, VP3 and coming from two or three different AAVs or a recombinant AAV (rAAV). In some productions, a composition of rAAV comprises more than one of the above CAPS.

In some implementations, an AAV CAP for use in an rAAV composition is designed to contain a heterologous sequence or other modification. For example, a peptide or protein sequence that confers selective targeting or immune evasion may be genetically engineered on a Cap protein. Alternatively, or in addition, the Cap may be chemically modified so that the surface of the rAAV presents specific chemical modifications, such as polyethylene glycolates, which may facilitate immune evasion. The Cap protein can also be generated by guided mutations (e.g. to remove its natural binding receptor, or to mask an immunogenic epitope).

In one implementation, the AAV vector contains a promoter with the addition of at least one target sequence of at least one sequence of SnaBl_XBP1s-LFG-ATFG-ATF6f_Fsel; or BspEl_XBPS1s-LF-ATF6f_Kpnl; or BspEl_XBPs-L4H4-Atf6f_Kpnl; or SnaBl_ATF6-LFG-XBP1s_Fsel; or Kpnl_ATF6-L4H4-XBP1s_Sfil or Kpnl_ATF6-LF-XBP1s_Sfil that can be selected from the following tables: Table I (SnaBl_XBP1s-LFG-ATFG-ATF6f_Fsel) or Table II (BspEl_XBPS1s-LF-ATF6f_Kpnl) or Table III (BspEl_XBPs-L4H4-Atf6f_Kpnl) or Table IV (SnaBl_ATF6-LFG-XBP1s_Fsel) or Table V (Kpnl_ATF6-L4H4-XBP1s_Sfil) or Table VI (Kpnl_ATF6-LF-XBP1s_Sfil), obtained from GenBank.

In one implementation, the AAV vector contains a promoter with the addition of at least one of the target sequences of SnaBl_XBP1 s-LFG-ATF6f_Fsel; or BspEl_XBPS1s-LF-ATF6f_Kpnl; or BspEl_XBPs-L4H4-Atf6f_Kpnl; or SnaBI.

In one implementation, the AAV vector contains a promoter with the addition of at least one target sequence that is 85% homologous with a target sequence selected from the aforementioned tables.

In one implementation, the AAV vector contains a promoter with the addition of at least one target sequence that is 70% homologous with a target sequence selected from the aforementioned tables.

In one implementation, the AAV vector contains a promoter with the addition of at least one target sequence, which is a functional equivalent of a target sequence selected from the aforementioned tables.

The transcription regulatory element may comprise a promoter and, optionally, an enhancer region. The promoter is preferably selected from this list: CMV, PGK1, CAMKll, THY1, GAD34 among others. The enhancer need not be specific to the neural tissue.

In one implementation, the promoter is specific, for example, to the cytomegalovirus, also known as CMV.

In an implementation, the promoter is specific, for example, to the phosphoglycerate kinase 1 protein, also known as PGK1.

In one implementation, the promoter is specific, e.g. Calcium Calmodulin Kinase 2, also known as CAMKll.

In one implementation, the promoter is specific, e.g. also known as Thy1.

In one implementation, the promoter is specific, for example, the one for glutamic acid decarboxylase 34, also known as GAD34, which normally operates in GABAergic neurons.

In another implementation, the expression cassette that forms part of the present invention's AAV also comprises a post-transcriptional regulatory element. In a preferred implementation, the post-transcriptional regulatory element is the Woodchuck Hepatitis Virus post-transcriptional regulatory element (WPRE) or functional variants and fragments thereof and the PPT-CTS or functional variants and fragments themselves. In one particular implementation, the post-transcriptional regulatory element is WPRE.

The expression cassette forming part of the AAV in accordance with the invention comprises a 'polynucleotide of interest'. In a preferred realization, the polynucleotide of interest encodes a systemically acting protein. In another implementation, the polynucleotide of interest encodes a protein that acts within a neuron. In a preferred implementation, the protein that acts within that neuron is: XBP1s-LFG-ATF6f; or XBP1s-LF-ATF6f; or XBP1s-LF-ATF6f; or XBP1s-L4H4-ATF6f; or ATF6f-LFG-XBP1s; or ATF6-L4H4-XBP1s or ATF6f-LF-XBP1s, including any of their isoenzymes that vary in subcellular locations.

The size limit of the AAV vector packaging is limited to the size of the wild-type AAV genome, which varies in size according to the AAV stereotype (namely, between 4087 and 4767). For example, native AAV-2 has a genome size of 5382. In some forms of realization, the cloning capacity of the recombinant RNA vector may be limited, and a desired coding sequence may involve the complete replacement of 4.8 kilobases of the virus genome. Large-sized genes may therefore not be suitable for use in a standard recombinant AAV vector in some cases. The average expert will discern that the options are available in the technique for overcoming a limited coding capacity. For example, the two-genome AAV IRT can hybridize to form the head to tail concatemers, almost doubling the vector's capacity. The insertion of the splice sites allows removal of the IRT after transcription. Other options for overcoming a limited cloning capacity will be evident to the expert in the subject matter.

As a next objective, the expression of these variants was tested on a human cell line. In order to carry out this objective, the SHSY5Y neuroblastoma-derived cells were replaced with HEK293 cells, due to the low transfection percentage (30%) of SHSY5Y cells. The HEK293 cells correspond to a human kidney embryonic cell line, which presents a high percentage of transfection (80%) by the $CaPQ^4$ method.

The HEK293 cells were transfected with the 6 variants of UPRplus. As a control, the individual versions of human XBP1s and ATF6f (Tables XI and XII, respectively) that were cloned in the same expression vector were included. Also included was the expression of two versions corresponding to the mouse DNA sequence of XBP1s existing in the laboratory.

The HEK293 cells were transfected using the $CaPQ^4$ method with the respective recombinant DNAs and after 48 hours of expression the protein extraction with RIPA buffer and quantification of total proteins was performed.

Subsequently, different proteins were detected by means of Western Blot (WB), using the antibodies anti-HA, anti-XBP1 and anti-ATF6.

The WB analysis showed that these proteins were expressed correctly, as it was possible to detect all variants of UPRplus with the anti-HA antibody as shown in FIG. 8. The epitope for hemagglutinin (HA) is present at the terminal C-end of all UPRplus variants and was therefore used as a first approximation. The molecular weights obtained were approximately ~100 kDa for the UPRplus variants and ~50 kDa for the individual proteins.

The molecular size obtained for the individual version of cloned XBP1s in the viral expression of the UPRplus variants does not differ compared to the mouse XBP1 s versions already characterized and determined in the same assay (FIG. 8, lanes 8 and 11). The molecular weights obtained according to the electrophoretic migration were higher than the expected molecular weights (see FIG. 8), both for the UPRplus proteins and the individual proteins.

On the other hand, the expression of human XBP1s was detected in all UPRplus variants (lanes 1-6, FIG. 9) as well as in the individual variant (lanes 8, FIG. 9) using the anti-XBP1 143F (Biolegend) antibody. Since this antibody only recognizes the human form of XBP1s, it was not possible to detect the expression of the mouse XBP1s sequence (lanes 9, 11 and 12, FIG. 9).

Finally, the ATF6f protein present in the UPRplus variants was also detected with an anti-ATF6 (abCam) antibody as shown in FIG. 10. This antibody recognized both the human and mouse versions of ATF6f (FIG. 10).

In order to determine the subcellular location of these proteins in HEK293 cells, indirect immunofluorescence assays were conducted on cells expressing UPRplus proteins and their individual versions. The same antibodies described above, used in the WB analysis, were used. The expression of the epitope HA, of the XBP1 and ATF6 proteins was detected (FIGS. 11-13) in HEK293 cells transiently transfected with the different variants of UPRplus and also in the cells transfected with the individual versions of the XBP1s and ATF6 proteins. From these results, we determined that the subcellular location of the 6 UPRplus variants corresponds to a nuclear pattern that became evident upon co-marking with the Hoechst probe, which specifically stains the nuclei of cells (FIGS. 11-13). In order to determine the specificity of the anti-HA antibody, cells that were transiently transfected with the mXBP1s/EGFP plasmid corresponding to the mouse sequence of XBP1s were included as a negative control (FIG. 11B).

It was also determined that the anti-XBP1 antibody specifically recognizes the XBP1 protein by immunofluorescence in all variants of UPRplus. The specificity of the anti-XBP1 antibody was determined by the absence of the mark on cells transfected with ATF6 individually or in non-transfected cells. (FIG. 12A). With this assay, it was possible to detect the mouse sequence of XBP1s using the anti-XBP1 antibody (FIG. 12B).

The expression of ATF6 was also corroborated by immunofluorescence in HEK293 cells transfected with UPRplus variants. Detection of the ATF6 protein was observed in all protein variants of UPRplus, except in cells that were transfected with XBP1s individually which was used as a negative control (FIG. 13).

Subsequent to the subcellular localization of the expression of these proteins in transfected HEK293 cells, the activation of the promoter element was evaluated in response to the unfolded protein response, "UPR", mediated by the pAAV-UPRplus virus, using reporters coupled to Luciferase activity.

This analysis of the transcriptional activity of the pAAV-UPRplus variants was conducted using the Luciferase reporter system under the control of the UPR element, called "UPRE", which preferably responds to the heterodimer between ATF6f and XBP1s. For this purpose, HEK293 cells were co-transfected with the plasmids pAAV-UPRplus 1 to 6 in conjunction with the Luciferase-UPRE reporter plasmid. In addition, a Renilla encoding plasmid was transfected, which was used as an internal control for the assay to determine the percentage of cells expressing all plasmids, as it constitutively expresses a chemiluminescent molecule (Promega, Dual-Luciferase® Reporter Assay System). After 48 hours of expression, the luminescence obtained was measured in a luminometer. The activation levels of the response element to UPR by the pAAV-UPRplus variants were compared with those generated by the transfection of the encoding plasmid for the activated form of the XBP1s, called pAAV-XBP1 s, and the active form of ATF6, called pAAV-ATF6f, and the co-transfection of both plasmids (pAAV-XBP1s y pAAV-ATF6f). Also included as a positive control of the experiment was the transfection of the pCDNA3-mXBP1s plasmid corresponding to the version of the mouse sequence of XBP1s. The pCDNA3 empty vector transfection was also included as a baseline activity of the XBP1/ATF6 transcriptional activity system of XBP1/ATF6 transcription factors.

FIG. 14 shows the transcriptional activity of the 6 variants of UPRplus and of the relevant controls. The values shown represent the average of three independent experiments. As shown in Table XIII:

TABLE XIII

| Plasmid | Experiment 1 | Experiment 2 | Experiment 3 | Average | ESM |
| --- | --- | --- | --- | --- | --- |
| PAAv_ATF6f-LFG-XBP1s-HA | 101,1517 | 99,62383 | 125,4241 | 108,73321 | 8,357091867 |
| PAAv_ATF6f-LF-XBP1s-HA | 88,52831 | 119,747 | 191,8758 | 133,3837033 | 30,60308089 |
| PAAv_ATF6f-L4H4-XBP1s-HA | 79,35313 | 77,71852 | 71,44357 | 76,17174 | 2,410717813 |
| PAAv_XBP1s-LFG-ATF6f-HA | 17,81713 | 12,53527 | 21,4335 | 17,26196667 | 2,583652391 |
| PAAv_XBP1s-LF-ATF6f-HA | 15,62922 | 11,8496 | 23,48904 | 16,98928667 | 3,428142203 |
| PAAv_XBP1s-L4H4-ATF6f-HA | 9,228968 | 11,24907 | 10,3266 | 10,26821267 | 0,583883502 |
| PAAv_ATF6f-HA | 120,188 | 122,1534 | 139,6209 | 127,3207667 | 6,17618165 |
| PAAv_XBP1s-HA | 47,8104 | 47,95798 | 46,66553 | 47,47797 | 0,408447887 |
| PAAv_ATF6f-HA + PAAv_XBP1s-HA | 100 | 100 | 100 | 100 | 0 |
| pCDNA3_mXBP1 | 77,29633 | 120,5979 | 116,0251 | 104,6397767 | 13,73530344 |
| pCDNA3 | 4,874095 | 6,953351 | 4,208801 | 5,345415667 | 0,826588582 |

The maximum activity (100% of transcriptional activity) was determined as the activation values reached by the co-transfected XBP1 s and ATF6f variants, and based on this value the activities of each of the variants in each experiment were normalized.

The results obtained show a transcriptional activity of the 1-3 variants similar to the co-expression condition of XBP1 s and ATF6f. These variants are capable of binding to the UPRE promoter region and achieve activating the expression of the Luciferase reporter. The 4-6 variants presented levels of transcriptional activity of around 20% with respect to the ATF6f/XBP1s co-expression control, so it is likely that they will not be able to bind to the UPRE promoter region or that the structure of adopting this chimeric protein will alter its binding to the DNA sequence.

In addition, it was determined that the individual variants are capable of activating the UPRE promoter region and that ATF6f presents a greater activity than the XBP1s protein.

These results verify that three of the mixed variants of "ATF6f-XBP1 s", those assigned as 1, 2 and 3, maintain the activating property of the UPR, indicating that the strategy proposed in the project is viable and is possibly capable of activating target genes related to the transcriptional activity of the heterodimer ATF6f/XBP1s.

The next step in this development was to evaluate the activation of the UPR transcriptional targets mediated by the expression of pAAV-UPRplus.

HEK293 cells were used to conduct this study, which were transfected with the coding plasmids for the six pAAV-UPRplus variants and the individual pAAV-XBP1s and pAAV-ATF6f variants. In addition, the co-transfection of both variants (pAAV-XBP1s and pAAV-ATF6f) was included, a condition that was considered as the maximum activation reached by the heterodimer in these experimental tests.

After 24 hours of expression, the transcriptional activation of genes associated to the UPR pathway was measured by quantifying the mRNA levels of a group of genes described as transcriptional targets modulated by the heterodimer ATF6f-XBP1 s using the real-time PCR technique.

The genes analyzed during this project stage were described in a recent study (Shoulders et al., 2013), which determined, by mass sequencing, the genes differentially regulated by XBP1s and/or ATF6 in HEK293 cells. In this study, HEK293 cells were generated that are capable of expressing the XBP1s and/or ATF6f transcription factors in a differential and induced way by the addition of drugs that control the expression of these proteins. This system is capable of expressing XBP1s by adding doxycycline, ATF6f by the drug trimethoprim (TMP), and both proteins (heterodimer) through the incubation with both drugs.

The genes described that are expressed differentially by these transcription factors are shown in the following Table XIV:

TABLE XIV

| XBP1 | ATF6 | XBP1/ATF6 |
|---|---|---|
| Erdj4 | HspA5 (BiP) | Creld2 |
| Sec24D | HerpUD | Edem1 |
| Stt3a | Pdia4 | Hyou1 |
|  | Sel1L | Sulf1 |

Table XIV above presents the genes regulated by XBP1 and/or ATF6 in inducible HEK293 cells.

Based on this information, oligonucleotide sequences were generated to determine the expression levels of the genes shown in Table XIV using real-time PCR in HEK cells treated with the drug tunicamycin, which induces endoplasmic reticulum stress (ER).

With this assay we were able to test the amplification efficiency of these genes and corroborate that these genes are activated in response to the ER stress condition.

As shown in FIG. 15, it was determined that the genes were efficiently amplified, and it was also confirmed that they increase their expression in response to the ER stress condition.

Subsequently, the mRNA levels of some of the transcriptional UPR targets were compared, obtained from HEK293 cells transfected with each of the six variants of pAAV-UPRplus, pAAV-XBP1s or pAAV-ATF6f individually, and co-transfected with both variants (pAAV-XBP1s and pAAV-ATF6f).

The genes that were chosen for analysis were those associated with the activation of the heterodimer. The chosen genes were: CRELD2, a gene associated with the degradation of unfolded proteins associated with the ER process called ERAD ("Endoplasmic Reticulum Associated protein Degradation"), HYOU1, related to the protein folding process, and EDEM 1, associated with ERAD and SULF1, a secreted enzyme involved in the formation of the extracellular matrix. In addition, the activation of BIP, associated with the protein folding and HERPUD involved in the ERAD process, was determined. For the messenger RNAs associated with the expression of the heterodimer such as Creld2, Edem 1, Hyou1 and Sulf1, it is observed that variants 1, 2 and 3 are capable of activating this group of genes in comparison to the 4, 5 and 6 variants (FIG. 16). Additionally, in the case of the expression of the SULF1 gene, the UPRplus3 variant presents a greater activation than that obtained when the XBP1s and ATF6f variants are co-expressed.

This result shows us that UPRplus chimeric proteins are capable of activating genes associated with the unfolded protein response. In addition, the activation levels reached by the 1, 2 and 3 variants are similar or greater than those obtained by co-expressing both proteins (FIG. 16). With respect to the chaperone Bip and the HERPUD genes associated with ERAD, we also observed that the 1, 2 and 3 variants of UPRplus are capable of preferentially activating these genes, reaching induction levels similar to those obtained when co-expressing these transcription factors. The results obtained correspond to the average of three independent experiments.

Routes of Administration

The routes of administration of the virus are subject to its passing through the blood-brain barrier to infect the target neurons.

To achieve this objective in the present invention, 2 routes of administration have been mainly defined.

The first of these routes is the nasal route. Generally, drugs administered nasally can enter the bloodstream through general circulation, can penetrate the brain directly, or in some cases can follow both routes. However, many of the factors that control the flow of the drug through each of these routes are not fully defined. In general, there are three routes by which a drug administered in the nasal cavity can travel. These routes include entry into the systemic circulation directly from the nasal mucosa, entry into the olfactory bulb by axonal transport through the neurons, and direct entry into the brain. Evidence supporting the role of each of these routes for a variety of model substrates is summarized below for the different types of viruses.

| Transport routes followed by several viral solutes through nasal administration | | | |
|---|---|---|---|
| Solute | Animal model | Route of Administration | Route traveled |
| Virus | | | |
| Hepatitis Virus | Mouse | Nasal Inoculation | Olfactory nerve |
| Herpes Simplex Virus | Mouse | Nasal drops | Direct, Systemic, Olfactory, Nerve |
| Encephalitis Virus | Mouse | Nasal Inoculation | Olfactory Nerve |
| Pneumococcus | Mouse | Nasal drops | Direct |

This table is not intended to be exhaustive in nature, but rather to highlight some of the different kinds of solutes that have been shown to follow one or more routes.

Other routes of administration to the cells in the CNS have included:

Direct injection into fluid compartments, such as the vitreous humor in the eye; or into the cerebral fluid of the spine through different routes, intraventricular or intrathecal (**), for delivery to the choroid plexus, the ependymal/meningeal layers, and from there in the adjacent brain through processes that extend within these layers; and its passage through the blood-brain barrier or blood-tumor barriers by intra-arterial injection combined with a temporary osmotic or pharmacological interruption.

The term (**) Intrathecal (intra+theca, "within a sheath") is an adjective that refers to something that occurs or is introduced into an anatomical space or potential space within a sheath, most commonly the arachnoid membrane of the brain or the spinal cord.

Dosage Calculation

According to Ulusoy et al, vector titration requires a range between $10^9$ and $10^{13}$ genome copies (GC) per ml with a proven dosage of $10^{10}$-$10^{12}$ gc/ml. On the other hand, at any dilution ratio of the vectors to appraise they must have a low-medium range of $10^{11}$ gc/ml, which results in the disappearance of toxicity.

Dosage in Humans:

The dosage range in humans is found between $10^9$ and $10^{30}$ viral units/kg of body weight, without restricting this range to the application in different age groups or with modified volumes of distribution by age or pathology.

The greatest concentration or amount of a substance, found by experiment or observation that causes no detectable adverse alteration of morphology, functional capacity, growth, development, or life span of target organisms distinguishable from those observed in normal (control) organisms of the same species and strain under defined conditions of exposure.

Method of Application

The rAAV2 vectors were injected bilaterally into the NS using a 5 μL Hamilton syringe fitted with a glass capillary with a tip diameter of about 60-80 microns. Two microliters of the buffer containing the appropriate concentrations of viral particles were injected at a speed of 0.4 μl/minute. The needle was withdrawn slowly 5 minutes after completion of the injection.

The fragments obtained were set in a 1% agarose gel. Two types of molecular-weight size markers were used. The sizes are shown at the ends of the gel photograph:

1. pAAV_ATF6f-LFG-XBP1s-HA
2. pAAV_ATF6f-LF-XBP1s-HA
3. pAAV_ATF6f-L4H4-XBP1s-HA
4. pAAV_XBP1s-LFG-ATF6f-HA
5. pAAV_XBP1s-LF-ATF6f-HA
6. pAAV_XBP1s-L4H4-ATF6f-HA
7. pAAV_ATF6f-HA
8. pAAV_XBP1s-HA

Expected sizes after digestion with Eco R1:
1. 3895, 1928, 1531, 347 total size: 7701
2. 3895, 1928, 1639, 347 total size: 7809
3. 3895, 1928, 1549, 347 total size: 7719
4. 4262, 1928, 818, 693 total size: 7701
5. 4264, 1928, 926, 693 total size: 7809
6. 4264, 1928, 836, 693 total size: 7719
7. 3895, 1928, 693 total size: 6516
8. 4262, 1928, 347 total size: 6537

Figure 1:
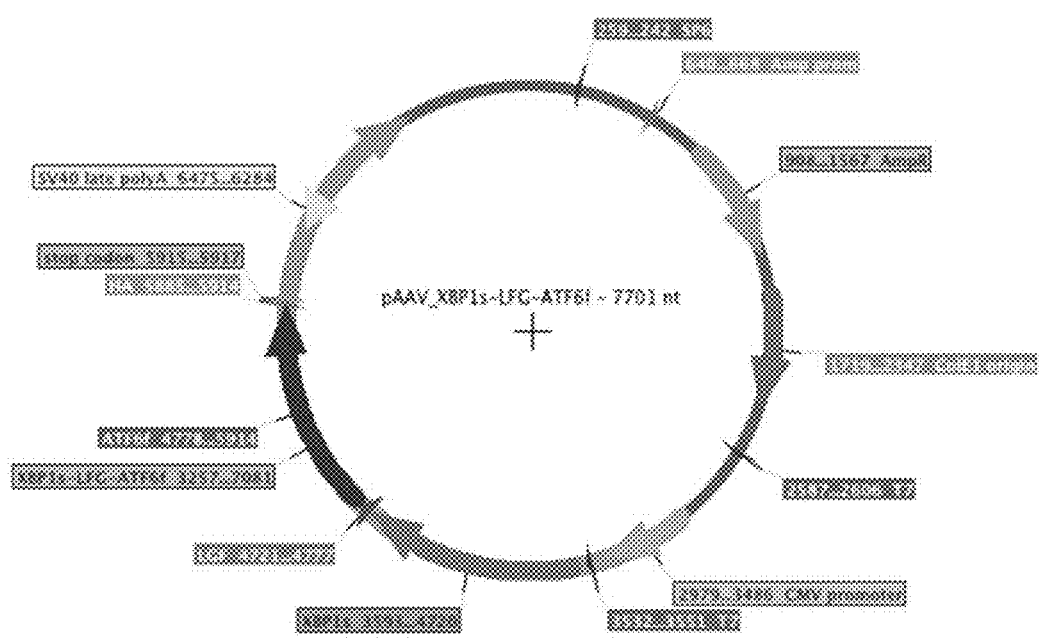
FIG. 1 shows a restriction map of the pAAV-XBP1-s-LFG-ATF6f plasmid, with 7701 bp and the representation of the genetic elements present in the generated recombinant DNA.
Figure 2:
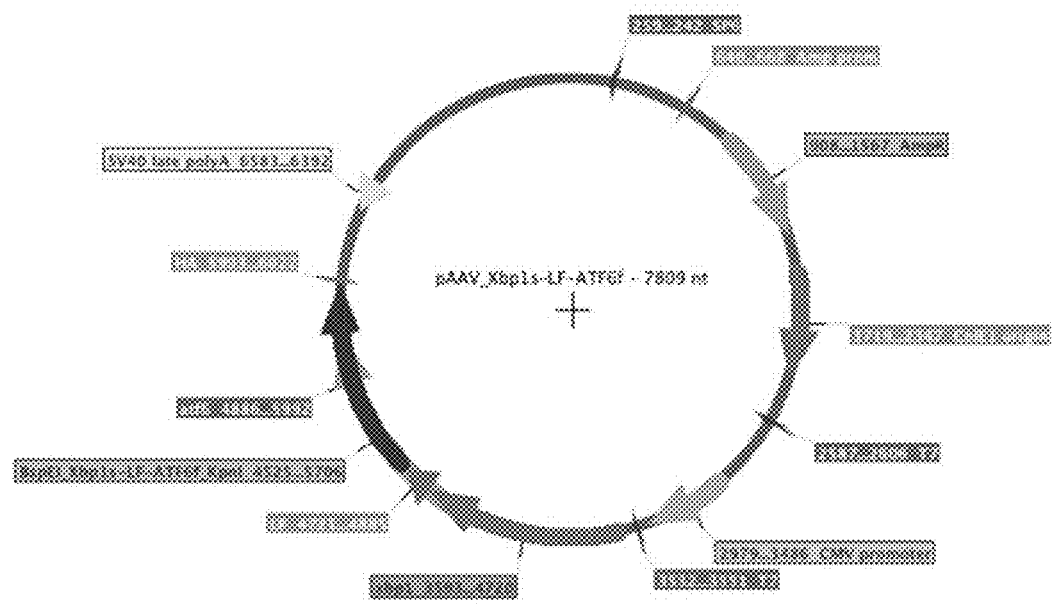
FIG. 2 shows a restriction map of the pAAV-XBP1s-LF-ATF6f plasmid, with 7809 bp and the representation of the genetic elements present in the generated recombinant DNA.
Figure 3:
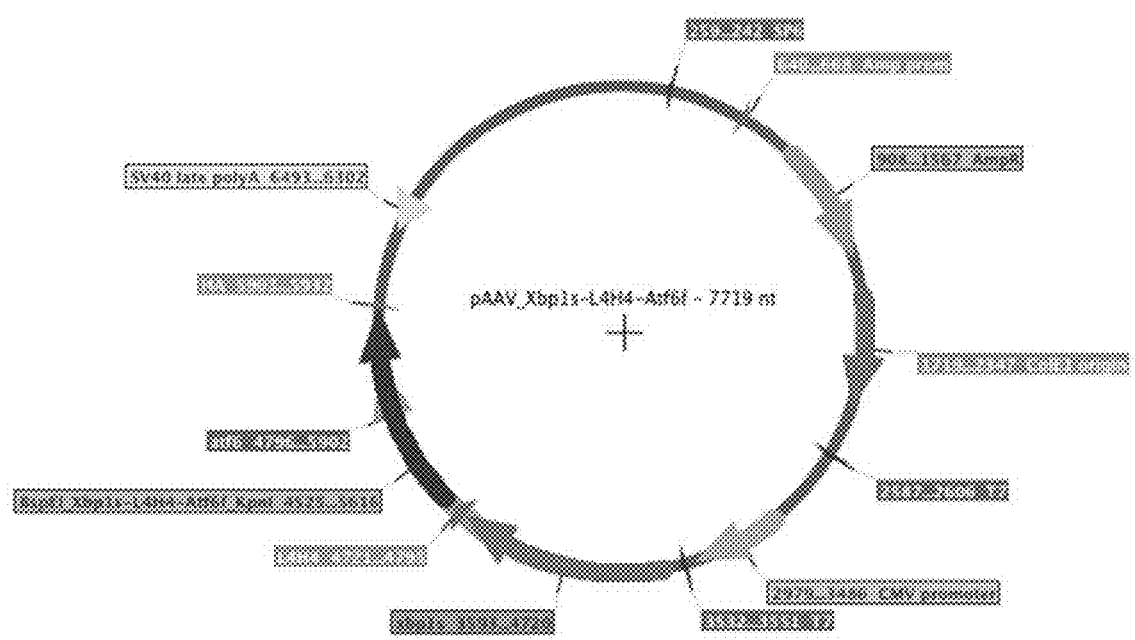
FIG. 3 shows a restriction map of the AAV-XBP1 s-L4H4-ATF6f plasmid with 7719 bp and the representation of the genetic elements present in the generated recombinant DNA.
Figure 4:
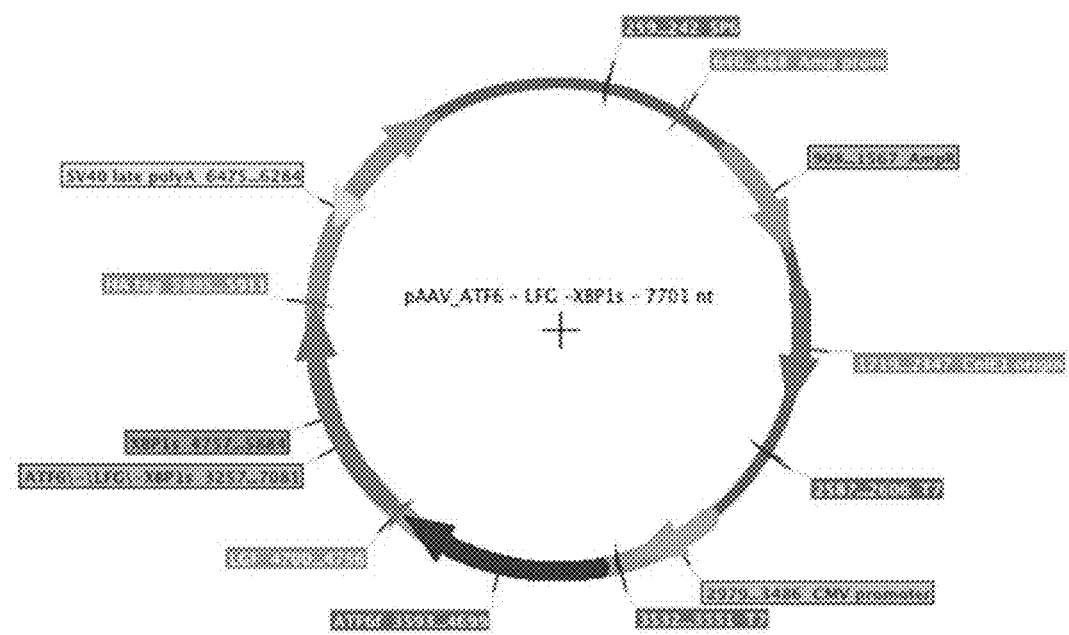
FIG. 4 shows a restriction map of the AAV-ATF6f-LFG-XBP1s plasmid with 7701 bp and the representation of the genetic elements present in the generated recombinant DNA.
Figure 5:
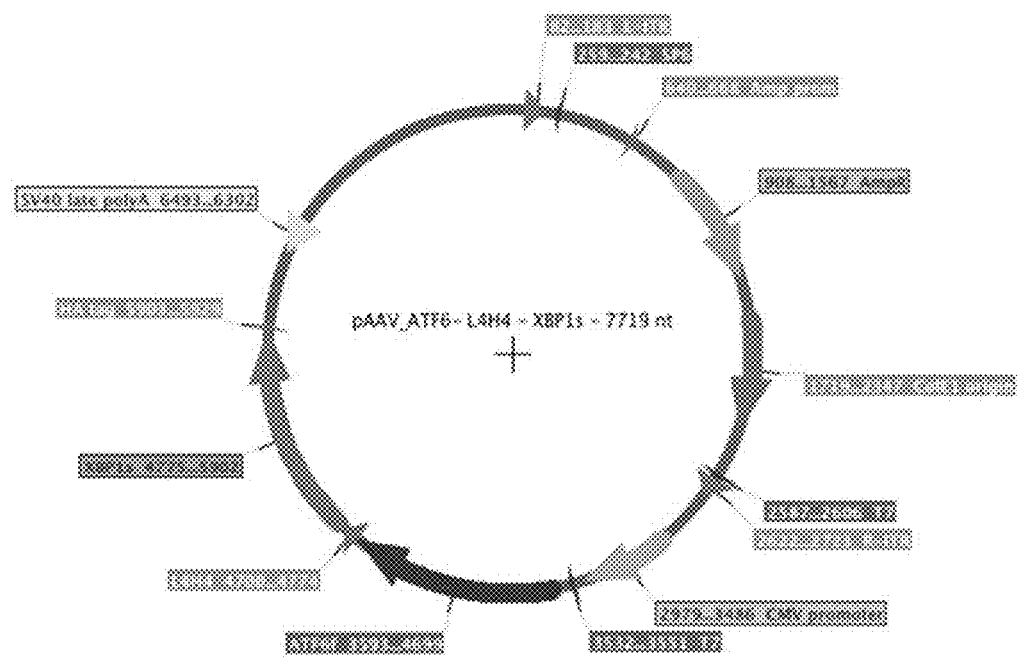
FIG. 5 shows a restriction map of the pAAV-ATF6f-L4H4-XBP1s plasmid with 7719 bp and the representation of the genetic elements present in the generated recombinant DNA.
Figure 6:
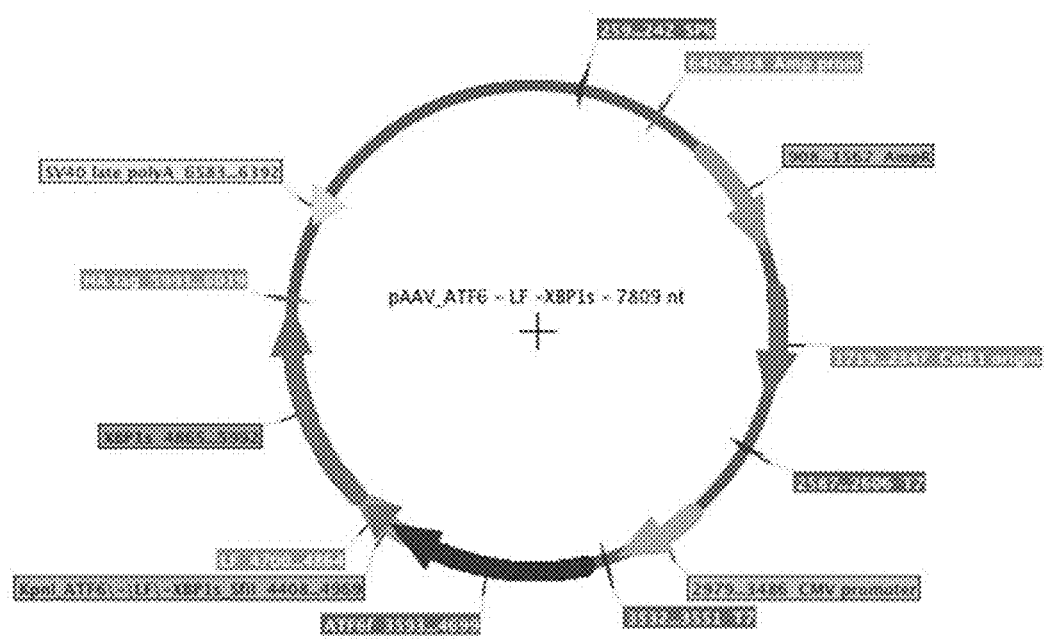
FIG. 6 shows a restriction map of the pAAV-ATF6f-LF-XBP1s plasmid with 7809 bp and the representation of the genetic elements present in the generated recombinant DNA.
Figure 7:
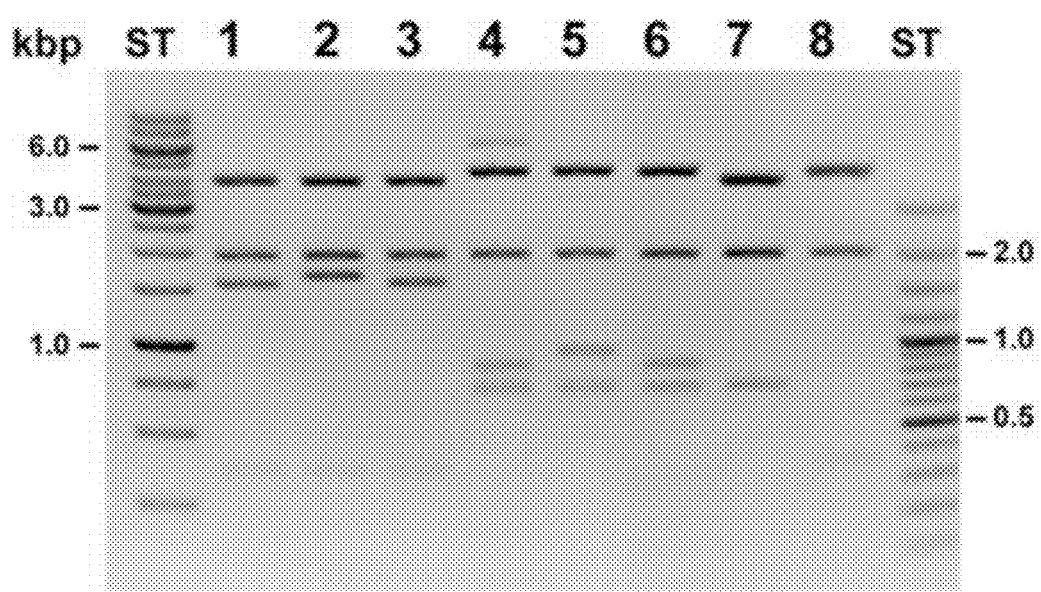
FIG. 7 shows a photograph of the restriction test of the UPRplus variants. A plasmid DNA digestion was performed with the restriction enzyme EcoR1 for two hours at 37 C.
Figure 8:
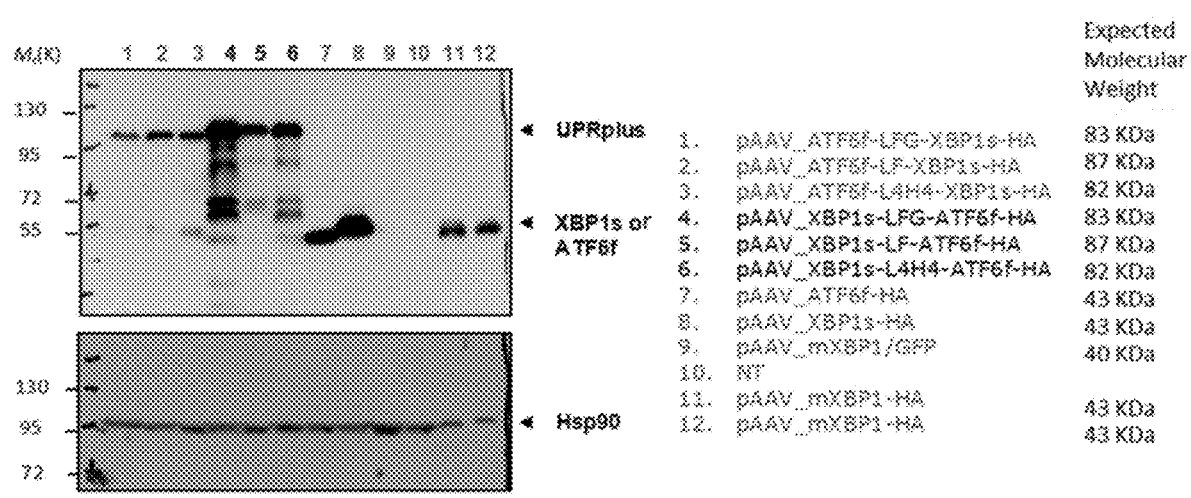

FIG. 8 shows the expression of UPRplus variants in HEK293 cells and their detection by HA epitope: The HEK293 cells were transiently transfected with the UPRplus variants. Encoding plasmids were used as a control for XBP1s-HA, ATF6-HA and XBP1s/GFP. In addition, an extract of non-transfected cells (NT) was included. After 48 hours of expression, the total proteins were extracted and the HA epitope was detected using the anti-HA Covance antibody (dilution 1:1000). mXBP1-HA was used as a positive control. Hsp90 was used as a load control.

Figure 9:
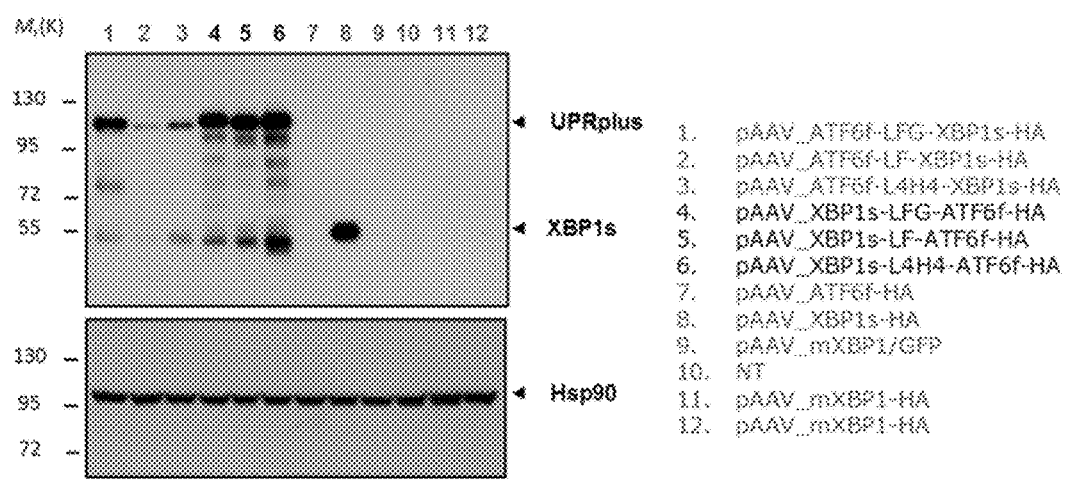

The sizes are shown at the ends of the gel photograph:
1. pAAV_ATF6f-LFG-XBP1s-HA expected molecular weight 83 KDa
2. pAAV_ATF6f-LF-XBP1s-HA expected molecular weight 87 KDa
3. pAAV_ATF6f-L4H4-XBP1s-HA expected molecular weight 82 KDa
4. pAAV_XBP1s-LFG-ATF6f-HA expected molecular weight 83 KDa
5. pAAV_XBP1s-LF-ATF6f-HA expected molecular weight 87 KDa
6. pAAV_XBP1s-L4H4-ATF6f-HA expected molecular weight 82 KDa
7. pAAV_ATF6f-HA expected molecular weight 43 KDa
8. pAAV_XBP1 s-HA expected molecular weight 43 KDa
9. pAAV_mXBP1/GFP expected molecular weight 40 KDa
10. NT
11. pAAV_mXBP1s-HA expected molecular weight 43 KDa
12. pAAV_mXBP1 s-HA expected molecular weight 43 KDa FIG. 9 shows the expression of the UPRplus variants in HEK293 cells and the detection of XBP1s therein. The HEK293 cells were transiently transfected with the UPRplus variants and with the encoding plasmids for XBP1s-HA, ATF6-HA, XBP1 s, and mXBP1s. In addition, extracts of non-transfected cells (NT) were used as a control. After 48 hours of expression, the total proteins were extracted and the XBP1 protein was detected using the Biolegend anti-XBP1 antibody, 143F, (dilution 1:1000). Hsp90 was used as a load control.

Figure 10:
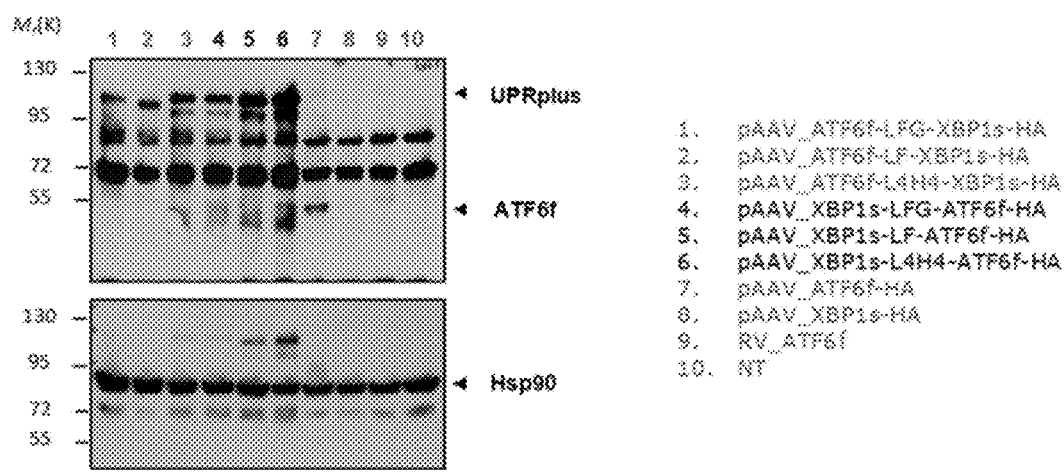

Identification of the gel lanes:
1. pAAV_ATF6f-LFG-XBP1s-HA
2. pAAV_ATF6f-LF-XBP1s-HA
3. pAAV_ATF6f-L4H4-XBP1s-HA
4. pAAV_XBP1 s-LFG-ATF6f-HA
5. pAAV_XBP1s-LF-ATF6f-HA
6. pAAV_XBP1 s-L4H4-ATF6f-HA
7. pAAV_ATF6f-HA
8. pAAV_XBP1s-HA
9. pAAV_mXBP1/GFP
10. NT
11. pAAV_mXBP1s-HA
12. pAAV_mXBP1s-HA FIG. 10 shows the expression of the UPRplus variants in HEK293 cells and the detection of ATF6. The HEK293 cells were transiently transfected with the UPRplus variants, and with the coding plasmids for XBP1 s-HA, ATF6-HA, BP1s, mXBP1s. In addition, non-transfected cells (NT) were used as a control. After 48 hours of expression, the total proteins were extracted and the ATF6 protein was detected using the anti-ATF6 antibody abCam (dilution 1:250). The expression of the mouse ATF6 protein was used as a positive control. Hsp90 was used as load control.

Figure 11:
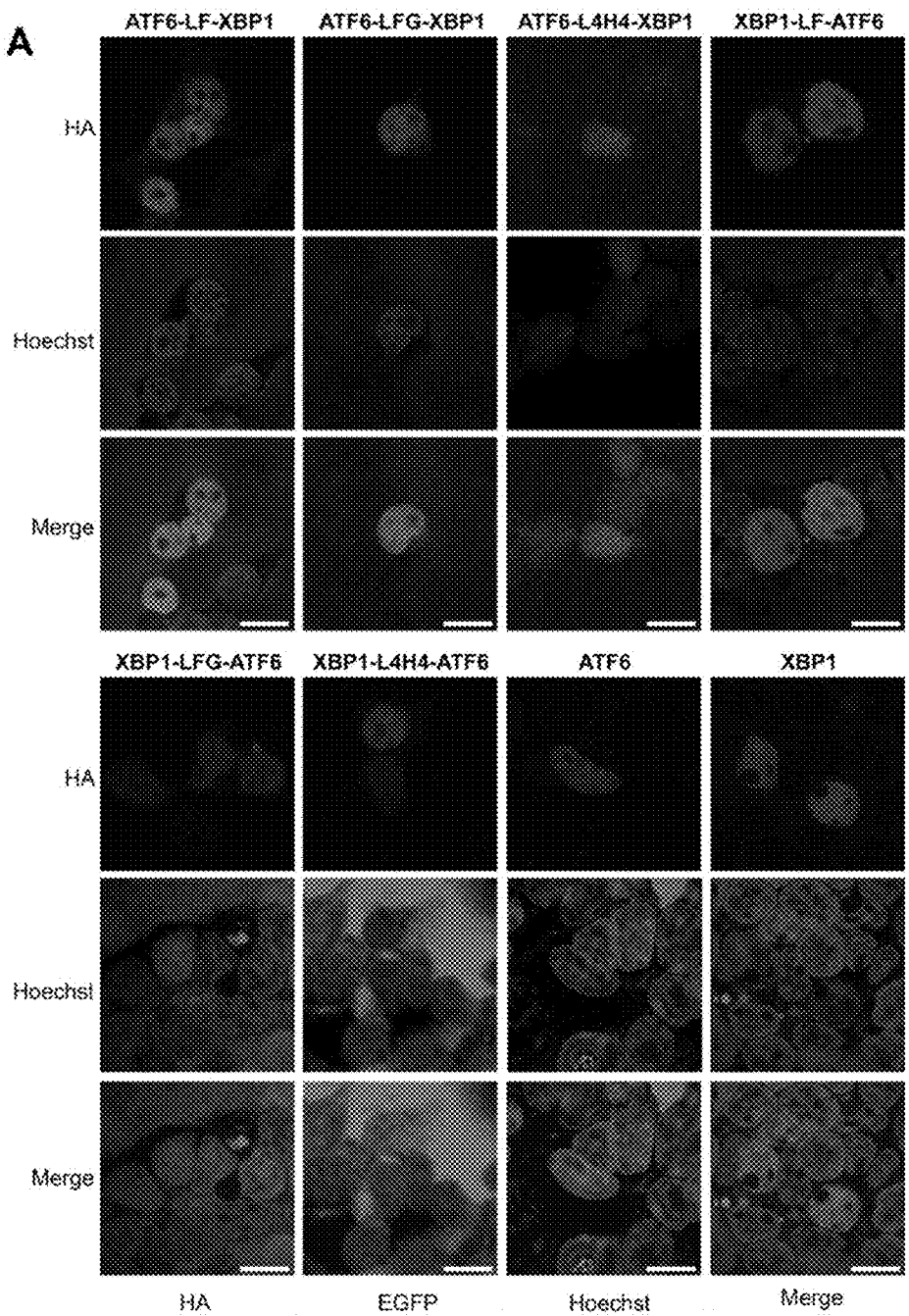
Figure 11:
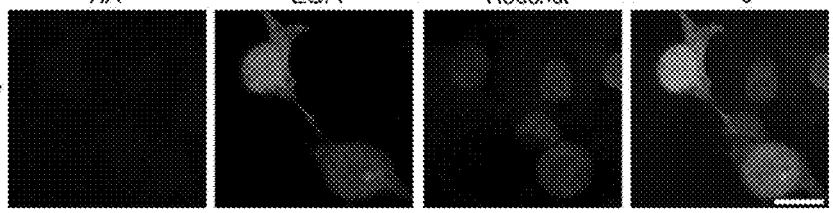

Identification of the gel lanes:
1. pAAV_ATF6f-LFG-XBP1s-HA
2. pAAV_ATF6f-LF-XBP1s-HA
3. pAAV_ATF6f-L4H4-XBP1s-HA
4. pAAV_XBP1s-LFG-ATF6f-HA
5. pAAV_XBP1s-LF-ATF6f-HA
6. pAAV_XBP1s-L4H4-ATF6f-HA
7. pAAV_ATF6f-HA
8. pAAV_XBP1s-HA
9. RV ATF6f
10. NT FIGS. 11A-B shows two groups of photographs, A and B, where one can observe the subcellular distribution of the UPRplus variants in HEK293 cells.

The group identified as (A) presents the HEK293 cells that were transfected with the different variants of UPRplus, fixed after 48 hours of expression and co-stained with anti-HA antibody (red, top panel) and Hoechst (blue, middle panel) in each condition. The overlay of images is displayed in the bottom panel of each condition.

The group identified as (B) presents the HEK293 cells that were transfected with mXBP1s/EGFP, fixed after 48 hours of expression and co-stained with anti-HA antibody (red), EGFP intrinsic fluorescence (green), and Hoechst (blue).

The bottom bar of each photograph corresponds to 10 μm.

FIGS. 12A-B shows two groups of photographs, A and B, which present the subcellular distribution of the UPRplus variants in HEK293 cells.

(A) The HEK293 cells were transfected with the different variants of UPRplus, fixed after 48 hours of expression and co-stained with anti-XBP1 antibody (red, top panel), and Hoechst stain (blue, middle panel) in each condition. The overlay of images is displayed in the bottom panel of each condition.

(B) The HEK293 cells were transfected with mXBP1s/EGFP, fixed after 48 hours of expression and co-stained with the anti-XBP1 antibody (red), EGFP intrinsic fluorescence (green), and Hoechst stain (blue).

The bottom bar of each photograph corresponds to 20 μm.

Figure 13:
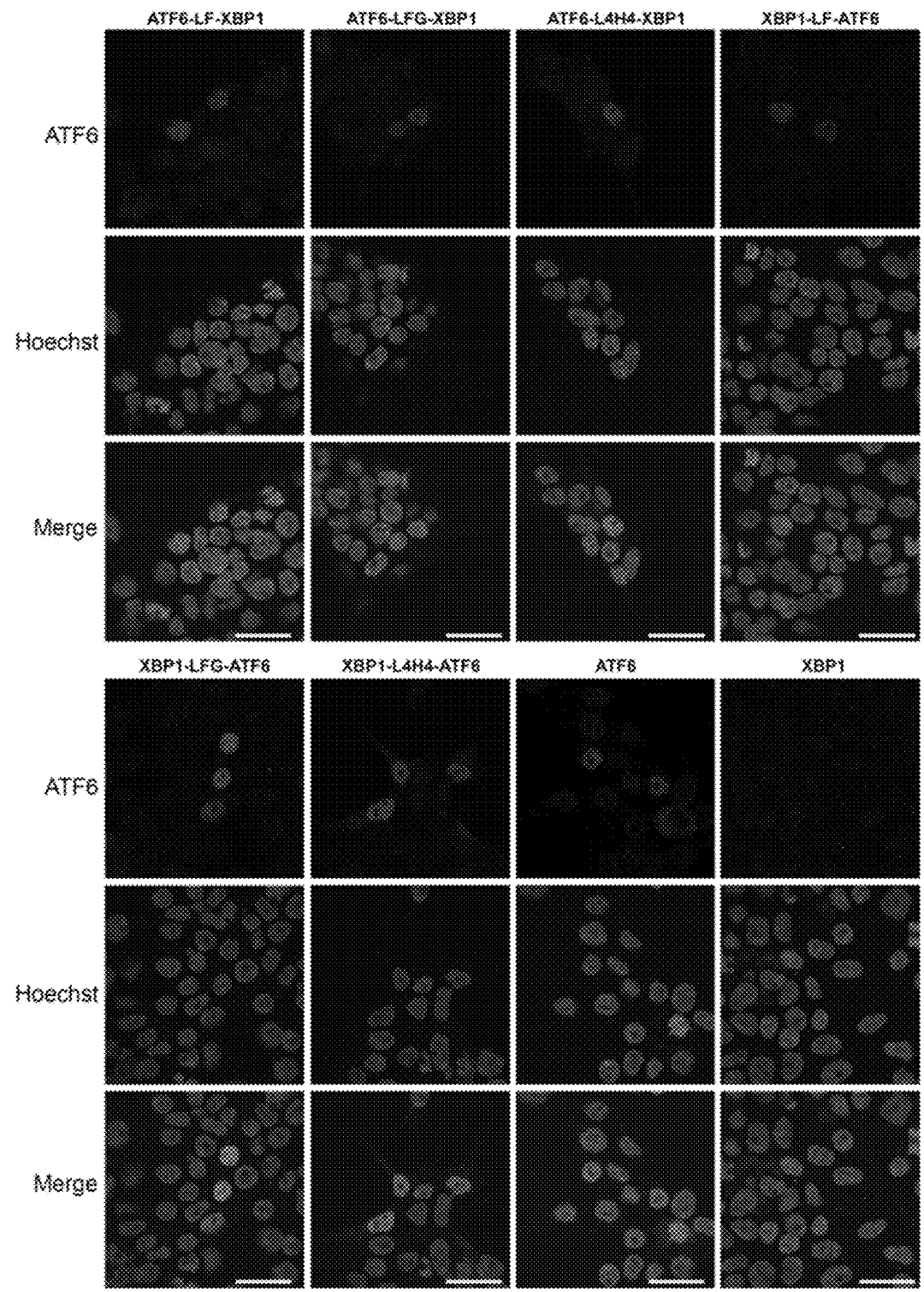

FIG. 13 analyzes the subcellular distribution of the UPRplus variants in HEK293 cells.

The HEK293 cells were transfected with the different variants of UPRplus, fixed after 48 hours of expression and co-stained with the anti-ATF6 antibody (red, top panel) and Hoechst stain (blue, middle panel) in each condition. The overlay of images is displayed in the bottom panel of each condition.

The lower bar of each photograph corresponds to 20 μm.

Figure 14:
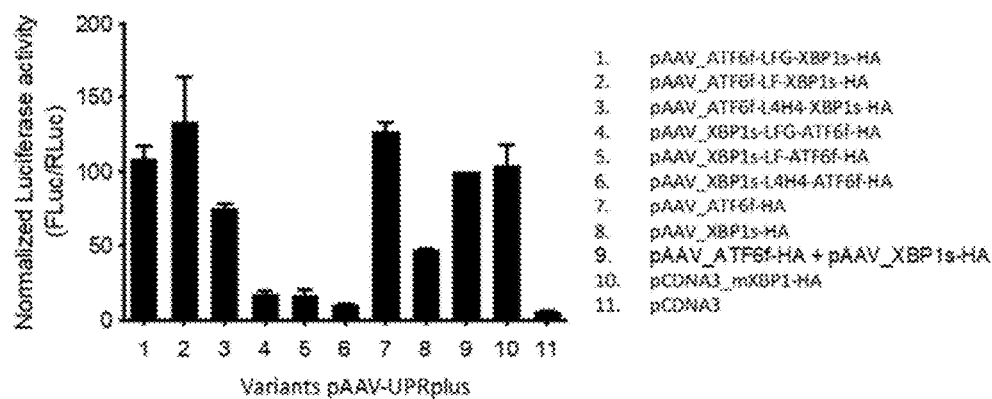

FIG. 14 presents a bar graph representing the transcriptional activity of the UPRplus variants:

The HEK293 cells were transiently transfected with three different plasmids:
the vectors encoding for the UPRplus variants;
the vector carrying the UPRE promoter region that controls luciferase expression; and
the renilla encoding plasmid, as an internal control.

The positive controls used were encoding plasmids for ATF6-HA, XBP1s-HA, and co-transfection of ATF6-HA/XBP1s-HA. Also, the transfected pCDNA3 empty vector was used as a negative control. After 48 hours of expression, the transcriptional activity was determined by means of a luciferase assay.

The luminescence measurement was conducted and normalized with the renilla activity.

The graph (top panel) represents the average of three independent experiments and the values are the mean and Standard Error of the Mean (SEM).

The table (bottom panel) shows the values obtained in each experiment for each experimental condition.

Figure 15:
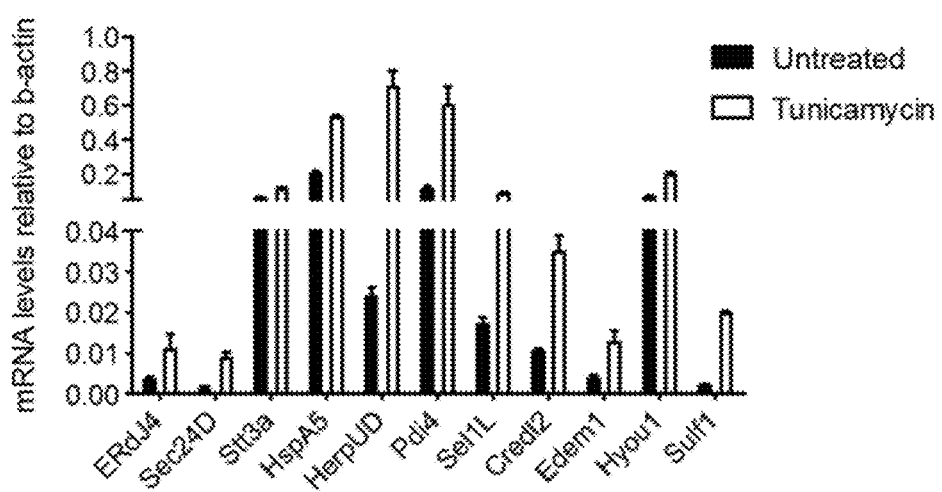

FIG. 15 shows an analysis of the expression of UPR target genes in HEK293 cells where:

The mRNA levels of the UPR-associated transcriptional targets were analyzed by real-time PCR from cDNA obtained from HEK293 cells under baseline conditions and treated with 1 μg/ml tunicamycin for 8 hours.

All samples were normalized with the expression levels of the constitutively active β-actin gene.

Figure 16:
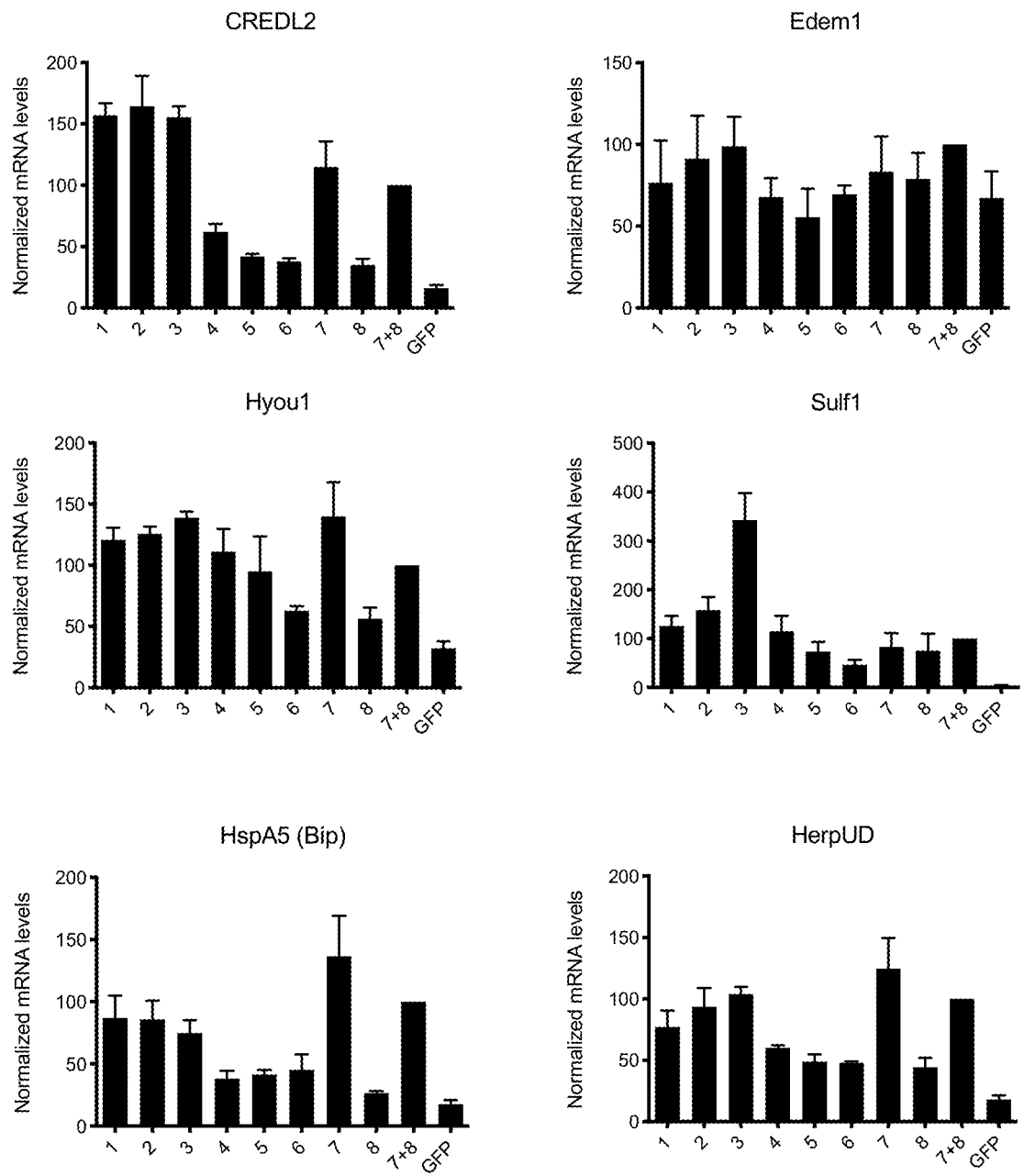

FIG. 16 shows an analysis of the expression of UPR target genes in HEK293 cells transfected with pAAV-UPRplus where:

The mRNA levels of the UPR-associated transcriptional targets were analyzed by real-time PCR from cDNA obtained from HEK293 cells transfected with the encoding plasmids for the six pAAV-UPRplus variants and the individual variants XBP1s and ATF6f, and the co-transfection of both variants (pAAV-XBP1s and pAAV-ATF6f).

All samples were normalized with the expression levels of the constitutively active β-actin gene.
1. pAAV_ATF6f-LFG-XBP1s-HA,
2. pAAV_ATF6f-LF-XBP1s-HA,
3. pAAV_ATF6f-L4H4-XBP1s-HA,
4. pAAV_XBP1s-LFG-ATF6f-HA,
5. pAAV_XBP1s-LFATF6f-HA,
6. pAAV_XBP1s-L4H4-ATF6f-HA,
7. pAAV_ATF6f-HA,
8. pAAV_XBP1s-HA,
7+8. pAAV_ATF6f-HA+pAAV_XBP1s-HA,
GFP. pAAV-EGFP.

FIGS. 17A-D presents a protein aggregation analysis of the polyQ79 protein (Example of Application) against the expression of UPRplus where:

(A) The N2A cells were transiently co-transfected with the pAAV-UPRplus, pAAV-XBP1s or pAAV-ATF6 vectors, and with the pEGFP-poly-Q79 vector. The protein expression was analyzed using Western blot, after 24 hours (right panel) and 48 hours (left panel) of expression. HSP90 was used as a load control.

(B) These same samples were analyzed by Filter-trap assay after 24 hours (right panel) and 48 hours (left panel) of expression.

(C) Graph that represents the quantification of the protein aggregation of the polyQ79 protein using Western blot after 24 hours (right panel) and 48 hours (left panel) of expression. The mean and standard error of three independent experiments are shown.

(D) Graph that represents the quantification of the protein aggregation of polyQ79 using Filter-trap after 24 hours (right panel) and 48 hours (left panel) of expression. The mean and standard error of three independent experiments are shown.

EXAMPLE OF APPLICATION

Figure 17:
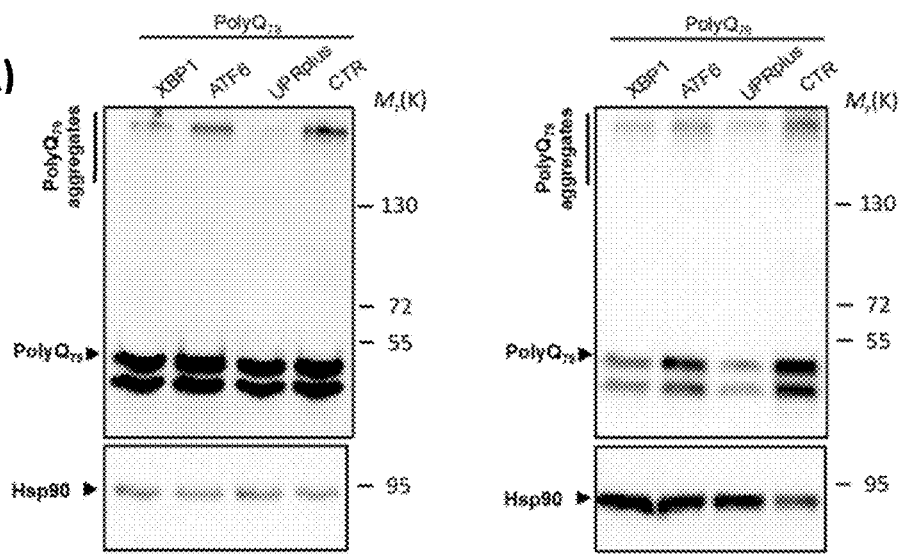
Figure 17:
Figure 17:
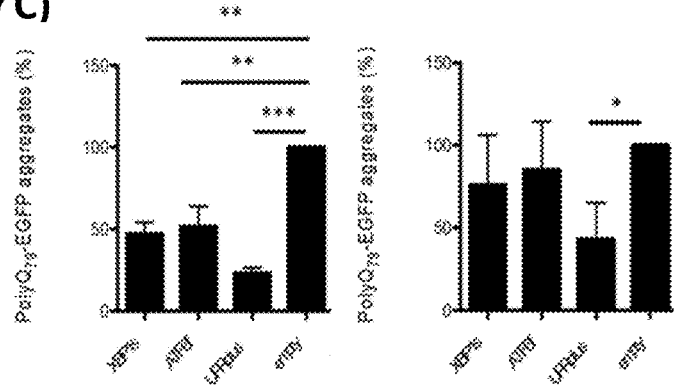
Figure 17:
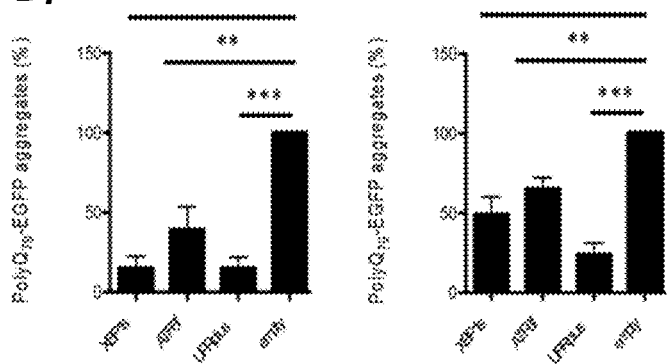

Parkinson's and Huntington's diseases are related to the formation of protein aggregates that cause selective neuronal death, preferentially in the dopaminergic neurons of the substantia nigra. To observe these effects, a Western blot test was conducted, as shown in FIG. 17, where:

$3\times10^5$ N2A cells were seeded in 30 mm wells. After 24 hours, the pAAV-UPRplus, pAAV-XBP1s or pAAV-ATF6 vectors were co-transfected and the pEGFP-poly-079 vector was used with the Effectene method. 0.6 µg of each vector plus 3.2 µl of Enhancer and 100 µl of EC buffer were mixed. The mixture was shaken by vortex for 15 seconds and incubated at room temperature for 10 minutes. 8 µl of Effectene (Qiagen) was added, shaken by vortex for 10 seconds, and incubated at room temperature for 15 minutes. The solution was mixed with 500 µl DMEM 10% SFB medium and added to the drip culture plate covering the entire surface.

After 24 or 48 hours of expression, the cells were removed from the culture plate using a cell scraper, collected, and centrifuged at 2,000 rpm for 5 minutes at 4° C. The precipitate was re-suspended in a PBS buffer with 1% Triton, supplemented with protease inhibitor (Roche). The cells were sonicated 3 times for 5 seconds on ice and, finally, the protein concentration was determined in each sample using the BCA Protein Assay (Pierce, Rockford, Ill.) (Zhang et al. 2014).

The protein samples were prepared using 25 µg of total protein, mixed with 4× charge buffer (Tris-HCl 0.2 M [pH 6.8], SOS 10%, bromophenol blue 0.05%, and glycerol 20%) and then heated for 5 minutes at 95° C., which were loaded into 8% denaturant gels. The 8% polyacrylamide separator gel was prepared with Tris-HCl 380 mM [pH 8.3], acrylamide-bis-acrylamide 8%, SDS 0.1%, ammonium persulfate 0.1% and TEMED 0.06%. The compressor polyacrylamide gel was prepared with Tris-HCl 60 mM [pH 6.8], acrylamide-bis-acrylamide 4%, SDS 0.1%, ammonium persulfate 0.1% and TEMEO 0.06%.

The electrophoresis was conducted in running buffer (Tris 25 mM, Glycine 250 mM and SDS 0.1%) at a constant voltage of 100 V. The electrophoretic running was stopped when the blue front left the gel. Subsequently, the proteins were transferred to a PVDF membrane in transfer buffer (Tris 25 mM, Glycine 250 mM and methanol 20%) at a constant voltage of 100V for 2 hours 30 minutes on ice. The membrane was then incubated in blocking solution (5% milk in PBS) for 1 hour at room temperature and constant agitation. Finally, the membranes were incubated with any of the following antibodies, diluted in 5% milk PBS 0.02% Tween; anti-GFP 1:1000 (Santa Cruz) or anti-HSP90 1:3000 (Santa Cruz), for 16 hours at 4° C. while in constant agitation. The following day, the membranes were washed 3 times for 5 minutes with PBS Tween 0.1% and later incubated for 1 hour at room temperature and constant agitation with the relevant secondary antibodies: anti-rabbit-HRP or anti-mouse-HRP (Invitrogen) diluted 1:3000 (Milk 5% in PBS Tween 0.02%). Once this period had transcurred, the membranes were washed with PBS Tween 0.1%, this time 3 times for 5 minutes. Finally, protein analysis was done using the Western Blotting Substrate kit (Pierce) and the Chemidoc image detection system (Biorad).

To confirm the above-obtained data, a Filtertrap assay was conducted, where 25 µg of total protein mixed with PBS-SDS 4× buffer was used to conduct this.

These samples were loaded onto a 96 well plate coupled to a vacuum pump containing cellulose acetate filters. After adding the samples, vacuum was applied to retain only high molecular weight species in the filter. Subsequently, the filters were incubated in blocking solution (5% milk in PBS) for 1 hour at room temperature and while in constant agitation. They were later incubated with the anti-GFP antibody 1:1000 (Santa Cruz), diluted in 5% milk PBS Tween 0.02% for 16 hours at 4° C. with constant agitation. The following day, the filters were washed 3 times for 5 minutes with PBS Tween 0.1% and later incubated for 1 hour at room temperature and constant agitation with the secondary anti-mouse-HRP antibody (Invitrogen) diluted 1:3000 (5% milk in PBS Tween 0.02%).

After this period, the membranes were washed with PBS Tween 0.1%, this time 3 times for 5 minutes. Finally, protein analysis was done using the Western Blotting Substrate kit (Pierce) and the Chemidoc image detection system (Biorad).

Conclusions:

With the expression of the UPRplus, XBP1 s and ATF6f proteins for 24 hours, the percentage of aggregation of the polyQ 79-EGFP protein in the N2A cell managed to be reduced. The expression of the UPRplus, XBP1s and ATF6f proteins managed to be reduced to 23.2, 47, and 51.4%, respectively, the percentage of aggregation determined using WB.

The anti-aggregation effect was also determined using the Filtertrap technique, in which case the expression of the UPRplus, XBP1s and ATF6f proteins dropped to 15.1, 15, and 39.1% respectively, after 24 hours.

In addition, the anti-aggregation effect of the expression of the XBP1s, ATF6f and UPRplus proteins was evaluated using WB after 48 hours. It was observed that the aggregation of polyQ79 dropped significantly only with UPRplus treatment (47% decrease).

Moreover, the Filtertrap technique, it was observed that the expression of the XBP1s, ATF6f and UPRplus proteins decreased the protein aggregation of polyQ79-GFP to 48.5; 65.6 and 24% respectively, with respect to the control, after 48 hours.

Material and Methods

Adena-Associated Vector Production

The AAV virus serotype 2 (AAV2/6) particles were produced by the transfection of 293-AAV cells (Agilent Technologies, Santa Clara, Calif.) and purified in an iodixanol gradient followed by column affinity chromatography. The number of AAV particles that the genome contains in the suspension as well as the infectivity of the suspension of the vector in HEK293T cells were determined by TaqMan qPCR assays.

Preparation of the Adenoviral Plasmids (pAAV) for the 6 Variants:

For the development of this target, the XBP1 s sequences, human ATF6f sequences, and the respective linkers were synthesized de novo and cloned into the adenoviral plasmid pAAV-CMV-MCS, which expresses the transgene under the CMV promoter. The HA tag sequence (FIG. 17A) was included in all the generated constructs, which then allowed us to identify the transduced cells. The empty adenoviral plasmid pAAV-CMV-MCS was used as control.

To confirm the expression of the generated constructs we transfected HEK cells with the different constructs, after 48 hours of transfection we performed the extraction of proteins that were evaluated by means of WB using an anti-HA antibody.

As shown in FIG. 10, we detected a band with the expected molecular weight for the variants UPRplus (130 kDa) along with the expression controls for pAAV-XBP1s-HA (55 kDa), pAAV-ATF6f-HA (55 kDa) and pCDNA-mXBP1s (55 kDa).

Real-Time PCR

Total RNA was isolated from HEK 293 cells transfected with the different plasmids. After homogenization in PBS, the Trizol RNA extraction protocol recommended by the manufacturer was followed. The cDNA was synthesized with a high-capacity cDNA reverse transcription kit (Applied Biosystems). SYBR green and a Mx3005P QPCR System (Stratagene) were used for quantitative RT-PCR. The relative quantification of mRNA was calculated by the comparative threshold cycle method with β-actin as control. The primers of the sequences were obtained from the PrimerBank (Table XV).

TABLE XV

| | | |
|---|---|---|
| Erdj4 | 5'-GGAAGGAGGAGCGCTAGGTC-3 | 5'-ATCCTGCACCCTCCGACTAC-3' |
| HspA5 (BiP) | 5'-GCCTGTATTTCTAGACCTGCC-3' | 5'-TTCATCTTGCCAGCCAGTTG-3' |
| HerpUD | 5'-AACGGCATGTTTTGCATCTG-3' | 5'-GGGGAAGAAAGGTTCCGAAG-3' |
| Hyou 1 | 5'-GCAGACCTGTTGGCACTGAG-3' | 5'-TCACGATCACCGGTGTTTTC-3' |
| Pdia4 | 5'-AGTGGGGAGGATGTCAATGC-3' | 5'-TGGCTGGGATTTGATGACTG-3' |
| Sec24D | 5'-AGCAGACTGTCCTGGGAAGC-3' | 5'-TTTGTTTGGGGCTGGAAAAG-3' |
| SeI1L | 5'-ATCTCCAAAAGGCAGCAAGC-3' | 5'-TGGGAGAGCCTTCCTCAGTC-3' |
| Stt3a | 5'-TTCAACCTGGGTGACCAGTG-3' | 5'-CATGACCTTCGCATCCTCTG-3' |
| Sulf1 | 5'-ATTCAAGGAGGCTGCTCAGG-3' | 5'-TGTCATGCGTGAAGCAAGTG-3' |

Western Blot

This technique is described in detail in Experiment 1.

Cultures

Neuro2A cells and HEK293T cells were obtained from ATCC and cultured in DMEM medium supplemented with 10% bovine serum or 5%, respectively, and antibiotics (10000 U/ml penicillin, 10 mg/ml streptomycin), at 37° C. and 5% $CO_2$.

Assays

Filtertrap assay: 25 ug of total protein are applied to a 96 well plate coupled to a vacuum pump (Microfiltration Apparatus, bio-rad, http://www.bio-rad.com/en-us/applications-technologies/protein-blotting-equipment-cells-power-supplies#3) containing cellulose acetate filters.

After adding the samples, vacuum was applied to retain only high molecular weight species in the filter. The filters were then incubated in blocking solution (5% milk in PBS) for 1 hour under agitation at room temperature. They were then incubated with the anti-GFP antibody 1:1000 (Santa Cruz), diluted in 5% milk/PBS Tween 0.02% 16 hours at 4° C. under agitation. The next day the filters were washed 3 times for 5 minutes with PBS Tween 0.1% and then incubated for 1 hour at room temperature under constant agitation with the secondary anti-mouse-HRP antibody (Invitrogen) diluted 1:3000 (5% milk/PBS Tween 0.02%).

Effectene Method: This method consists of a method of transfection of plasmids into eukaryotic cells, which is described and standardized by the manufacturer's protocol (Qiagen) (https://www.qiagen.com/es/shop/assay-technologies/transfection-reagents/effectene-transfection-reagent/).

This protocol consists of mixing 0.6 µg of each vector plus 3.2 µl of Enhancer and 100 µl of EC buffer. The mixture is shaken by vortex for 10 seconds and incubated at room temperature for 10 minutes. Then, 8 µl of Effectene was added, shaken by vortex for 10 seconds and incubated at room temperature for 15 minutes. This solution is mixed with 500 µl of DMEM 10% FBS medium and added to the 30 mm drip culture plate covering the entire surface.

Statistics

The data are expressed as mean and SEM. Depending on the experiments, the results were statistically compared using Student's T-test or Mann-Whitney's test, two-way ANOVA, followed by Holm-Sidack or Bonferroni as a post-hoc test or Kruskal-Wallis by one-way ANOVA on ranks followed by the Dunn's test or Bonferroni as a post-hoc test.

Possible Example Implementations

The subject matter of this disclosure may be implemented in accordance with one or more of the following example implementations, or any combination or modification of the described aspects of the following example implementations that might be apparent to a person of ordinary skill in the art based on this disclosure.

Example implementation 1: An adeno-associated vector (AAV), WHEREIN it comprises a recombinant viral genome where such genome comprises an expression cassette comprising a regulating region of the specific transcription of neuronal tissues operatively bound to a UPRplus polynucleotide of interest coding a fusion protein.

Example implementation 2: An adeno-associated vector, according to Example implementation 1, WHEREIN the serotype of the AAV is selected from a group that comprises AAV2, AAV6, AAV7, AAV8, AAV9, AAV10, AAV11 and pseudo-typed AAVs.

Example implementation 3: An adeno-associated vector, according to Example implementation 2, WHEREIN the serotype of the AAV is AAV 2.

Example implementation 4: An adeno-associated vector, according to Example implementations 1, 2 and 3, WHEREIN the transcription regulatory region includes a selected promoter region from the group that comprises CMV, PGK1, CAMKll, THY1, GAD34, among others.

Example implementation 5: An adeno-associated vector, according to Example implementation 4, WHEREIN the selected promoter region of the group is CMV.

Example implementation 6: An adeno-associated vector, according to Example implementations 1, 2 and 3, WHEREIN it comprises a coding region for an immune response site selected from the Ha, Flag, Gfp, His and Myc group, among others.

Example implementation 7: An adeno-associated vector, according to Example implementation 6, WHEREIN the coding region for an immune response site is Ha.

Example implementation 8: An adeno-associated vector, according to Example implementation 4, WHEREIN the adeno-associated vector's type of serotype provides the specificity of the cellular type that the transgene will express given the tropism of each serotype.

Example implementation 9: An adeno-associated vector, according to Example implementation 8, WHEREIN the adeno-associated vector's type of serotype is specific to the specific neuronal cellular type.

Example implementation 10: An adeno-associated vector, according to Example implementation 9, WHEREIN the adeno-associated vector's type of serotype is of the number 2 and/or a 2/6 pseudo-typed vector.

Example implementation 11: An adeno-associated vector, according to Example implementations 1-10, WHEREIN the expression cassette comprises a post-transcriptional regulatory region.

Example implementation 12: An adeno-associated vector, according to Example implementation 11, WHEREIN the post-transcriptional regulatory region is the post-transcriptional regulatory element of the Woodchuck Hepatitis Virus (WHP).

Example implementation 13: An adeno-associated vector, according to Example implementations 1 to 12, WHEREIN the IRTs of the adeno-associated virus are IRTs derived from AAV2, AAV6, AAV7, AAV8, AAV9, AAV10, AAV11 and pseudo-typed AAVs, preferentially AAV2.

Example implementation 14: An adeno-associated vector, according to Example implementations 1 to 13, WHEREIN the UPRplus target sequences to be transcribed comprise XBP1s, ATF6f and a bridge or linker sequence.

Example implementation 15: An adeno-associated vector, according to Example implementation 14, WHEREIN the bridge sequence comprises the LGF, L4H4 and LF sequences.

Example implementation 16: An adeno-associated vector, according to Example implementations 14 and 15, WHEREIN the target sequence to be transcribed is XBP1s-LGF-ATF6f-HA.

Example implementation 17: An adeno-associated vector, according to Example implementations 14 and 15, WHEREIN the target sequence to be transcribed is XBP1s-LF-ATF6f-HA.

Example implementation 18: An adeno-associated vector, according to Example implementations 14 and 15, WHEREIN the target sequence to be transcribed is XBP1s-L4H4-ATF6f-HA.

Example implementation 19: An adeno-associated vector, according to Example implementations 14 and 15, WHEREIN the target sequence to be transcribed is ATF6f-LGF-XBP1s-HA.

Example implementation 20: An adeno-associated vector, according to Example implementations 14 and 15, WHEREIN the target sequence to be transcribed is ATF6f-LF-XBP1s-HA.

Example implementation 21: An adeno-associated vector, according to Example implementations 14 and 15, WHEREIN the target sequence to be transcribed is ATF6f-L4H4-XBP1s-HA.

Example implementation 22: An adeno-associated vector, according to Example implementations 1 to 21, WHEREIN the polynucleotide of interest encodes fusion proteins within the group comprising XBP1s-LGF-ATF6f-HA, XBP1s-LF-ATF6f-HA, XBP1s-L4H4-ATF6f-HA, ATF6f-LGF-XBP1s-HA, ATF6f-LF-XBP1s-HA and ATF6f-L4H4-XBP1s-HA, which act systemically close to or with neuronal cells.

Example implementation 23: An adeno-associated vector, according to Example implementation 22, WHEREIN the polynucleotide of interest encodes the fusion protein XBP1s-LGF-ATF6f-HA.

Example implementation 24: An adeno-associated vector, according to Example implementation 22, WHEREIN the polynucleotide of interest encodes the fusion protein XBP1s-LF-ATF6f-HA.

Example implementation 25: An adeno-associated vector, according to Example implementation 22, WHEREIN the polynucleotide of interest encodes the fusion protein XBP1s-L4H4-ATF6f-HA.

Example implementation 26: An adeno-associated vector, according to Example implementation 22, WHEREIN the polynucleotide of interest encodes the fusion protein ATF6f-LGF-XBP1s-HA.

Example implementation 27: An adeno-associated vector, according to Example implementation 22, WHEREIN the polynucleotide of interest encodes the fusion protein ATF6f-LF-XBP1s-HA.

Example implementation 28: An adeno-associated vector, according to Example implementation 22, WHEREIN the polynucleotide of interest encodes the fusion protein ATF6f-L4H4-XBP1s-HA.

Example implementation 29: An adeno-associated vector, according to Example implementation 22, WHEREIN the polynucleotide of interest that acts systemically close to or with neuronal cells is specific to the cells involved in neurodegeneration.

Example implementation 30: An adeno-associated vector, according to Example implementations 22 and 29, WHEREIN the polynucleotide of interest that acts systemically close to or with neuronal cells is specific to the cells involved in Parkinson's and Huntington's diseases.

Example implementation 31: An adeno-associated vector, according to Example implementation 30, WHEREIN the polynucleotide of interest that acts systemically close to or with neuronal cells is specific to the cells involved in Parkinson's disease, preferentially in the dopaminergic neurons of the substantia nigra, and is also specific to GABAergic neuronal cells called medium spiny neurons (MSNs) of the striatum, involved in Huntington's disease.

Example implementation 32: A pharmaceutical composition, WHEREIN it comprises an adeno-associated vector described in the previous Example implementations and pharmaceutically acceptable excipients.

Example implementation 33: A pharmaceutical composition, according to Example implementation 32, WHEREIN it comprises a dosage of the virus at a range between $10^9$ to $10^{13}$ genome copies (GC) per ml of compound.

Example implementation 34: Use of a pharmaceutical composition, according to Example implementation 32, WHEREIN it is useful in the preparation of a drug for the treatment of a neurodegenerative disease.

Example implementation 35: Use of an adeno-associated vector, according to Example implementation 1, WHEREIN it is useful in the preparation of a drug for the treatment of a neurodegenerative disease, in a mammal.

Example implementation 36: Use of an adeno-associated vector, according to Example implementation 35, WHEREIN it is useful in the preparation of a drug for the treatment of Parkinson's and/or Huntington's disease.

Example implementation 37: Use of an adeno-associated vector, according to Example implementation 35, WHEREIN this mammal is a human.

Example implementation 38: Use of an adeno-associated vector, according to Example implementation 35, WHEREIN the adeno-associated vector or the pharmaceutical composition is administered systemically or locally.

Example implementation 39: Use of an adeno-associated vector, according to Example implementation 35, WHEREIN the adeno-associated vector or the pharmaceutical composition requires the expression of the polynucleotide of interest in the neuronal tissue.

Example implementation 40: Therapeutic method of application with an adeno-associated vector, according to Example implementation 1, WHEREIN it comprises:
  a: Bringing the neuronal cells into contact with the adeno-associated virus described in Example implementations 1 to 31; and
  b: The expression of the virus in the neuronal cells.

Example implementation 41: Therapeutic method of application with an adeno-associated vector, according to Example implementation 40, WHEREIN the routes of administration are subject to the passage of the virus of the blood-brain barrier and comprises the nasal route; by direct intraventricular and/or intrathecal injection, among others.

Example implementation 42: A polynucleotide, WHEREIN it comprises an expression cassette flanked by the ITRs of an adeno-associated virus, where such expression cassette comprises a promoter, a coding region for immune response, and a polynucleotide of interest that encodes a fusion protein.

Example implementation 43: A polynucleotide, according to Example implementation 42, WHEREIN the promoter region is selected from the group that comprises CMV, PGK1, CAMKll, THY1 and GAD34 among others.

Example implementation 44: A polynucleotide, according to Example implementation 43, WHEREIN the promoter region selected from the group is CMV.

Example implementation 45: A polynucleotide, according to Example implementation 42, WHEREIN it comprises a coding region for an immune response site selected from the group Ha, Flag, Gfp, His and Myc, among others.

Example implementation 46: A polynucleotide, according to Example implementation 45, WHEREIN the coding region for an immune response site is Ha.

Example implementation 47: A polynucleotide, according to Example implementation 42, WHEREIN the type of serotype of the adeno-associated vector provides the specificity of the cellular type that will express the transgene given the tropism of each serotype.

Example implementation 48: A polynucleotide, according to Example implementation 47, WHEREIN the type of serotype of the adeno-associated vector is specific to the specific neuron cellular type.

Example implementation 49: A polynucleotide, according to Example implementation 48, WHEREIN the type of serotype of the adeno-associated vector is of the number 2 and/or a 2/6 pseudo-typed vector.

Example implementation 50: A polynucleotide, according to Example implementations 42 to 29, WHEREIN the expression cassette also comprises a post-transcriptional regulatory region.

Example implementation 51: A polynucleotide, according to Example implementation 50, WHEREIN the post-transcriptional regulatory region is the post-transcriptional regulatory element of the Woodchuck Hepatitis Virus (WHP).

Example implementation 52: A polynucleotide, according to Example implementations 42 to 51, WHEREIN the target sequences to be transcribed comprise XBP1s-LGF-ATF6f-HA, XBP1s-LF-ATF6f-HA, XBP1s-L4H4-ATF6f-HA, ATF6f-LGF-XBP1s-HA, ATF6f-LF-XBP1s-HA and ATF6f-L4H4-XBP1s-HA, which act systemically close to or with neuronal cells.

Example implementation 53: A polynucleotide, according to Example implementation 52, WHEREIN the target sequence to be transcribed is XBP1s-LGF-ATF6f-HA.

Example implementation 54: A polynucleotide, according to Example implementation 52, WHEREIN the target sequence to be transcribed is XBP1s-LF-ATF6f-HA.

Example implementation 55: A polynucleotide, according to Example implementation 52, WHEREIN the target sequence to be transcribed is XBP1s-L4H4-ATF6f-HA.

Example implementation 56: A polynucleotide, according to Example implementation 52, WHEREIN the target sequence to be transcribed is ATF6f-LGF-XBP1s-HA.

Example implementation 57: A polynucleotide, according to Example implementation 52, WHEREIN the target sequence to be transcribed is ATF6f-LF-XBP1s-HA.

Example implementation 58: A polynucleotide, according to Example implementation 52, WHEREIN the target sequence to be transcribed is ATF6f-L4H4-XBP1s-HA.

Example implementation 59: A polynucleotide, according to Example implementations 42 to 58, WHEREIN the polynucleotide of interest encodes proteins within the group comprising XBP1s-LGF-ATF6f-HA, XBP1s-LF-ATF6f-HA, XBP1s-L4H4-ATF6f-HA, ATF6f-LGF-XBP1s-HA, ATF6f-LF-XBP1s-HA and ATF6f-L4H4-XBP1s-HA, which act systemically close to or with neuronal cells.

Example implementation 60: A polynucleotide, according to Example implementation 59, WHEREIN the polynucleotide of interest encodes the protein XBP1s-LGF-ATF6f-HA.

Example implementation 61: A polynucleotide, according to Example implementation 59, WHEREIN the polynucleotide of interest encodes the protein XBP1s-LF-ATF6f-HA.

Example implementation 62: A polynucleotide, according to Example implementation 59, WHEREIN the polynucleotide of interest encodes the protein XBP1s-L4H4-ATF6f-HA.

Example implementation 63: A polynucleotide, according to Example implementation 59, WHEREIN the polynucleotide of interest encodes the protein ATF6f-LGF-XBP1s-HA.

Example implementation 64: A polynucleotide, according to Example implementation 59, WHEREIN the polynucleotide of interest encodes the protein ATF6f-LF-XBP1 s-HA.

Example implementation 65: A polynucleotide, according to Example implementation 59, WHEREIN the polynucleotide of interest encodes the protein ATF6f-L4H4-XBP1s-HA.

Example implementation 66: A polynucleotide, according to Example implementation 42, WHEREIN the polynucleotide of interest acts systemically close to dopaminergic neurons of the substantia nigra.

Example implementation 67: A polynucleotide, according to Example implementation 67, WHEREIN the polynucleotide of interest acts systemically close to or with dopaminergic neurons of the substantia nigra.

Example implementation 68: A plasmid, WHEREIN it comprises the sequences of an adeno-associated, an expression cassette flanked by the ITRs of the adeno-associated virus, where such expression cassette comprises a promoter, a coding region for immune response and a polynucleotide of interest, such as the one deposited in the international body of biological deposits, Instituto de Investigaciones Agropecuarias de Chile, INIA, under deposit number RGM 2231.

Example implementation 69: A plasmid, WHEREIN it comprises the sequences of an adeno-associated virus, an expression cassette flanked by the ITRs of the adeno-associated virus, where such expression cassette comprises a promoter, a coding region for immune response and a polynucleotide of interest, such as the one deposited in the international body of biological deposits, Instituto de Investigaciones Agropecuarias de Chile, INIA, under deposit number RGM 2232.

Example implementation 70: A plasmid, WHEREIN it comprises the sequences of an adeno-associated, an expression cassette flanked by the ITRs of the adeno-associated virus, where such expression cassette comprises a promoter, a coding region for immune response and a polynucleotide of interest, such as the one deposited in the international body of biological deposits, Instituto de Investigaciones Agropecuarias de Chile, INIA, under deposit number RGM 2233.

Example implementation 71: A plasmid, WHEREIN it comprises the sequences of an adeno-associated, an expression cassette flanked by the ITRs of the adeno-associated virus, where such expression cassette comprises a promoter, a coding region for immune response and a polynucleotide of interest, such as the one deposited in the international body of biological deposits, Instituto de Investigaciones Agropecuarias de Chile, INIA, under deposit number RGM 2234.

Example implementation 72: A plasmid, WHEREIN it comprises the sequences of an adeno-associated, an expression cassette flanked by the ITRs of the adeno-associated virus, where such expression cassette comprises a promoter, a coding region for immune response and a polynucleotide of interest, such as the one deposited in the international body of biological deposits, Instituto de Investigaciones Agropecuarias de Chile, INIA, under deposit number RGM 2235.

Example implementation 73: A plasmid, WHEREIN it comprises the sequences of an adeno-associated, an expression cassette flanked by the ITRs of the adeno-associated virus, where such expression cassette comprises a promoter, a coding region for immune response and a polynucleotide of interest, such as the one deposited in the international body of biological deposits, Instituto de Investigaciones Agropecuarias de Chile, INIA, under deposit number RGM 2236.

Example implementation 74: An adeno-associated virus, WHEREIN it comprises the viral genome described in Example implementations 42 to 64.

Example implementation 75: A method for obtaining an adeno-associated viral vector WHEREIN it comprises the steps of:
  a. Providing a cell comprising a polynucleotide according to any of the Example implementations 42 to 64, with the AAV Cap proteins, with the AAV Rep proteins, and the viral proteins on which AAV depends for its replication;
  b. Keeping the cells under proper conditions for assembly of the AAV; and
  c. Purifying the adeno-associated viral vector produced by the cell.

Example implementation 76: A method, according to Example implementation 75, WHEREIN the AAV is dependent on the replication deriving from the adenovirus.

Example implementation 77: A method, according to Example implementations 69 and 75, WHEREIN the Cap and Rep proteins of the adeno-associated virus are derived from an AAV selected from the serotypes AAV 2, AAV 6, AAV 7, AAV 8, AAV 9, AAV 10, AAV 11 and pseudotyped AAVs.

Example implementation 78: A method, according to Example implementation 77, WHEREIN the Cap and Rep proteins of the adeno-associated virus are derived from the serotype AAV2.

The invention claimed is:

1. A method for reducing protein misfolding or aggregation, comprising contacting a cell with an adeno-associated vector (AAV), wherein the AAV comprises an expression cassette comprising a transcription regulatory region comprising a promoter operatively bound to a polynucleotide of interest coding a fusion protein, wherein the fusion protein comprises XBP1s, ATF6f, and a bridge or linker sequence.

2. The method of claim 1, wherein the AAV is a serotype selected from a group consisting of AAV2, AAV6, AAV7, AAV8, AAV9, AAV10, AAV11 and pseudo-typed AAVs.

3. The method of claim 1, wherein the transcription regulatory region comprises a promoter region selected from the group consisting of CMV, PGK1, CAMKII, THY1 and GAD34.

4. The method of claim 1, wherein the AAV comprises a detection epitope coding region selected from the group consisting of Ha, Flag, Gfp, His and Myc.

5. The method of claim 1, wherein the expression cassette comprises a post-transcriptional regulatory region.

6. The method of claim 5, wherein the post-transcriptional regulatory region is a post-transcriptional regulatory element of Woodchuck Hepatitis Virus (WHP).

7. The method of claim 1, wherein the bridge or linker sequence comprises the LGF, L4H4 and LF sequences.

8. The method of claim 1, wherein the polynucleotide of interest encodes a fusion protein selected from the group consisting of XBP1s-LGF-ATF6f-HA, XBP1s-LF-ATF6f-HA, XBP1s-L4H4-ATF6f-HA, ATF6f-LGF-XBP1s-HA, ATF6f-LF-XBP1s-HA and ATF6f-L4H4-XBP1s-HA, which act systemically close to or with neuronal cells.

9. The method of claim 1, wherein the cell is a neuron of a subject suffering from a neurodegenerative disease.

10. The method of claim 9, wherein the method reduces symptoms associated with the neurodegenerative disease.

11. The method of claim 10, wherein the neurodegenerative disease is Parkinson's disease, Huntington's disease, Alzheimer's disease, or Amyotrophic Lateral Sclerosis.

12. The method of claim 10, wherein the neurodegenerative disease is Parkinson's disease or Huntington's disease.

* * * * *